US008834696B2

United States Patent
Kim et al.

(10) Patent No.: US 8,834,696 B2
(45) Date of Patent: Sep. 16, 2014

(54) AMPLIFIED ELECTROKINETIC FLUID PUMPING SWITCHING AND DESALTING

(75) Inventors: Sung Jae Kim, Melrose, MA (US); Jongyoon Han, Bedford, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 13/011,107

(22) Filed: Jan. 21, 2011

(65) Prior Publication Data
US 2011/0198225 A1 Aug. 18, 2011

Related U.S. Application Data

(63) Continuation of application No. PCT/US2009/051420, filed on Jul. 22, 2009.

(60) Provisional application No. 61/129,819, filed on Jul. 22, 2008, provisional application No. 61/084,541, filed on Jul. 29, 2008.

(51) Int. Cl.
| | | |
|---|---|---|
| G01N 27/447 | (2006.01) | |
| B01D 57/02 | (2006.01) | |
| C02F 1/469 | (2006.01) | |
| B82Y 30/00 | (2011.01) | |
| F04B 19/00 | (2006.01) | |
| B01L 3/00 | (2006.01) | |
| C02F 103/08 | (2006.01) | |

(52) U.S. Cl.
CPC ............ *B01D 57/02* (2013.01); *B01L 3/502753* (2013.01); *F04B 19/006* (2013.01); *C02F 1/4698* (2013.01); *B01L 2400/0418* (2013.01); *B01L 3/50273* (2013.01); *C02F 1/4696* (2013.01); *G01N 27/447* (2013.01); *C02F 1/469* (2013.01); *C02F 2103/08* (2013.01); *B01L 2400/0487* (2013.01); *Y10S 977/70* (2013.01)
USPC ............ 204/454; 204/452; 204/601; 977/700

(58) Field of Classification Search
USPC ............ 977/700; 204/452, 454, 601, 403.01; 205/779
See application file for complete search history.

(56) References Cited

U.S. PATENT DOCUMENTS

| | | | |
|---|---|---|---|
| 5,685,980 | A | 11/1997 | Patapoff |
| 6,325,907 | B1 | 12/2001 | Andelman |

(Continued)

FOREIGN PATENT DOCUMENTS

| | | |
|---|---|---|
| KR | 1020080019573 | 3/2008 |
| WO | 2006081270 A2 | 8/2006 |

OTHER PUBLICATIONS

J. Han, H. G. Craighead, J. Vac. Sci. Technol., A 17, 2142-2147 (1999).*

(Continued)

*Primary Examiner* — Luan Van
*Assistant Examiner* — Steven Rosenwald
(74) *Attorney, Agent, or Firm* — Gesmer Updegrove LLP

(57) ABSTRACT

The present invention provides a device and methods of use thereof for desalting a solution. The methods, inter-alia, make use of a device comprising microchannels, which are linked to conduits, whereby induction of an electric field in the conduit results in the formation of a space charge layer within the microchannel. The space charge layer provides an energy barrier for salt ions and generates an ion depletion zone proximal to the linkage region between the microchannel and the conduit. The method thus enables the removal of salt ions from the region proximal to the conduit and their accumulation in a region distant from the conduit, within the microchannel.

98 Claims, 22 Drawing Sheets

(56) References Cited

U.S. PATENT DOCUMENTS

| | | | |
|---|---|---|---|
| 7,186,336 B2* | 3/2007 | Gerhardt et al. | 210/198.2 |
| 2004/0144648 A1 | 7/2004 | Jacobson et al. | |
| 2005/0045466 A1 | 3/2005 | Bitterly et al. | |
| 2005/0284762 A1* | 12/2005 | Astorga-Wells et al. | 204/451 |
| 2006/0180469 A1* | 8/2006 | Han et al. | 204/601 |
| 2006/0254920 A1* | 11/2006 | Gascoyne et al. | 204/547 |

OTHER PUBLICATIONS

International Preliminary Report on Patentability issued in connection with PCT Application No. PCT/US2009/051420, mailed on Feb. 3, 2011.

Harrison, "Population and sustainable development: Five years after Rio." United Nations Population Fund (UNFPA), vol. 2, p. 38, 1997.

Engelman et al., "Sustaining water: Population and the future of renewable water supplies." Population Action International, p. 56, 1993.

Shannon et al., "Science and technology for water purification in the coming decades." Nature, vol. 452, p. 301-310, Mar. 2008.

Kessler et al., "Drinking water from sea water by forward osmosis." Desalination, vol. 18, p. 297-306, 1976.

Probstein, "Physicochemical Hydrodynamics: An Introduction." New York: John Wiley & Sons, Inc., 1994.

Rubinstein et al., "Voltage against Current Curves of Cation Exchange Membranes." Journal of Chemical Society Faraday Transactions II, vol. 75, p. 231-246, 1979.

Holtzel et al., "Ionic conductance of nanopores in microscale analysis sytems: Where microfluidics meets nanofluidics." Journal of Separation Science, vol. 30, p. 1398-1419, 2007.

Pu et al., "Ion-Enrichment and Ion-Depletion Effect of Nanochannel Structures." Nano Letters, vol. 4, No. 6, p. 1099-1103, 2004.

Kim et al., "Concentration Polarization and Nonlinear Electrokinetic Flow near a Nanofluidic Channel." Physical Review Letters, vol. 99, p. 044501 1-4, Jul. 2007.

Kim et al., "Self-Sealed Vertical Polymeric Nanoporous-Junctions for High-Throughput Nanofluidic Applications." Analytical Chemistry, vol. 80, p. A-E, 2008.

Kapp, Eleanor, "The Precipitation of Calciuim and Magnesium From Sea Water by Sodium Hydroxide." The Biological Bulletin, vol. 55, p. 453-458, 1928.

"Guidelines for Drinking-water Quality." World Health Organization, vol. 1, 2008.

Kovacs, Gregory, "Micromachined Transducers Sourcebook." Boston: McGraw-Hill, p. 792-793, 1998.

Veerapaneni et al., "Reducing energy consumption for seawater desalination." Journal AWWA, vol. 99, p. 95-106, Jun. 2007.

Fu et al., "A patterned anisotropic nanofluidic sieving structure for continuous-flow separation of DNA and proteins." Nature Nanotechnology, vol. 2, p. 121-128, Feb. 2007.

Wang et al., "Million-fold Preconcentration of Proteins and Peptides by Nanofluidic Filter." Analytical Chemistry, vol. 77, No. 14, p. 4293-4299, Jul. 2005.

Chen et al., "Effect of Intraparticle Porosity and Double Layer Overlap on Electrokinetic Mobility in Multiparticle Systems." Langmuir, vol. 19, p. 10901-10908, 2003.

Rubinstein et al., "Electrocenvective instability in concentration polarization and nonequilibrium electro-osmotic slip." Physical Review, vol. 72, p. 011505 1-19, 2005.

Plecis et al., "Ionic Transport Phenomena in Nanofluidics: Experimental and Theoretical Study of the Exclusion-Enrichment Effect on a Chip." Nano Letters, vol. 5, No. 6, p. 1147-1155, 2005.

Kim et al., "Concentration Polarization and Nonlinear Electrokinetic Flow Near a Nanofluidic Channel" Physical Review Letters, Jul. 27, 2007, The American Physical Society, pp. 044501-1-044501-4.

International Search Report and the Written Opinion issued in connection with corresponding PCT Application No. PCT/US09/51420, mailed on Sep. 15, 2009.

English Translation of Japanese Notice of Grounds for Rejection mailed on Jul. 3, 2012, in connection with Japanese Patent Application No. 2011-520168 filed on Jul. 22, 2009.

English Translation of Korean Notice of Preliminary Rejection issued on Sep. 30, 2013 in connection with Korean Patent Appln. No. 10-2011-704113, 2 pages.

Korean Office Action and the English translation thereof issued on Feb. 28, 2013 in connection with Korean Patent Application No. 10-2011-7004113.

JP Office Action issued in connection with corresponding JP Application No. 2011-520168, mailed on Feb. 5, 2013 and English translation of same.

English translation of the Chinese Office Action issued on Mar. 20, 2013 in connection with Chinese Patent Application No. 200980137193.2 filed on Jul. 22, 2009, 4 pages.

English translation of a MX Office Action mailed on Nov. 7, 2013 in connection with corresponding Mexican Application No. MX/a/2011/000940.

English translation of Israeli Notice of Rejection issued Dec. 8, 2013 in connection with Israeli Patent Application No. 210817.

Canadian Patent Office Examination Report issued on Mar. 4, 2014 in connection with Canadian Application No. 2731727, 5 pages.

Indian Patent Office Examination Report issued on Feb. 18, 2014 in connection with Indian Application No. 133/MUMNO/2011, 10 pages.

\* cited by examiner

Single gate device (SG)

Dual gate device (DG)

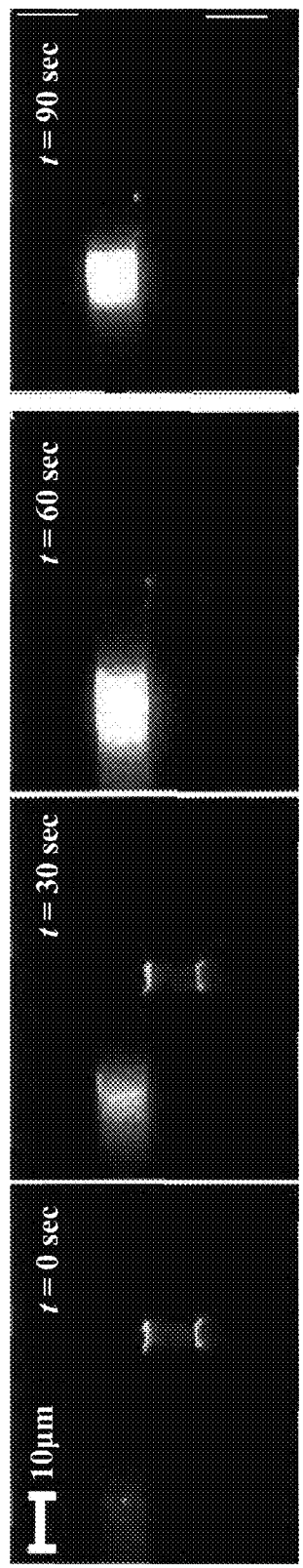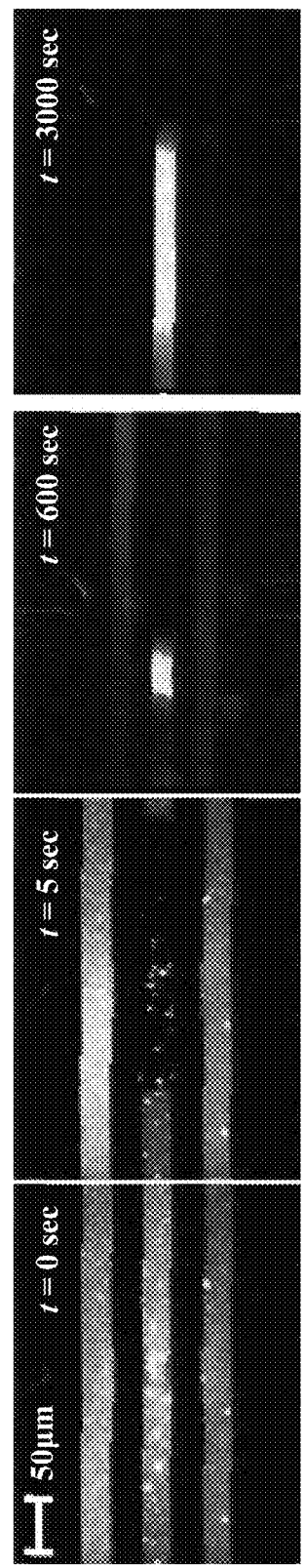
FIG. 8A
FIG. 8B

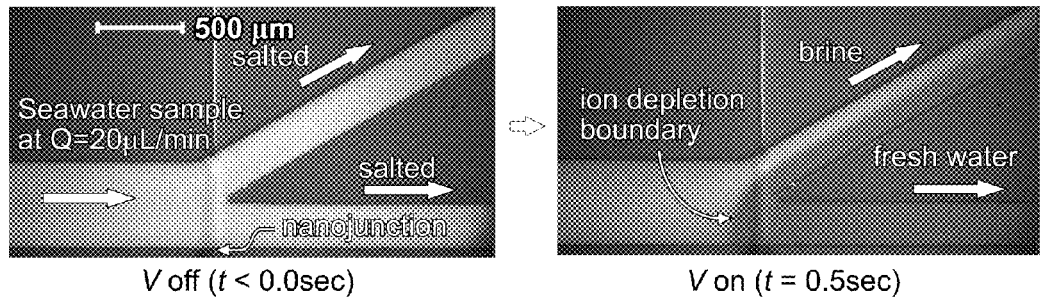
FIG. 11A
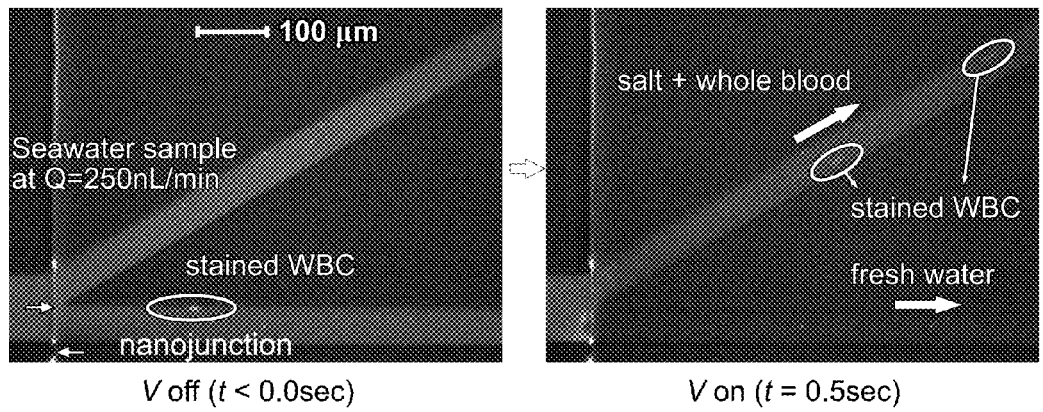
FIG. 11B
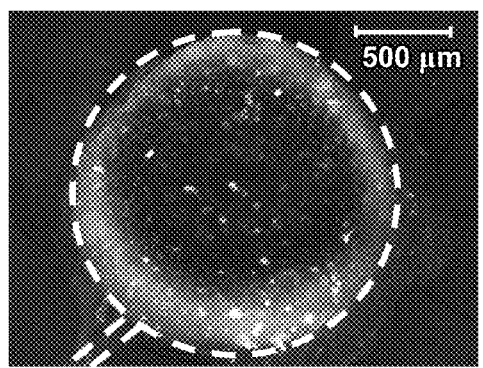 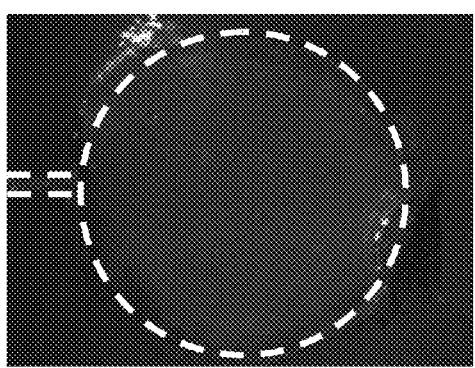
FIG. 11C     FIG. 11D

AMPLIFIED ELECTROKINETIC FLUID PUMPING SWITCHING AND DESALTING

PRIORITY INFORMATION

The present application is a continuation of PCT Application No. PCT/US2009/51420, filed on Jul. 22, 2009, which claims priority to U.S. Provisional Application Ser. Nos. 61/129,819, filed Jul. 22, 2008 and 61/084,541, filed Jul. 29, 2008. All the applications are incorporated herein by reference in their entireties

SPONSORSHIP INFORMATION

The invention was made with government support under Grant Nos. R01 EB005743 and R01 CA119402 awarded by the National Institutes of Health. The government has certain rights in the invention

FIELD OF THE INVENTION

This invention provides methods for accelerating liquid flow in a microfluidic device. The invention provides methods for amplified pumping, for flow direction switching and for direct (membraneless) seawater desalination. The methods are based on electrically-induced localization of charged species in solution, which cause the enhancement of fluid flow. The localized charged species can be further separated, isolated and removed from the solution.

BACKGROUND OF THE INVENTION

One of the major challenges of proteomics is the sheer complexity of biomolecular samples, such as blood serum or cell extract. Typical blood samples could contain more than 10,000 different protein species, with concentrations varying over 9 orders of magnitude. Such diversity of proteins, as well as their huge concentration ranges, poses a formidable challenge for sample preparation in proteomics.

Conventional protein analysis techniques, based on multi-dimensional separation steps and mass spectrometry (MS), fall short because of the limited separation peak capacity (up to ~3000) and dynamic range of detection (~$10^4$). Microfluidic biomolecule analysis systems (so-called µTAS) hold promise for automated biomolecule processing. Various biomolecule separation and purification steps, as well as chemical reaction and amplification has been miniaturized on a microchip, demonstrating orders of magnitude faster sample separation and processing. In addition, microfluidic integration of two different separation steps into a multidimensional separation device has been demonstrated. However, most microfluidic separation and sample processing devices suffers from the critical issue of sample volume mismatch. Microfluidic devices are very efficient in handling and processing 1 pL~1 nL of sample fluids, but most biomolecule samples are available or handled in a liquid volume larger than 1 µL. Therefore, microchip-based separation techniques often analyze only a small fraction of available samples, which significantly limits the overall detection sensitivity. In proteomics, this problem is exacerbated by the fact that information-rich signaling molecules (cytokines and biomarkers, e.g.) are present only in trace concentrations (nM~pM range), and there is no signal amplification technique such as polymerase chain reaction (PCR) for proteins and peptides.

What is needed is an efficient sample concentrator, which can take a typical sample volume of microliters or more and concentrate molecules therein into a smaller volume so that such molecules can be separated and detected much more sensitively. Several strategies are currently available to provide sample preconcentration in liquid, including field-amplified sample stacking (FAS), isotachophoresis (ITP), electrokinetic trapping, micellar electrokinetic sweeping, chromatographic preconcentration, and membrane preconcentration. Many of these techniques are originally developed for capillary electrophoresis, and require special buffer arrangements and/or reagents. Efficiency of chromatographic and filtration-based preconcentration techniques depends on the hydrophobicity and the size of the target molecules. Electrokinetic trapping can be used for any charged biomolecule species, but generally requires nanoporous charge-selective membranes for the operation. Overall, the demonstrated concentration factors for the existing preconcentration schemes are limited to ~1000, and their application to the integrated microsystems is difficult due to various operational constraints such as reagents and materials requirements.

On the other hand, removal of charged species and specifically salt is needed in microfluidic devices in order to produce pure fluids for synthesis and analysis. When the fluid is water, purified water is needed for drinking.

Fresh water is the vital resource for human life. However, population growth, enhanced living standards, along with expansion in industrial and agricultural activities are urging unprecedented demands on the clean water supplies all over the world. OECD and UN have reported that 0.35 billion people are suffering from the water shortage now in 25 countries, especially in the middle-east and Africa, but it will grow up to 3.9 billion people (⅔ of world population) in 52 countries by 2025. The shortage of fresh water is one of the acute challenges that the world is facing now and thus energy efficient desalination strategy can provide substantial answer for the water-crisis. Converting abundant seawater into fresh water can provide the solution to the worldwide water shortage problem, since about 97% of the total water resources on earth is seawater and only 0.5% of the total water resources are potable fresh water. Historically, distillation has been the method of choice for seawater desalination, in spite of its high capital and energy costs, suitable for middle-eastern countries where the fuel required for distillation is relatively inexpensive. The other standard approaches to seawater desalination are reverse osmosis (RO) and electro-dialysis (ED), with relatively good energy efficiencies (~5 Wh/L for RO, and 10~25 Wh/L for ED). The RO process requires the generation of large pressure in order to overcome seawater osmotic pressure (~27 times of atmospheric pressure) across the semipermeable membranes used. The ED process utilizes electrical currents to move ions selectively through perm-selective membrane, leaving pure water behind. The three seawater desalination techniques mentioned above require large scale systems with significant power consumption and other large scale infrastructure considerations which critically increase the operation cost of such systems. These features render the methods unsuitable for disaster-stricken areas or underdeveloped countries.

This presents a significant global challenge, since the areas affected by acute water shortage are often in the poorest, most underdeveloped countries. Lack of clean water also presents significant health, energy and economic challenges to the population in these countries. In this sense, small scale or portable seawater desalination systems with low power consumption and high throughput would be very useful in many important government, civilian and military needs, including humanitarian operations in disaster-stricken areas or resource-limited settings. Another significant challenge in seawater desalination is detecting and removing micro/macro particles, bacteria, and other pathogens contained in the source water. These particles and microorganisms cause membrane fouling, which is a major issue both for RO and ED systems. The forward osmosis process (extracting the seawater into even saltier liquid, followed by reverse osmosis) was utilized for filtration in a seawater desalination process, but its operation suffers from high costs due to additional energy consumption.

SUMMARY OF THE INVENTION

In one embodiment, this invention provides a micro/nanofluidic system to convert seawater (~500 mM salinity) to potable water (<10 mM salinity) utilizing ion concentration polarization. A continuous stream of seawater is divided into desalted and concentrated streams according to methods relying on the ion depletion phenomenon, and the divided two streams are flown into different microchannels. The key distinct feature of this scheme is that both salts and larger particles (cells, viruses, and microorganisms) are pushed away (not through) from the nanoporous membrane in a continuous, steady-state flow operation, significantly reducing the possibility of membrane fouling and salt accumulation that plagues the membrane in the reverse osmosis and other membrane filtration methods. Using a simple microfluidic unit device, continuous desalination of seawater at a power consumption of less than 5 Wh/L was demonstrated. Such desalination is comparable to state of the art electrodialysis and reverse osmosis desalination systems. The presenting methods would be ideally suited for small/medium scale desalination applications with the possibility of battery-powered operation that may eliminate the need for larger desalination plants.

This invention provides, in one embodiment, a method for accelerating liquid flow in a microfluidic device, the method comprising the steps of:
introducing a liquid comprising charged species from a source into a microfluidic device comprising:
a substrate
at least one sample microchannel through which said liquid comprising charged species can be made to pass from a first side to a second side;
at least one buffer microchannel or reservoir comprising a buffer;
at least one conduit linked to said sample microchannel and to said buffer microchannel or reservoir; and
at least one unit to induce an electric field in said conduit, said sample microchannel, said buffer microchannel or reservoir or a combination thereof;
inducing a first electric field in said sample microchannel whereby electroosmotic flow is induced in said sample microchannel, said flow further introducing said liquid into said device and said flow is controlled by the strength of said first electric field; and
inducing a second electric field in said conduit, whereby ion depletion occurs in said sample microchannel in a region proximal to said conduit and whereby said ion depletion accelerates flow in said sample microchannel.

In one embodiment, the first electric field in the sample microchannel is generated by applying a higher voltage to the first side of the sample microchannel and a lower voltage to the second side of the sample microchannel. In one embodiment, the higher voltage, the lower voltage or a combination thereof is positive voltage. In one embodiment, the positive voltage is between 50 mV and 500 V. In one embodiment, the higher voltage is positive and the lower voltage is achieved by electrically grounding the second side of the sample microchannel.

In one embodiment, the second electric field in the conduit is generated by applying a higher voltage to the side of the conduit that is linked to the sample microchannel and a lower voltage to the side of the conduit that is linked to the buffer microchannel. In one embodiment, the higher voltage is positive and the lower voltage is applied by electrically grounding the buffer microchannel or reservoir linked to the conduit. In one embodiment, the higher voltage is the result of the two voltages applied to the first side and to the second side of the sample microchannel. In one embodiment, the higher voltage has an intermediate value lying between the values of the two voltages applied to the first side and to the second side of the sample microchannel.

In one embodiment, the first and the second electric fields are induced by applying a voltage of 60 V to the first side of the sample microchannel and by applying a voltage of 40 V to the second side of the sample microchannel and wherein the buffer microchannel or reservoir is electrically grounded.

In one embodiment, upon introduction of a solution comprising charged species to the sample microchannel and independent induction of the electric field in the conduit and the electric field in the sample microchannel, the charged species are confined to a region within the sample microchannel that is distant from the conduit.

In one embodiment, the sample microchannel further comprises a first outlet for low salt concentration solution and a second outlet for high salt concentration solution.

In one embodiment, the width of the sample microchannel, the buffer microchannel or a combination thereof is between 1-100 μm. In one embodiment, the depth of the sample microchannel, the buffer microchannel or a combination thereof is between 0.5-50 μm. In one embodiment, the width of the conduit is between 100-4000 nanometers. In one embodiment, the width of the conduit is between 1-100 micrometers. In one embodiment, the depth of the conduit is between 20-100 nanometers. In one embodiment, the depth of the conduit is between 1-100 micrometers.

In one embodiment, the surface of the sample microchannel has been functionalized to reduce adsorption of species of interest to the surface. In one embodiment, the surface of said conduit and/or said first or buffer microchannel has been functionalized to enhance the operation efficiency of the device.

In one embodiment, an external gate voltage is applied to the substrate of the device, to enhance the operation efficiency of the device.

In one embodiment, the sample microchannel, said buffer microchannel, said conduit or combination thereof, are formed by lithography and etching processes.

In one embodiment, the transparent material is borosilicate glass (Pyrex™), silicon dioxide, silicon nitride, quartz or SU-8.

In one embodiment, the device is coated with a low-autofluorescent material.

In one embodiment, the device is coupled to a pump. In one embodiment, the device is coupled to a sensor, separation system, detection system, analysis system or combination thereof. In one embodiment, the detection system comprises an illumination source, a camera, a computer, a luminometer, a spectrophotometer, or a combination thereof.

In one embodiment, the liquid flow speed in said sample microchannel is between 100 μm/sec and 10 mm/sec.

In one embodiment, the device comprises multiple sample microchannels, multiple buffer microchannels, multiple conduits or combinations thereof. In one embodiment, the multiple microchannels, conduits or combinations thereof are arranged with a particular geometry or in an array. In one embodiment, the array comprises at least 1000 sample microchannels, at least 1000 buffer microchannels and at least 1000 conduits.

In one embodiment, the device length, width, height or a combination thereof ranges between 10 cm to 30 cm.

In one embodiment, the geometry or said array comprises perpendicular orientation of said microchannels with respect to said conduits.

In one embodiment, the liquid volume flow rate is at least 1 L/min. In one embodiment, the liquid volume flow rate ranges between 60-100 L/min. In one embodiment, the liquid comprising charged species is sea water. In one embodiment, the electrical power needed for device operation ranges between 10 w to 100 w. In one embodiment, the flow through said sample microchannel is continuous.

In one embodiment, the device is part of an apparatus. In one embodiment, the apparatus is handheld/portable. In one embodiment, the apparatus is a table top apparatus.

In one embodiment, this invention provides a method of diminishing the salt concentration of or desalting a solution, the method comprising the steps of:
  introducing a liquid comprising salt ions from a source into a microfluidic device comprising:
  a substrate
  at least one sample microchannel through which said liquid comprising salt ions can be made to pass;
  at least one buffer microchannel comprising a buffer;
  at least one conduit;
  a unit to induce an electric field in said conduit, said sample microchannel, said buffer microchannel or a combination thereof; and
  a unit to induce an electrokinetic or pressure driven flow in said sample microchannel;
    inducing an electric field in said sample microchannel whereby electroosmotic flow is induced in said sample microchannel, said flow further introducing said liquid into said device and said flow is controlled by the strength of said electric field; and
    inducing an electric field in said conduit, whereby a space charge layer is formed within said sample microchannel, providing an energy barrier to ionic species and whereby ion depletion occurs in said sample microchannel in a region proximal to said conduit and said salt ions are confined to a region within said sample microchannel that is distant from said conduit.

In one embodiment, seawater feeding can be done by gravity. In one embodiment, gravity induced seawater feeding is an advantage over RO or ED methods because it does not require additional power for the sample delivery.

In one embodiment, the ICP desalination process can be run by a photovoltaic cell (i.e. a solar cell). One of the most significant features of the ICP desalination of the present invention is low power consumption that means that the operation power can be supplied by either rechargeable battery or by photovoltaic cells. Current photovoltaic cell can produce an average of ~25 mW/cm. With this efficiency, the total area of a photovoltaic cell needed to operate a device of this invention should be ~2700 cm$^2$ (2250 µW×3×10$^4$/25 mW/cm$^2$). Such photovoltaic cell area can power a device with a flow rate of 300 mL/min. This size (~50 cm×50 cm) of flexible photovoltaic cell needed is adequate for a portable system, which may render this portable desalination system solar-powered.

In one embodiment, the liquid comprising salt is sea water. In one embodiment, the method is used for desalting sea water for drinking. In one embodiment, the sample microchannel further comprises a first outlet for low salt concentration solution and a second outlet for high salt concentration solution. In one embodiment, the first outlet for low salt concentration solution is linked to said ion depletion zone in said sample microchannel and the second outlet for high salt concentration solution is linked to said region that is distant from said conduit wherein salt ions are confined.

In one embodiment, the flow through said sample microchannel is continuous. In one embodiment, the method is used for filtering solutions for synthesis, detection analysis, purification, or a combination thereof. In one embodiment, the method is used for removing contaminants from water.

In one embodiment, this invention provides a method of stopping or switching the direction of liquid flow, the method comprising the steps of:
  introducing a liquid comprising charged species from a source into a microfluidic device comprising:
  a substrate
  at least one sample microchannel through which said liquid comprising charged species can be made to pass from a first side to a second side thus generating a first flow;
  at least one buffer microchannel or reservoir comprising a buffer;
  at least one conduit linked to said sample microchannel and to said buffer microchannel or reservoir; and
  at least one unit to induce an electric field in said conduit, said sample microchannel, said buffer microchannel or reservoir or a combination thereof;
  such that the liquid flow direction is from a first side to a second side of said sample microchannel.
    inducing a first electric field in said sample microchannel and a second electric field in said conduit, whereby ion depletion occurs in said sample microchannel in a region proximal to said conduit whereby a second electrokinetic flow is induced in said sample microchannel, said second flow direction is from said second side to said first side of said microchannel and said electroosmotic second flow is controlled by the strength of said first and said second electric fields;
  whereby second flow induced from said second side to said first side of said microchannel opposes said first flow from first side to said second side, and whereby second flow induced from second side to first side, may stop said first flow or reverse the direction of said first flow.

BRIEF DESCRIPTION OF THE DRAWINGS

FIG. 8 demonstrates ion depletion in an embodiment of an (a) SG and (b) DG device, under ion depletion voltage conditions. The electric potential applied at the first side of the sample microchannel ($V_H$) was 20 V, and at the right side of the sample microchannel ($V_L$) was 10 V, while $V_H$ was 15 V in (b). Buffer channel(s) were electrically grounded.

FIG. 11 depicts microscopic images of: (a) Fluorescent image tracking of desalination processes under 20 µL/min external flow rate and applied electric field of 75V/cm. The inlet microchannel has the dimension of 500 µm width×100 µm depth. Seawater sample was injected and split into "salted" and "desalted" stream. (b) Fluorescent dyes (representing salts) and WBCs (representing micron-size particle) flew only through salted stream when ICP was triggered. In order to clear visualization of micron-size particles, small microchannel (100 µm width×15 µm depth) was used. Microscopic image of each reservoir ((c) salted and (d) desalted) after 1 hour desalination operation showing cleanness at desalted stream.

DETAILED DESCRIPTION OF THE INVENTION

Figure 1A:
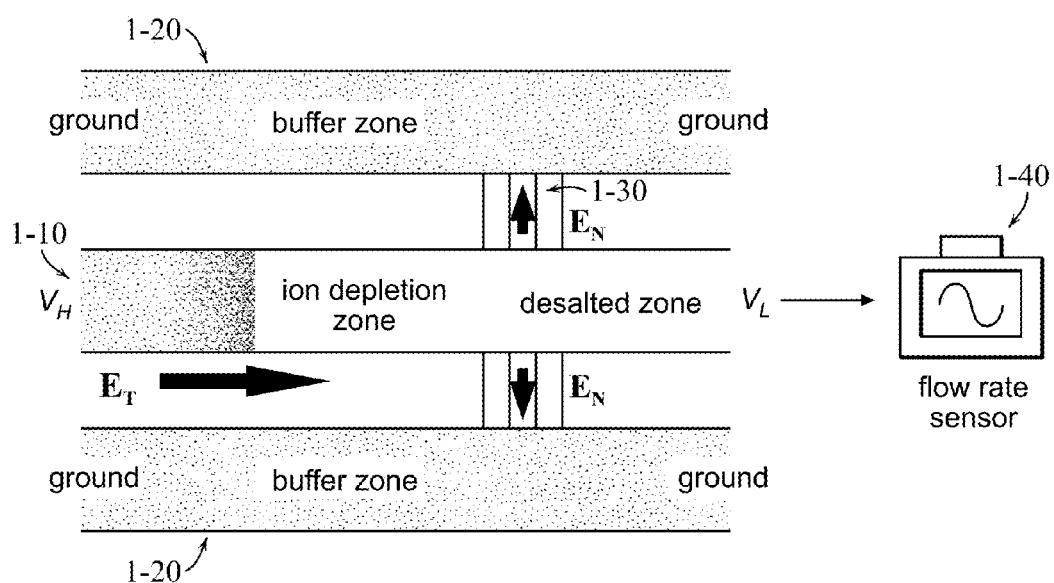
FIG. 1 schematically depicts embodiments of a device for accelerating liquid flow. A schematic diagram of micro/nanofluidic hybrid channel system and fluid behavior inside the channels is shown. Tangential electric field ($E_T$) and normal electric field ($E_N$) were applied along the center microchannel and across the conduit, respectively. (b) Fluid pumping using amplified electrokinetic flow (~70 mL/min; equil., ~350 nL/min; amplified electrokinetic-). In this case, $V_H$ was 500V and $V_L$ was 400V and transition time between those EOF's was less than 1.5 seconds. The equilibrium EOF was measured with the side reservoirs floated, while the amplified electrokinetic flow was measured with the side reservoirs grounded. (c) The two pumping modes of amplified electrokinetic flow as a function of the ET ($V_H$ was fixed at 500V, while $V_L$ was varied).

In one embodiment, the devices and systems proposed are highly portable with low power consumption. In one embodiment, the devices and systems proposed are highly adequate for several niche applications such as the military operation in war zone and humanitarian operations in disaster-stricken areas. Average water usage per person per day in United State is about 500 L which include drinking, bathing, cooking etc. Among these consumptions, at least 4 L of drinkable water is required for maintaining human daily life. The hurricane "Katrina" struck New Orleans on 2005 and 110,000 houses were completely destroyed. At that time, more than 400,000 people suffer from the lack of drinkable water in an area where a large-scale desalination plant can not be constructed. Another application for devices of this invention is as shipboard desalination system, both for military and civilian use. Aircraft carriers can hold 5,000~10,000 navy soldiers for a long combat period in the ocean. During this period, fresh water supply by desalination of abundant seawater is an essential source. For cases as in the two examples illustrated above, low-power consumption and portable desalination system would be highly required, with solar-powered operation as the best operation choice.

In one embodiment, operation of devices of the present invention was successfully demonstrated. According to this aspect and in one embodiment, unit operation was successfully demonstrated using seawater. In one embodiment, this invention provides integration of a large number of unit devices on a large area (e.g. 6-8" diameter plate). In one embodiment, a fabrication process for an array of unit devices is provided wherein the fabrication process does not involve expensive MEMS fabrication processes, but only require a plastic molding process. In addition, the cost of material for the device (plastic materials such as polydimethylsiloxane (PDMS)) is at least an order of magnitude lower than standard MEMS materials such as Si. In one embodiment, a process for mass production of devices is provided (e.g. by plastic molding). In one embodiment, the feature size of a unit device is of the order of ~0.1 mm, which is amenable for standard plastic manufacturing process such as (injection) molding.

In 2005, the total capacity of desalination facilities all around the World was 40 million ton/day (for use of 100~150 million peoples) and it is expected to increase up to 0.1 billion ton/day in 2015. In terms of market revenue, $25 billion market in 2006 will grow $60 billion in 2015 due to ever-increasing demand on the fresh water. Among these markets, about 10% of total market is for drinkable water for human life. Remaining 90% revenues are for the agricultural and industrial water supply which should be provided by large-scale plants.

In one embodiment, devices, systems and processes of this invention, when modified according to specific engineering and scalability considerations, find applications in this market of water desalination with a competitive advantage in process simplicity, lack of fouling, and energy efficiency. ICP desalination processes of the present invention have much better energy efficiency and no fouling. Therefore, ICP desalination processes of the present invention are advantageous when compared to the ED process which is currently a viable seawater desalination technique used in some countries (e.g. India).

Figure 10A:
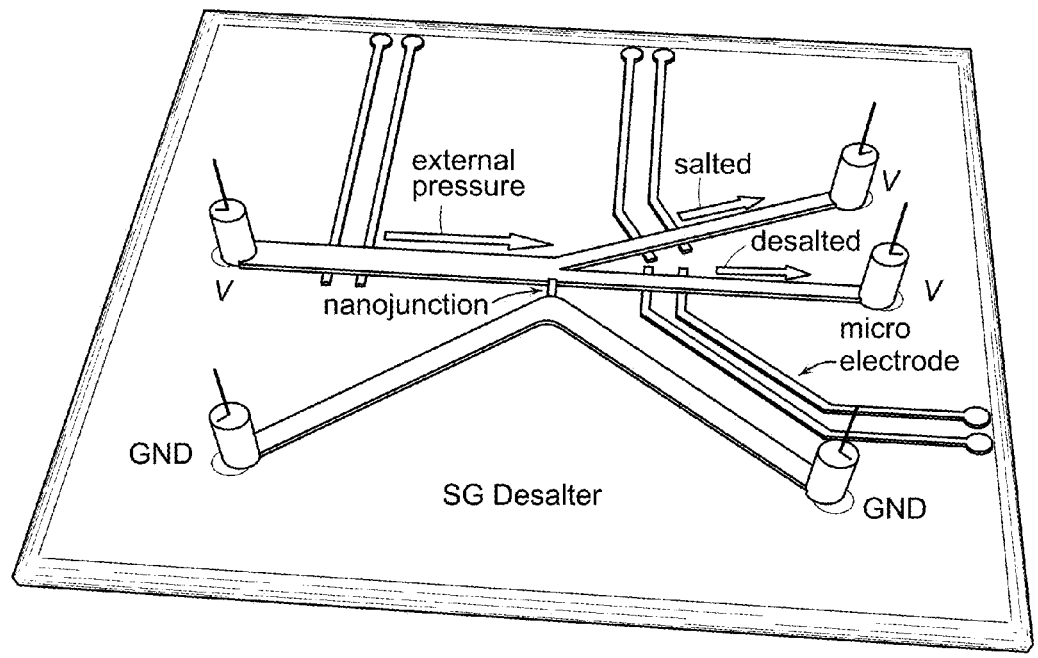
FIG. 10 is a schematic diagram of one embodiment of: (a) micro/nanofluidic desalination system with embedded microelectrode for measuring potential drop and (b) electrokinetic desalination operations associated with external pressure field.

In one embodiment, an objective of this invention is to demonstrate the feasibility of the novel desalination scheme that utilizes ion concentration polarization (ICP) for membraneless direct seawater desalination. ICP is a fundamental electrochemical transport phenomenon that occurs when ion current is passed through ion-selective membranes. Often referred to as ion depletion or enrichment, this phenomenon is due to the mismatch of charge carriers at the interface. The membrane (either nanochannel or nanoporous membrane) conducts only cations preferentially (cation exchange membrane), which is not matching with the ion conductivities in the bulk electrolyte. As a result, ion concentration gradients are generated on both sides of the membrane. Once ICP is triggered near the cation exchange membrane, the concentrations of both cations and anions decrease on the anodic side of the junction (ion depletion) and increase on the cathodic side (ion enrichment). In addition, any charged particles, cells, and other small colloids will also be depleted along with the ions. Combined with an external, pressure-driven flow, one could obtain a well defined steady-state depletion zone forming using the device as shown in FIG. 10(a) and (b). In one embodiment, the systems under study are composed of 2 parallel microchannels connected by nanochannels (or a nanoporous membrane) as shown in FIG. 10(a). Compared to the classical membrane geometry that blocked a straight channel, fluid flow in our design is not blocked by the membrane but rather flows in tangential directions to it.

This invention provides, in one embodiment, methods for accelerating liquid flow in a microfluidic device. The invention provides methods for amplified pumping, for flow direction switching and for desalting a solution. The methods are based on electrically-induced localization of charged species in solution, which cause the enhancement of fluid flow. The localized charged species can be further separated, isolated and removed from the solution.

In one embodiment, the invention provides a method for accelerating liquid flow in a microfluidic device, the method comprising the steps of:
introducing a liquid comprising charged species from a source into a microfluidic device comprising:
a substrate
at least one sample microchannel through which said liquid comprising charged species can be made to pass from a first side to a second side;
at least one buffer microchannel or reservoir comprising a buffer;
at least one conduit linked to said sample microchannel and to said buffer microchannel or reservoir; and
at least one unit to induce an electric field in said conduit, said sample microchannel, said buffer microchannel or reservoir or a combination thereof;
inducing a first electric field in said sample microchannel whereby electroosmotic flow is induced in said sample microchannel, said flow further introducing said liquid into said device and said flow is controlled by the strength of said first electric field; and
inducing a second electric field in said conduit, whereby ion depletion occurs in said sample microchannel in a region proximal to said conduit and whereby said ion depletion accelerates flow in said sample microchannel.

In one embodiment, the first electric field in the sample microchannel is generated by applying a higher voltage to the first side of the sample microchannel and a lower voltage to the second side of the sample microchannel. In one embodiment, the higher voltage, the lower voltage or a combination thereof is positive voltage. In one embodiment, the positive voltage is between 50 mV and 500 V. In one embodiment, the higher voltage is positive and the lower voltage is achieved by electrically grounding the second side of the sample microchannel.

In one embodiment, the second electric field in the conduit is generated by applying a higher voltage to the side of the conduit that is linked to the sample microchannel and a lower voltage to the side of the conduit that is linked to the buffer microchannel. In one embodiment, the higher voltage is positive and the lower voltage is applied by electrically grounding the buffer microchannel or reservoir linked to the conduit. In one embodiment, the higher voltage is the result of the two voltages applied to the first side and to the second side of the sample microchannel. In one embodiment, the higher voltage has an intermediate value lying between the values of the two voltages applied to the first side and to the second side of the sample microchannel.

In one embodiment, the first and the second electric fields are induced by applying a voltage of 60 V to the first side of the sample microchannel and by applying a voltage of 40 V to the second side of the sample microchannel and wherein the buffer microchannel or reservoir is electrically grounded.

In one embodiment, upon introduction of a solution comprising charged species to the sample microchannel and independent induction of the electric field in the conduit and the electric field in the sample microchannel, the charged species are confined to a region within the sample microchannel that is distant from the conduit.

In one embodiment, the sample microchannel further comprises a first outlet for low salt concentration solution and a second outlet for high salt concentration solution.

In one embodiment, the width of the sample microchannel, the buffer microchannel or a combination thereof is between 1-100 µm. In one embodiment, the depth of the sample microchannel, the buffer microchannel or a combination thereof is between 0.5-50 µM. In one embodiment, the width of the conduit is between 100-4000 nanometers. In one embodiment, the width of the conduit is between 1-100 micrometers. In one embodiment, the depth of the conduit is between 20-100 nanometers. In one embodiment, the depth of the conduit is between 1-100 micrometers.

In one embodiment, the surface of the sample microchannel has been functionalized to reduce adsorption of species of interest to the surface. In one embodiment, the surface of said conduit and/or said first or buffer microchannel has been functionalized to enhance the operation efficiency of the device.

In one embodiment, an external gate voltage is applied to the substrate of the device, to enhance the operation efficiency of the device.

In one embodiment, the sample microchannel, said buffer microchannel, said conduit or combination thereof, are formed by lithography and etching processes.

In one embodiment, the device is comprised of a transparent material. In one embodiment, the transparent material is pyrex, silicon dioxide, silicon nitride, quartz or SU-8. In one embodiment, the device is coated with a low-autofluorescent material.

In one embodiment the device comprises a second substrate. In one embodiment the second substrate is used to cover or to seal the device. In one embodiment, the second substrate is comprised of the same material as the first substrate. In some embodiments the first and the second substrate are comprised of different materials. In some embodiments, the second substrate is made of a transparent material. In one embodiment, the transparent material is pyrex, silicon dioxide, silicon nitride, quartz or SU-8. In one embodiment, the second substrate is coated with a low-autofluorescent material.

In some embodiments, the device fabrication is completed via e.g. plasma bonding the first substrate to the second substrate. In some embodiment the first and second substrates are sealed together by the chemical adherence properties between the two substrates. In some embodiments adherence of the first substrate to glass, to polystyrene, to other polymeric material or to silicon is reversible. In one embodiment, if the second substrate is made of glass, polystyrene or other polymeric material or if the second substrate is made of silicon, adherence of the first substrate to the second substrate is reversible. In some embodiment one type of a second substrate can be initially attached to the first substrate. This second substrate can be later removed and replaced by another type of second substrate. In one embodiment the first and second substrates are clamped. In one embodiment clamping provides efficient and reversible sealing method for the device. In some embodiments, the first or second substrate is of a thickness that can affect any desired optical application, for example, in some embodiments, the device second substrate or cover may be constructed of a cover glass, such that confocal imaging of the device and the device contents is practical. In some embodiments the invention provides a kit of parts, for example a kit comprising the first substrate and the channels. According to this aspect and in some embodiments, the second substrate may be provided separately. Various second substrates may be provided with a kit, or in disposable cover packages. Second substrates can differ in material, sizes, geometry, surface roughness, electrical connections or electrical circuits embedded in the substrates and in their optical properties.

In one embodiment, the device is coupled to a pump. In one embodiment, the device is coupled to a sensor, separation system, detection system, analysis system or combination thereof. In one embodiment, the detection system comprises an illumination source, a camera, a computer, a luminometer, a spectrophotometer, or a combination thereof.

In one embodiment, the liquid flow speed in said sample microchannel is between 100 µm/sec and 10 mm/sec.

In one embodiment, the device comprises multiple sample microchannels, multiple buffer microchannels, multiple conduits or combinations thereof. In one embodiment, the multiple microchannels, conduits or combinations thereof are arranged with a particular geometry or in an array. In one embodiment, the array comprises at least 1000 sample microchannels, at least 1000 buffer microchannels and at least 1000 conduits.

In one embodiment, the device length, width, height or a combination thereof ranges between 10 cm to 30 cm.

In one embodiment, the geometry or said array comprises perpendicular orientation of said microchannels with respect to said conduits.

In one embodiment, the liquid volume flow rate is at least 1 L/min. In one embodiment, the liquid volume flow rate ranges between 60-100 L/min. In one embodiment, the liquid comprising charged species is sea water. In one embodiment, the electrical power needed for device operation ranges between 10 w to 100 w. In one embodiment, the flow through said sample microchannel is continuous.

In one embodiment, the device is part of an apparatus. In one embodiment, the apparatus is handheld/portable. In one embodiment, the apparatus is a table top apparatus.

In one embodiment, this invention provides a method of diminishing the salt concentration of or desalting a solution, the method comprising the steps of:

introducing a liquid comprising salt ions from a source into a microfluidic device comprising:

a substrate at least one sample microchannel through which said liquid comprising salt ions can be made to pass;

at least one buffer microchannel comprising a buffer;

at least one conduit;

a unit to induce an electric field in said conduit, said sample microchannel, said buffer microchannel or a combination thereof; and a unit to induce an electrokinetic or pressure driven flow in said sample microchannel;

inducing an electric field in said sample microchannel whereby electroosmotic flow is induced in said sample microchannel, said flow further introducing said liquid into said device and said flow is controlled by the strength of said electric field; and inducing an electric field in said conduit, whereby a space charge layer is formed within said sample microchannel, providing an energy barrier to ionic species and whereby ion depletion occurs in said sample microchannel in a region proximal to said conduit and said salt ions are confined to a region within said sample microchannel that is distant from said conduit.

In one embodiment, the liquid comprising salt is sea water. In one embodiment, the method is used for desalting sea water for drinking. In one embodiment, the sample microchannel further comprises a first outlet for low salt concentration solution and a second outlet for high salt concentration solution. In one embodiment, the first outlet for low salt concentration solution is linked to said ion depletion zone in said sample microchannel and the second outlet for high salt concentration solution is linked to said region that is distant from said conduit wherein salt ions are confined.

In one embodiment, the flow through said sample microchannel is continuous. In one embodiment, the method is used for filtering solutions for synthesis, detection analysis, purification, or a combination thereof. In one embodiment, the method is used for removing contaminants from water.

In one embodiment, this invention provides a method of stopping or switching the direction of liquid flow, the method comprising the steps of:
introducing a liquid comprising charged species from a source into a microfluidic device comprising:
a substrate
at least one sample microchannel through which said liquid comprising charged species can be made to pass from a first side to a second side thus generating a first flow;
at least one buffer microchannel or reservoir comprising a buffer;
at least one conduit linked to said sample microchannel and to said buffer microchannel or reservoir; and
at least one unit to induce an electric field in said conduit, said sample microchannel, said buffer microchannel or reservoir or a combination thereof;
such that the liquid flow direction is from a first side to a second side of said sample microchannel.
inducing a first electric field in said sample microchannel and a second electric field in said conduit, whereby ion depletion occurs in said sample microchannel in a region proximal to said conduit whereby a second electrokinetic flow is induced in said sample microchannel, said second flow direction is from said second side to said first side of said microchannel and said electroosmotic second flow is controlled by the strength of said first and said second electric fields;
whereby second flow induced from said second side to said first side of said microchannel opposes said first flow from first side to said second side, and whereby second flow induced from second side to first side, may stop said first flow or reverse the direction of said first flow.

I. Definitions

In one embodiment, accelerating liquid flow means increasing or enhancing flow rate. In one embodiment, accelerating liquid flow means that the liquid flows faster or at a higher speed. In one embodiment, accelerating the liquid flow means that the velocity of the fluid increases. In one embodiment, the velocity or speed is increased continuously. In one embodiment, continuous increase in flow speed or velocity is linear with time and/or with the voltages applied. In one embodiment the continuous increase is not linear. In one embodiment, the acceleration is performed in a step-wise manner. In one embodiment, flow rate is increased from one constant lower value to one constant higher value. In one embodiment, few acceleration steps are performed. In one embodiment, in each step the flow rate increases. In one embodiment, step-wise acceleration is governed by the electric fields induced on the liquid in the sample microchannel.

In one embodiment, a microfluidic device is a device comprising features with dimensions in the micron scale. In one embodiment, a microfluidic device is a device comprising features with at least one dimension between 1 micrometer (1 µm) and 1000 micrometer (1000 µm). In one embodiment, a microfluidic device comprises channels with width or depth in the micron scale and with length in the micron, millimeter or centimeter scale. In one embodiment, such channels are referred to as microchannels. In one embodiment, liquid can be made to pass through the microchannels. In one embodiment, a microfluidic device is a device through which fluid can be made to pass. In one embodiment, fluid can be a liquid. In one embodiment, the liquid can be pure. In one embodiment, the liquid can be a mixture. In one embodiment, the liquid can be a solution. In one embodiment, the solution can contain molecules or ions. In one embodiment, the solution can be aqueous or organic. In one embodiment, an aqueous solution containing ions can be a salt solution. In one embodiment the salt can be sea salt. In one embodiment, the sea salt is predominantly NaCl. In one embodiment, the salt comprises any alkali metal salt. In one embodiment the salt comprises an alkaline earth cation. In one embodiment, the salt comprises halogen ions. In one embodiment, the salt comprises complex ions. In one embodiment, the salt comprises ions of $H^+$, $Li^+$, $Na^+$, $K^+$, $Mg^{2+}$, $Ca^{2+}$, $Fe^{2+/3+}$, $Cu^{2+}$, $Ba^{2+}$, $Au^{3+}$, $F^-$, $Br^-$, $Cl^-$, $I^-$, $OH^-$, $NO_3$, $CO_3^{2-}$, $SO_4^{2-}$ or a combination thereof.

In one embodiment, the liquid comprises charged species. In one embodiment, charged means electrically charged. In one embodiment, charged species is a species that can be influenced by an electric field. In one embodiment, a charged species can be made to migrate in an electric field. In one embodiment, a charged species is attracted to a region with an opposite charge. In one embodiment, charged species migrate toward a region or a pole with an opposite charge, and are repelled or migrate away from regions with the same charge. In one embodiment, the charged species is a molecule, an ion, a particle, a cluster or an aggregate carrying an extra charge. In one embodiment, charged species is a species that is not electrically neutral. In one embodiment, the charged species is a peptide, a protein, a c nucleotide, a DNA or RNA segment, a nanoparticle, a microparticle, a bead. In one embodiment, the charged species is a biomolecule.

In one embodiment, a substrate is the supporting structure of a microfluidic device. In one embodiment, the substrate is the material on which or in which the microfluidic device is built. In one embodiment, the substrate is a piece of material from which the device or portions of it will be made. In one embodiment, the substrate or the device is comprised of a transparent material. In one embodiment, the transparent material is borosilicate glass (Pyrex™), silicone dixide, silicon nitride, quartz or SU-8. In one embodiment, the device is coated with a low-autofluorescent material. In one embodiment, the substrate, the device or portions of the device are made of silicon. In one embodiment, the substrate, the device or portions of the device are made of a polymer. In one embodiment, the polymer is PDMS.

In one embodiment, a reservoir is any container that can hold liquids. In one embodiment, a reservoir is a vessel. In one embodiment, the reservoir has a channel structure. In one embodiment, any reservoir of the invention or the buffer reservoir or the buffer channel is rounded. In one embodiment, the reservoir or the buffer channel has two ends. In one embodiment, different or equal voltages can be applied to the two ends of the reservoir or the buffer channel. In one embodiment, the reservoir is the buffer microchannel. In one embodiment, the buffer microchannel or the reservoir are grounded using one electrode. In one embodiment, the reservoir or the buffer channel are grounded using two or more electrodes. In one embodiment, any voltage can be applied to the buffer reservoir or to the buffer microchannel or to any reservoir of the invention using one or more electrodes.

In one embodiment a conduit has at least one nanometer dimension. In one embodiment, the conduit has a thickness ranging between 1 nm and 1000 nm. In one embodiment, the conduit has dimensions in the micron scale, but has pores in the nanometer scale. In one embodiment, nanometer-sized pores are permeable. In one embodiment, nanometer-sized pores are interconnected.

In one embodiment, an electric field is the space surrounding an electric charge. In one embodiment, the electric field exerts a force on other electrically charged objects. In one embodiment, a stationary charged particle in an electric field experiences a force proportional to its charge. In one embodiment, an electric field can be induced by applying a voltage.

In one embodiment, an electric field can be induced in the area between two electrodes to which an unequal voltage is applied. In one embodiment, certain distribution of positive or negative charges in space can give rise to an electric field.

In one embodiment, electroosmotic flow or electro-osmotic flow, often abbreviated EOF is the motion of ions in a solvent environment through very narrow channels, where an applied voltage across the channels causes the ion migration. In one embodiment, an ion depletion zone is a region in the solution that is depleted of ions.

In one embodiment, under the influence of a certain electric field, ions migrate away from the depletion zone. In one embodiment, the depletion zone contains no ions. In one embodiment, the depletion zone contains a very low concentration of ions. In one embodiment, the depletion zone contains less ions than the number of ions that were present in this zone prior to inducing the electric field. In one embodiment, the ion depletion zone in the sample microchannel, is the region proximal to the conduit. In one embodiment, the ion depletion zone comprises the interface between the sample microchannel and the conduit. In one embodiment, the ion depletion zone or the area proximal to the conduit is an area within the sample microchannel that is between 0-2 μm from the conduit. In one embodiment, the ion depletion zone or the area proximal to the conduit is an area within the sample microchannel that is between 0-25 μm from the conduit. In one embodiment, the ion depletion zone or the area proximal to the conduit is an area within the sample microchannel that is between 0-50 μm from the conduit. In one embodiment, the ion depletion zone or the area proximal to the conduit is an area within the sample microchannel that is between 0-100 μm from the conduit. In one embodiment, the ion depletion zone or the area proximal to the conduit is an area within the sample microchannel that is between 0-200 μm or 0-500 μm from the conduit. In one embodiment, the ion depletion zone or the area proximal to the conduit is an area within the sample microchannel that is between 0-1000 μm from the conduit. In one embodiment, the phrase "salt ions are confined to a region within said sample microchannel that is distant from said conduit" describes the region outside the ion-depletion zone. In one embodiment, the term "distant" reflects an area in the sample microchannel that the distance between it and the conduit is at least the length of the ion-depletion zone. In one embodiment, the ion-depletion zone is an area around the conduit from which ions are depleted, and the ions are depleted to areas more distant from the conduit. In one embodiment, the area to which the salt ions are confined is an area that dose not comprise the ion depletion zone. In one embodiment, the ion-depletion zone and the area where the salt ions are confined to, are complementary.

In one embodiment, desalting means "removing salt ions from". In one embodiment, depleting ions from the ion-depletion zone is equivalent to desalting this area.

In one embodiment, a "ground", "grounded" or "electrically grounded" are terms used to describe the relative voltage applied to one side of the microchannels, to one side of the conduits, or the relative voltage applied to regions or electrodes used in methods of this invention. In one embodiment, ground is the reference point in an electrical circuit from which other voltages are measured, a common return path for electric current (earth return or ground return), or a direct physical connection to the Earth. For measurement purposes, the earth or ground serves as a constant potential reference against which other potentials can be measured. In one embodiment, an electrical ground system serves as an adequate zero-voltage reference level.

In one embodiment, an external gate voltage is a voltage applied external to the microchannel or conduit of the invention, and not directly to the liquid carrying the charged species. In one embodiment, "gate" means that the application of such voltage can gate the liquid flow, by causing ions to move or to stop moving in a certain direction. In one embodiment, "gate" or "gating" means switching the direction of the flow, or switching the direction of migrating ions. In one embodiment, gating can stop flow. In one embodiment, gate voltage influences charged species by inducing an electric field. The electric field induced by the gate voltage may cause the accumulation, migration, depletion or a combination thereof of the charged species in or away from defined areas in the microfluidic channels.

In one embodiment, devices used in methods of this invention are made by lithography and etching processes. In one embodiment lithography and etching processes are the conventional processes used in the semiconductor fabrication industry.

In one embodiment, methods of this invention are used for desalting or for diminishing the salt concentration in a solution. In one embodiment, desalting or diminishing the salt concentration in a solution comprises the reduction in the number of salt ions in a certain volume of a solution. In one embodiment, desalting or diminishing the salt concentration of a solution comprises reducing the electrolyte strength of the solution.

In some embodiments, the devices of this invention comprise a conduit connecting between microchannels. In some embodiments, the term "conduit" may refer to a channel, a connector, a wire, a linkage, a solution-filled capillary, a porous material filled with fluid, an electrically conducting or semiconducting material. In one embodiment, a conduit is attached directly to the microchannels, or in one embodiment, via an adaptor, a filter, a junction or any other desired material, as will be appreciated by the skilled artisan. In some embodiments, the conduit is a junction between a sample microchannel and a buffer microchannel. In some embodiment, flow is induced in the conduit. In one embodiment, ion flow is permitted through the conduit. It is to be understood that any structuring of the device to accommodate a conduit is what is to be understood as encompassed by the phrase "a conduit linked to said sample microchannel and to said buffer microchannel or reservoir", and is part of the present invention.

In one embodiment, a conduit is a nanochannel. According to this aspect and in one embodiment, the conduit has at least one dimension ranging between 1 nm and 1000 nm. In one embodiment, the conduit comprising a polymer-based permselective material. In one embodiment, the polymer-based permselective material comprising a co-polymer of tetrafluorethylene and sulfonic acid. In one embodiment, the polymer-based permselective material comprising a cation-selective or an anion-selective material. In one embodiment, the conduit comprising an electrical junction that is preferentially conductive to positive ions or to negative ions.

In one embodiment, the buffer comprises a buffer solution. In one embodiment, a buffer solution is a solution that resists change in hydronium ion ($H^+$) and in hydroxide ion ($OH^-$) concentration. Therefore, a buffer solution resists a pH change. The buffer solution can resist a pH change upon addition of small amounts of acid or base, or upon dilution. Buffer solutions consist of a weak acid and its conjugate base or a weak base and its conjugate acid. In one embodiment, the buffer solution comprises a phosphate buffer. In one embodiment, the buffer solution comprises an acetate buffer, Tris buffer, PIPES or HEPES buffers.

In one embodiment, an electrical junction is any junction that can pass an electrical signal or a junction between two or more points to which voltage can be applied, or a junction that enables an electrical signal from one side to affect the electrical state of another side of the junction. In one embodiment, an electrical junction may connect two or more wires or channels or areas wherein at least two of the wires/channels/areas have non-zero electrical properties such as electric field, voltage, current, charge accumulation etc. In one embodiment, devices of this invention comprises electrical junction that are preferentially conductive to either positive or negative ions. In one embodiment, the electrical junctions can be made of any porous material. In one embodiment the porous material can be organic and in another embodiment inorganic. In one embodiment, an inorganic material may comprise alumina, silica or both. In one embodiment, the porous material comprises particles. In one embodiment, the organic material comprises polymers. In one embodiment, the porous material comprises di- or tri-block copolymers.

In one embodiment, μ defines "micro" or "micron" or "microns". In one embodiment, μ is used as a term for describing viscosity. In one embodiment, μm stands for micrometer(s) and in one embodiment μL stands for microliter. In one embodiment where μ is used to describe viscosity, the use of μ is apparent from the relevant phrase. In one embodiment the use of μ as viscosity is understood for a person of ordinary skill in the art.

In one embodiment, the term "membraneless" is used to describe a device wherein the water to be purified/desalinated, does not involve passage of such water through a membrane. "membraneless" desalination processes or systems of the present invention may involve the use of the membrane, but the water to be desalinated does not have to pass through the membrane in order to be desalinated. Membraneless may mean that according to processes of the present invention, water to be desalinated are passed next to a membrane or tangential to a membrane and undergo desalination without passing through the membrane. This is in contrast to some conventional filtration processes wherein salinated water are run through a membrane, the salt or other ions remain in the membrane or at the inlet of the membrane, and the water are emerging desalinated on the outlet of the membrane after passing through it.

In one embodiment, brackish water is water that has more salinity than fresh water, but not as much as seawater. In one embodiment, brackish water may result from mixing of seawater with fresh water as in estuaries or it may be found in aquifers.

In one embodiment, WHO is the world health organization. In one embodiment, RO means reverse osmosis. In one embodiment, ED means electro-dialysis. In one embodiment, ICP means ion concentration polarization.

In one embodiment, cp is a unit of viscosity. In one embodiment, cp means centipoise. In one embodiment, 1 p=1 g/(cm second) and 1000 cp=1 p.

II. Dimensions and Values

In one embodiment, a device of this invention may comprise a plurality of channels, including a plurality of microchannels, or a plurality of conduits, or a combination thereof. In one embodiment, the phrase "a plurality of channels refers to more than two channels, or, in another embodiment, more than 5, or, in other embodiments, more than 10, 96, 100, 384, 1,000, 1,536, 10,000, 100,000 or 1,000,000 channels.

In one embodiment, the width of the microchannel is between 1-100 μm, or in another embodiment, between 1 and 15 μm, or in another embodiment, between 20 and 50 μm, or in another embodiment, between 25 and 75 μm, or in another embodiment, between 50 and 100 μm. In one embodiment, the width of the microchannel is between 1-5 μm, or in another embodiment, between 10 and 20 μm, or in another embodiment, between 0.5 and 10 μm, or in another embodiment, between 10 and 99 μm, or in another embodiment, between 75 and 100 μm. In one embodiment, the depth of the microchannel is between 0.5-50 μm, or in another embodiment, between 0.5 and 5 μm, or in another embodiment, between 5 and 15 μm, or in another embodiment, between 10 and 25 μm, or in another embodiment, between 15 and 50 μm. In one embodiment, the depth of the microchannel is between 0.5-1.5 μm, or in another embodiment, between 1 and 9 μm, or in another embodiment, between 10 and 20 μm, or in another embodiment, between 10 and 50 μm, or in another embodiment, between 15 and 100 μm.

In another embodiment, the width of the conduit is between 1 μm-50 μm, or in another embodiment, between 1 and 15 μm, or in another embodiment, between 10 and 25 μm, or in another embodiment, between 15 and 40 μm, or in another embodiment, between 25 and 50 μm. In another embodiment, the width of the conduit is between 1 μm-10 μm, or in another embodiment, between 0.1 and 1 μm, or in another embodiment, between 0.5 and 5 μm, or in another embodiment, between 0.01 and 0.1 μm, or in another embodiment, between 25 and 99 μm. In another embodiment, the depth of said conduit is between 20-100 nanometers, or in another embodiment, between 20 and 50 nanometers, or in another embodiment, between 20 and 75 nanometers, or in another embodiment, between 30 and 75 nanometers or in another embodiment, between 50 and 100 nanometers. In another embodiment, the depth of said conduit is between 1-5 μm, or in another embodiment, between 0.1 and 1 μm, or in another embodiment, between 0.01 and 0.1 μm, or in another embodiment, between 10 and 75 μm or in another embodiment, between 25 and 100

In one embodiment, the device comprises multiple sample microchannels, multiple buffer microchannels multiple conduits or a combination thereof wherein the multiple channels are arranged in an array or with a particular geometry.

In one embodiment, the conduits are perpendicularly oriented with respect to at least one of the first or buffer microchannels. In one embodiment, the conduits are oriented in an angle that is different from 90 degrees. In one embodiment, at east one of the conduit, at least one of the first or buffer microchannels or a combination thereof are linear. In another embodiment, at least one of the conduits, at least one of the first or buffer microchannels or a portion or a combination thereof are curved. In one embodiment, multiple channel arrays are placed one on top of the other in a device. In one embodiment, such design is referred to as a 3-D design. In one embodiment, the microfluidic device comprising arrays of channels comprises a three-dimensional array structure, and in another embodiment, the microfluidic device comprising arrays of channels comprises a two-dimensional structure. In one embodiment, two-dimensional structure is a structure wherein the majority or all of the channels are arranged in one plane. In one embodiment, two-dimensional structure is a structure wherein the majority or all of the channels are constructed on or in the same surface. In one embodiment, three-dimensional structure is obtained by placing several substrates, several surfaces or several two-dimensional devices one on top of the other. In another embodiment, the three-dimensional structure is constructed on or in one piece of substrate by e.g. lithography, etching and deposition methods.

In one embodiment, the number of arrays in a device is 1. In one embodiment, the number of arrays in a device is 1-10. In one embodiment, the number of arrays in a device is 10-100. In one embodiment, the number of arrays in a device is 10-1000. In one embodiment, the number of arrays in a device is 1-50. In one embodiment, the number of arrays in a device is 50-100. In one embodiment, the number of arrays in a device is 1000-10000. In one embodiment, the number of arrays in a device is 10000-1000000.

In one embodiment, the device length, width, height or a combination thereof ranges between 10 cm-30 cm. In one embodiment, the device length, width, height or a combination thereof ranges between 1 cm and 10 cm. In one embodiment, the device length, width, height or a combination thereof ranges between 25 cm-50 cm. In one embodiment, the device length, width, height or a combination thereof ranges between 50 cm-100 cm. In one embodiment, the device length, width, height or a combination thereof ranges between 0.1 cm and 1 cm. In one embodiment, the device length, width, height or a combination thereof ranges between 1 cm and 5 cm.

III. Embodiments of Device Description and Methods of Operation

In one embodiment, the device used in embodiments of this invention is constructed as diagrammed in FIG. 1. The sample microchannel (1-10) is the channel through which a sample comprising charged species can be made to pass. The sample microchannel has a first side which is the left side of the sample microchannel shown in FIG. 1. The sample microchannel has a second side which is the right side of the sample microchannel shown in FIG. 1. The first side (left) of the sample microchannel is connected to at least one sample reservoir. In one embodiment, the sample reservoir is connected to the sample microchannel by means of a conduit, which may have the dimensions of the microchannel, or may have different dimensions. In one embodiment, the sample reservoir is capable of releasing a fluid or liquid comprising a species of interest or charged species into the sample microchannel from the first side. In one embodiment, fluid or liquid entering the microchannel has an initial flow direction from the left to the right side of the microchannel shown in FIG. 1.

In one embodiment, at least one buffer microchannel or reservoir (1-20) is placed in the vicinity or proximal to the sample microchannel. In on embodiment, the buffer microchannel or reservoir is filled with buffer.

In one embodiment, at least one conduit (1-30) is linked to the sample microchannel (1-10) and to the at least one buffer microchannel (1-20).

In one embodiment, the conduit is made of flat nanofluidic filters filled with buffer solution. In one embodiment, the nanofluidic filters serve as an ion-selective membrane allowing selected ions to pass from one area to another within the conduit. In one embodiment, movement or migration of ions within the conduit is a result of an electric field induced in the conduit. In one embodiment, the movement or migration of ions within the conduit, changes or controls the magnitude of an electric field in the vicinity of the conduit.

In one embodiment, when an electric field is induced in the conduit, it affects a region in the sample microchannel that is proximal to the conduit. In one embodiment, such electric field, generates a depletion zone in the sample microchannel that is proximal to the conduit. In one embodiment, the depletion zone is a region depleted of charged species. In one embodiment, charged species are pushed away from the ion depletion zone. In one embodiment, the effect of the electric filed in the conduit is to reduce the concentration of ions or charged species in the area proximal to the conduit, by forcing the charged species away from the conduit area. In one embodiment, the ion depletion zone and the desalted zone shown in FIG. 1, represent the region in the sample microchannel that has a lower concentration of charged species as compared to the dark region on the left side of the sample microchannel in which charged species or ions accumulate. This process is a result of the electric field induced in the conduit. In one embodiment, the ion depletion zone or the desalted zone has no charged species. In one embodiment, the ion depletion zone or the desalted zone has a low concentration of charged species. In one embodiment, the ion depletion zone or the desalted zone has charged species concentration that is lower than the charged species concentration in the non-depleted or non desalted area or areas of the sample microchannel. In one embodiment, the electric field induced in the conduit is denoted $E_N$ as shown in FIG. 1.

In one embodiment, induction of the electric field $E_N$ in the conduit, induces the concentration of the charged species of interest within one region of the sample microchannel, while depleting it from another region of the sample microchannel.

In one embodiment, fluid flow in the microchannel from the first side (left in FIG. 1) to the second side (right side in FIG. 1) is pressure driven. In another embodiment, fluid flow from the first to the second side of the sample microchannel is induced by an electric field. In one embodiment, such electric field induced in the microchannel is denoted $E_T$. In one embodiment, $E_T$ is induced as a result of a potential difference between the first and the second side of the sample microchannel. In one embodiment, the potential difference is achieved by applying a higher voltage to the first side of the microchannel and a lower voltage to the second side of the first conduit. In one embodiment, the higher voltage is denoted $V_H$ and the lower voltage is denoted V. In one embodiment, $V_H$ is 60 V and $V_L$ is 40 V.

In one embodiment, the flow is a result of pressure and electric field applied to the sample microchannel.

In one embodiment, the generation of the depletion region by $E_N$, causes and accelerated fluid flow from the left side to the right side or from the first side to the second side of the sample microchannel. In one embodiment, $E_N$ can be used to accelerate the fluid flow from the right side to the left side or from the second side to the first side of the sample microchannel. In one embodiment, $E_N$ depend on its magnitude can cause a flow to stop or can cause reversal or switching of flow direction.

In one embodiment, the method generates a depletion region and an accelerated liquid flow within the sample microchannel efficiently because of a nonlinear electroosmotic flow (much stronger than normal electroosmotic flow) generated in the microchannel, which draws fluid into the microchannel from the sample reservoir with high flow speed, and because an energy barrier for anionic molecules is generated by the induced space charge layer in the microchannel, at regions of apposition to the conduits.

In one embodiment, the two separate electric fields $E_N$ and $E_T$ are applied to the device, as shown in FIG. 1. The field in the nanofluidic channel ($E_N$) generates an ion-depletion region (colored white area within sample microchannel in FIG. 1) and extended space charge layer that traps charged species. The tangential field in the microfluidic channel ($E_T$), generates electroosmotic flow, which draws charged species into the trapped region (colored with dark gradient within sample microchannel in FIG. 1) from the reservoir.

In one embodiment, the space charge region is further stabilized by manipulating buffer conditions in the devices of the invention. In one embodiment, the device comprises two or a series of two buffer microchannels, each connected by a conduit to the sample microchannel. According to this embodiment, over a course of time, ion depletion in the sample microchannel leads to ion enrichment in the buffer microchannel, thus the buffer concentration in the second microfluidic channel increases with prolonged conduction of the species separation process. By providing a lower concentration buffer, at prescribed time periods, in one embodiment, or continually, in another embodiment, by electroosmosis, or in another embodiment, by pressure driven flow, in the buffer microchannel, this effect is mitigated, according to this embodiment.

In another embodiment of the invention, confinement of charged species to regions in the sample microchannel may be enhanced by positioning nanofluidic channels on both sides of the sample microchannel and in fluid communication with the sample and buffer microchannels as shown, for example, in FIG. 1. Ion depletion initiation at the interface between the sample microchannel and the conduit, is enhanced by positioning the conduits on either side of the sample microchannel, and in some embodiments, a more stable space charge region is produced.

In one embodiment, the electric field induced in the conduit is a result of the voltages applied to the sample and buffer microchannels. In one embodiment, the voltages applied to the sample microchannel are $V_H=60\,V$ and $V_L=40V$. The two buffer microchannels are grounded on both ends as shown in FIG. 1. The voltage difference between the conduit side that is linked to the sample microchannel and the conduit side that is linked to the buffer microchannel is the result of the higher voltages applied to the sample microchannel with respect to the buffer microchannel. This voltage difference on the conduit generates the electric field in the conduit that in turn, generates the ion-depletion zone in the sample microchannel.

In one embodiment, the flow may be pressure-driven, and may be accomplished by any means well known to one skilled in the art. In another embodiment, the flow may be a hybrid of pressure-driven and electro osmotic or electrokinetic flow.

In one embodiment, the phrases "pressure-driven flow" refers to flow that is driven by a pressure source external to the channel segment through which such flow is driven, as contrasted to flow that is generated through the channel segment in question by the application of an electric field through that channel segment, which is referred to herein, in one embodiment, as "electrokinetically driven flow."

Examples of pressure sources include negative and positive pressure sources or pumps external to the channel segment in question, including electrokinetic pressure pumps, e.g., pumps that generate pressure by electrokinetically driven flow in a pumping channel that is separate from the channel segment in question, provided such pumps are external to the channel segment in question (see U.S. Pat. Nos. 6,012,902 and 6,171,067, incorporated herein by reference in their entirety).

In one embodiment, the term "electrokinetic flow" refers to the movement of fluid or fluid borne material under an applied electric field. Electrokinetic flow generally encompasses one or both of electrophoresis, e.g., the movement of charged species through the medium or fluid in which it is disposed, as well as electroosmosis, e.g., the electrically driven movement of the bulk fluid, including all of its components. Accordingly, when referred to in terms of electrokinetic flow, it will be appreciated that what is envisioned is the full spectrum of electrokinetic flow from predominantly or substantially completely electrophoretic movement of species, to predominantly electroosmotically driven movement of material, e.g., in the case of uncharged material, and all of the ranges and ratios of the two types of electrokinetic movement that fall between these extremes.

In one embodiment, reference to the term "liquid flow" may encompass any or all of the characteristics of flow of fluid or other material through a passage, conduit, or channel or across a surface. Such characteristics include without limitation the flow rate, flow volume, the conformation and accompanying dispersion profile of the flowing fluid or other material, as well as other more generalized characteristics of flow, e.g., laminar flow, creeping flow, turbulent flow, etc.

In one embodiment, hybrid flow may comprise pressure-based relay of the liquid sample into the channel network, followed by electrokinetic movement of materials, or in another embodiment, electrokinetic movement of the liquid followed by pressure-driven flow.

In one embodiment, the electric field may be induced in the respective channels by applying voltage from a voltage supply to the device. In one embodiment voltage is applied by way of the placement of at least one pair of electrodes capable of applying an electric field across at least some of the channels in at least one direction. Electrode metal contacts can be integrated using standard fabrication technology to be in contact with at least one sample or buffer microchannel, or in another embodiment, at least one conduit, or in another embodiment, a combination thereof, and oriented as such, to establish a directional electric field. Alternating current (AC), direct current (DC), or both types of fields can be applied. The electrodes can be made of almost any metal, and in one embodiment, comprise thin Al/Au metal layers deposited on defined line paths. In one embodiment, at least one end of one electrode is in contact with buffer solution in the reservoir.

In one embodiments, portions of the electrodes are made of any conducting material. In on embodiment, electrodes are made of metals, doped semiconductors, or conducting organic materials. In one embodiment, electrodes are made of a combination of materials. In one embodiment, electrodes are made of gold, carbon, glassy carbon, pyrolytic carbon, Al, Cu, Pd, Pt, Ag, or a combination thereof. In one embodiment the electrode comprises mercury. In one embodiment, the electrodes comprise solutions of salts. In one embodiment at least one electrode is a silver/silver chloride electrode (Ag/AgCl). In one embodiment at least one electrode is a saturated calomel electrode (SCE), a normal hydrogen electrode (NHE) also known as a standard hydrogen electrode (SHE), a copper-copper(II) sulfate electrode or a combination thereof. In one embodiment, at least one electrode is a microelectrode or an ultramicroelectrode. In one embodiment, a plurality of microelectrodes are used. In one embodiment, at least one electrode is fabricated as part of the substrate. According to this aspect and in one embodiment, at least one electrode is constructed in, on, parallel to, perpendicular to the substrate from which the device is made. In one embodiment, the device is sealed or covered by a flat or curved surface. In one embodiment, at least one electrode is embedded in or fabricated into or onto the cover or sealed material such that at least a portion of the electrode interfaces with the sample or buffer micro channels or with the conduit/s or with a combination thereof.

In another embodiment, methods of this invention utilize at least two pairs of electrodes. In one embodiment, additional electrical contacts can be used to independently modulate the direction and amplitudes of the electric fields to, in one embodiment, orient the space charge layer, or in another embodiment, move macromolecules at desired speed or direction, or in another embodiment, a combination thereof.

In one embodiment, the voltage applied to any of the electrodes is between 50 mV and 500V. In one embodiment, the voltage applied to any of the electrodes is between 50 V and 500 V. In one embodiment, the voltage applied to any of the electrodes is between 10 mV and 100 V. In one embodiment, the voltage applied to any of the electrodes is between 1 V and 30 V. In one embodiment, the voltage applied to any of the electrodes is between 10 V and 40 V. In one embodiment, at least one electrode is not connected and referred to as a "floating" electrode. In one embodiment, at least one electrode is grounded. In one embodiment, instead of having a "floating" electrode that is not connected to an electrical circuit, the position in the microchannel that needs to "floated" is not connected to an electrode.

In one embodiment, the voltage supply may be any electrical source, which may be used to provide the desired voltage. The electrical source may be any source of electricity capable of generating the desired voltage. For example, the electrical source may be a piezoelectrical source, a battery, or a device powered by household current. In one embodiment, a piezoelectrical discharge from a gas igniter may be used.

In one embodiment, the electrokinetic trapping of charged species in the device and sample collection can occur over a course of minutes, or in another embodiment, can be maintained for several hours. In one embodiment, depletion of a species from one region and its accumulation in another region over a course of time results in species concentration factors as high as $10^6$-$10^8$, and in another embodiment, may be even higher, upon optimization of the conditions employed during the concentration, such as by modifying the interface between the microchannel and conduit, voltage applied, additional gate voltages applied, salt concentration of the liquid, pH of the liquid, number, size and geometry of the conduits, geometry of the sample microchannel or combination thereof.

In another embodiment, methods of this invention further comprises at least one waste reservoir in fluid communication with the sample microchannel or microchannels, the buffer microchannel or microchannels, or the conduit or conduits of the microfluidic device. In one embodiment, the waste reservoir is capable of receiving a fluid.

In one embodiment, instead of or in addition to the waste reservoir, a collection reservoir is connected to the sample microchannel in order to collect species of interest, ions, desalted solution, pure liquid or a combination thereof. In on embodiment, the collection reservoir is connected to the second side of the sample microchannel and in another embodiment the collection reservoir is connected to the first side of the sample microchannel. According to this aspect of the invention and in one embodiment, connecting the collection reservoir to the first side of the sample microchannel is advantageous in cases where liquid flow is reversed or switched or stopped, and species or liquids can be collected at the first side of the sample microchannel.

In another embodiment, the device, or in another embodiment, the microchannel or microchannels are capable of being imaged. Imaging of the device, or parts thereof, may be accomplished by presenting it to a suitable apparatus for the collection of emitted signals, such as, in some embodiments, optical elements for the collection of light from the microchannels.

In one embodiment, the device may be disposable, and in another embodiment, may be individually packaged, and in another embodiment, have a sample loading capacity of 1-50,000 individual fluid samples. In one embodiment, the device can be encased in a suitable housing, such as plastic, to provide a convenient and commercially-ready cartridge or cassette. In one embodiment, the device of this invention will have suitable features on or in the housing for inserting, guiding, and aligning the device, such that, for example, a sample loading compartment is aligned with a reservoir in another device, which is to be coupled to the device of this invention. For example, the device of this invention may be equipped with insertion slots, tracks, or a combination thereof, or other adaptations for automation of the concentration process via a device of this invention.

The device may be so adapted, in one embodiment, for high throughput manipulation of multiple samples, such as will be useful in desalting and analysis applications, as will be appreciated by one skilled in the art.

In one embodiment of the present invention, the device of this invention is a part of a larger system, which includes an apparatus to excite species inside the channels and detect and collect the resulting signals. In one embodiment, a laser beam may be focused upon the sample species concentration region, using a focusing lens, in another embodiment. The generated light signal from the species inside the microchannels may be collected by focusing/collection lens, and, in another embodiment, reflected off a dichroic mirror/band pass filter into optical path, which may, in another embodiment, be fed into a CCD (charge coupled device) camera.

In another embodiment, an exciting light source could be passed through a dichroic mirror/band pass filter box and focusing/collecting scheme from the top of the device of this invention. Various optical components and devices can also be used in the system to detect optical signals, such as digital cameras, PMTs (photomultiplier tubes), and APDs (Avalanche photodiodes).

In another embodiment, the system may further include a data processor. In one embodiment, the data processor can be used to process the signals from a CCD, to a digital image of the concentrated species onto a display. In one embodiment, the data processor can also analyze the digital image to provide characterization information, such as size statistics, histograms, karyotypes, mapping, diagnostic information and display the information in suitable form for data readout.

In one embodiment, the liquid comprises charged or uncharged species or a combination thereof. In one embodiment, the liquid comprises, ions, complex ions, neutral molecules, charged molecules, cluster of atoms, clusters of particles, beads, nanospheres, biological molecules or fragments thereof, amino acids, peptides, proteins, protein complexes, enzymes, DNA, vectors, RNA, nucleotides, lipids, phospholipids, cholesterol, mono-, di-, oligo-, or poly-saccharides, organic or inorganic salts, NaCl, KCl, KI, NaI, Ca containing salts, H+ ions, ammonium ions, nitrates, sulfates, acids bases, strong electrolytes, weak electrolytes, or non electrolytes.

In certain embodiments of the present invention, the methods may utilize an apparatus for transporting solutions or pure liquids from the microchannels into the waste reservoirs.

In one embodiment, this invention provides an array architecture that is capable of being scaled to at least 10,000 devices, suitable for a real-world applications.

In one embodiment, fluid speed, desalting and pumping efficiency may be determined by using labeled proteins or polypeptides or fluorescent markers, introduced into the microchannels or reservoirs in known ratios and detecting the concentration of labeled protein or polypeptides, or fluorescent markers using any detection technique know in the art such as UV/Vis or IR spectroscopy or fluorescence. Signal intensity can be determined as a function of time, over background noise.

In one embodiment, devices used in the methods of this invention may be under controlled physicochemical parameters, which may comprise temperature, pH, salt concentration, or a combination thereof.

In one embodiment, the conduit is made of a perm selective material. In one embodiment, the conduit is filled with fluid. In one embodiment, the conduit is permeable to one type of ions and is not permeable to another type of ions. In one embodiment, the conduit is a structure permeable to $H^+$ ions. In one embodiment, the conduit may be made of a charged gel or random nanoporous material, wherein charged group are embedded in the nanoporous material. In one embodiment, according to this aspect of the invention, the charged gel or nanoporous material may have a similar pore size. According to this aspect of the invention, a space charge layer may be generated in the charged gel or random nanoporous material, similar to that formed in the conduit as described and exemplified herein, wherein an electric field is induced in the nanoporous charged gel or charged material, similar to that induced in the conduit.

In one embodiment, this invention provides a microfluidic pump comprising a device of this invention, which in one embodiment has a liquid flow speed of between 10 □m/sec and 10 mm/sec.

In one embodiment, within the thin nanofluidic channel, perm-selective portion of ion currents, caused by the counter ions within the Debye layer cannot be ignored, compared with the total ion current through the conduit, therefore, more counter ions (from the Debye layer) than co-ions migrate across the conduit when an electric field is applied resulting in a net transfer of charges (counter ions) from the anodic side to the cathodic side, and a concentration polarization effect. According to this aspect of the invention, ion depletion near the nanofluidic channel thickens the Debye layer, causing its overlap more significantly in the nanofluidic channel, speeding up the concentration polarization effect, and above a certain threshold En value, results in electroosmosis with second order kinetics.

According to this aspect of the invention, counter ion depletion from the nanofluidic channel, and creation of an extended space charge layer in bulk solution within the sample microchannel prevents co-ion migration in this region. In one embodiment, controlling the electric fields ($E_N$ and $E_T$), to balance the two forces (anion repulsion from the space charge layer vs. nonlinear electroosmotic flow from the reservoir), stabilizes the interface, which is where anionic species of interest are trapped and collected, according to this aspect of the invention.

In one embodiment, the liquid is a solution. In another embodiment, the liquid is a suspension, which, in another embodiment is an organ homogenate, cell extract or blood sample. In one embodiment, the species of interest comprises proteins, polypeptides, nucleic acids, viral particles, or combinations thereof. In one embodiment, the species of interest is a protein, nucleic acid, virus or viral particle found in, or secreted from a cell, and in another embodiment, is found in very low quantities, such that it represents less than 10% of the protein extracted form a protein extract of the cell.

Conduits thinner than 50 nm demonstrate unique ion-perm-selectivity at moderate ionic strength, due to the fact that the debye layer thickness is non-negligible compared with the channel thickness in these conduits. Often these phenomena are explained as Debye layer overlap, with the ratio between (equilibrium) Debye length and the channel dimension as the critical parameter. Typical ion behavior is such that the anodic side of the conduit is almost completely depleted from ionic species, while ion enrichment occurs in the cathodic side of the conduit, in some embodiments, attributable to the permselective nature of the conduits at low-ionic strength conditions, caused by the Debye layer overlap in the conduits. According to this aspect of the invention, due to this concentration gradient, preferential cation transport through the conduit is satisfied across the entire system, while maintaining net zero anion flux at the cathodic side.

According to this aspect of the invention, and in one embodiment, typically in the perm-selective membrane facing the bulk solution, there exists a diffusion layer outside of which convective mixing eliminates any concentration gradient, rendering the ion concentration comparable to that of bulk solution. In some embodiments, when the device operation is with a fixed diffusion length and increasing DC bias, the system responds by decreasing the local ion concentration on the anodic side of the membrane or the conduit. While it would be predicted that when this happens the system reaches a limiting current, above which no further increase in ion current is possible even with higher voltage applied to the system, surprisingly, it was found herein that significant over-limiting current can be observed in most perm-selective membranes, and in this case, the electrokinetic response may be amplified because of significantly lowered ion concentration near the conduit, therefore higher "local" zeta potential.

In some embodiments, the methods of this invention result in the acceleration of liquid flow in a microchannel. In one embodiment, the methods of this invention result in controlling liquid flow in a microchannel.

Figure 1B:
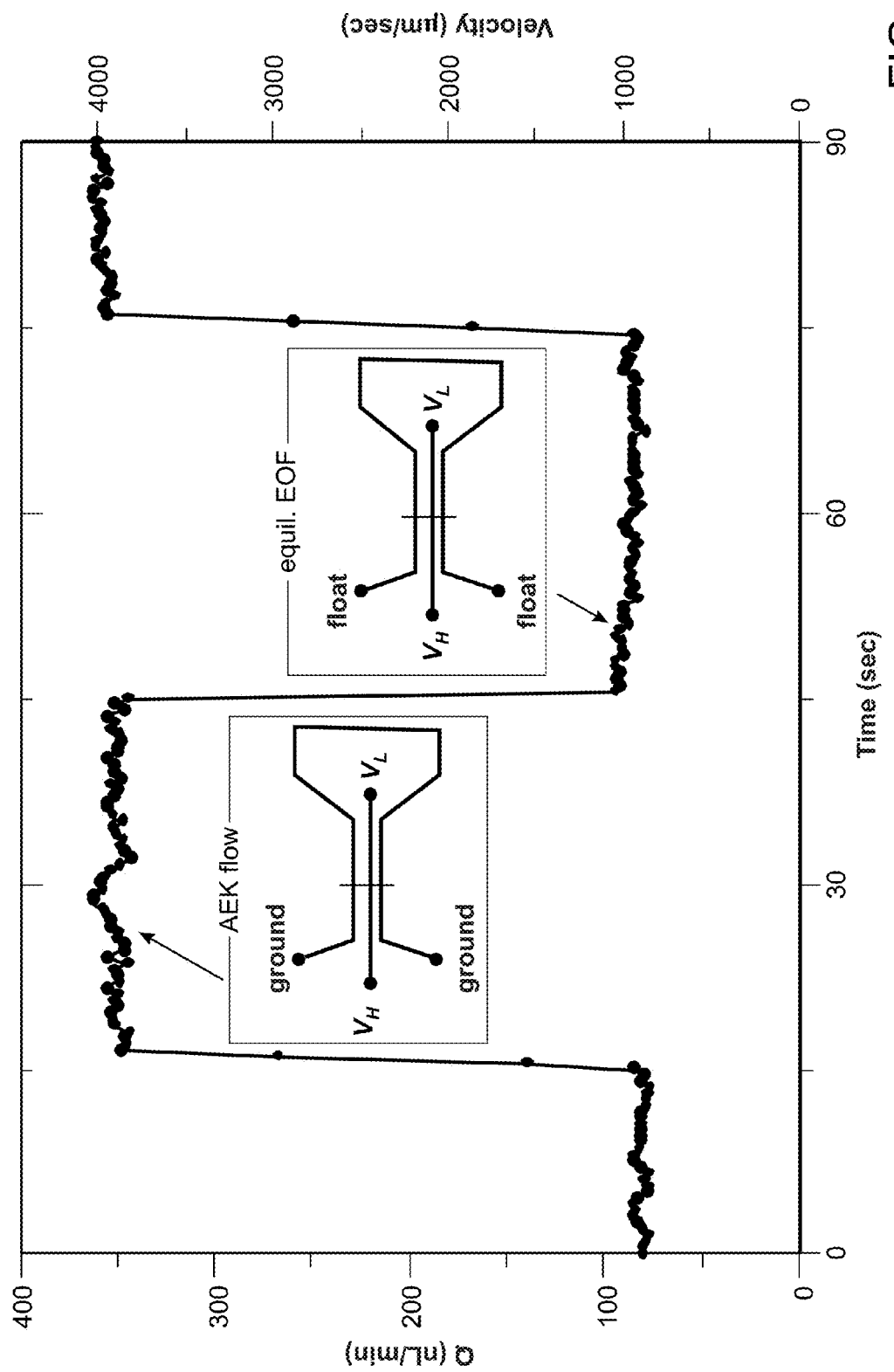
Figure 1C:
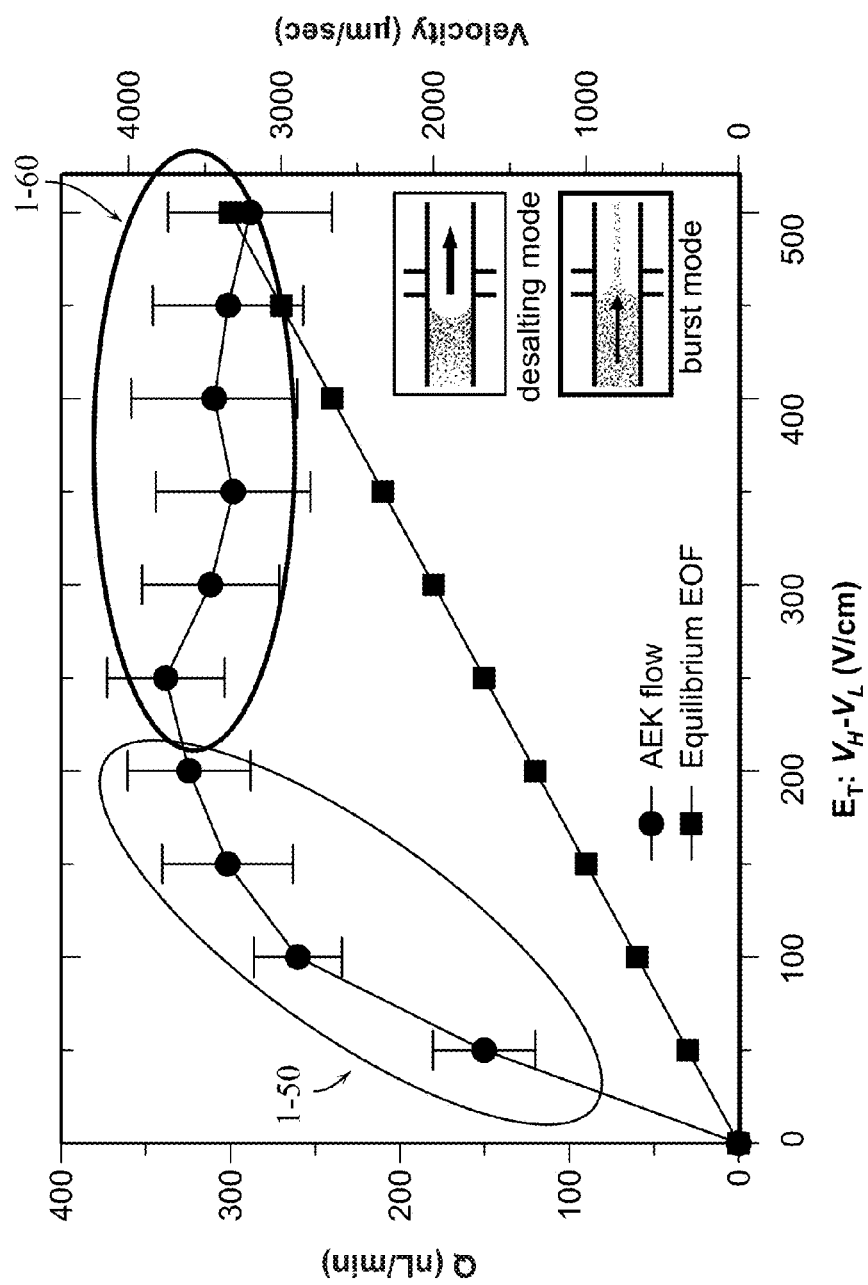

FIG. 1 is an embodiment of a method of the present invention wherein liquid flow is accelerated. As depicted in FIG. 1(a), the concentration polarization was initiated in the sample microchannel and the ionic concentration in anodic side (left side of microchannel) started to deplete (ion depletion zone) as a result of the normal electric field ($E_N$) through conduit. With aiding of the tangential electric field ($E_T$), charged species accumulated and formed the preconcentrated plug (gradient dark area within sample microchannel). In the meantime, the remaining microchannel was largely desalted and the ionic concentration went to that of nearly DI water. Because of the conductivity difference between the buffer zone and desalted zone, the electric field inside the ion depletion zone was greatly amplified and caused a strong electrokinetic flow. The volumetric flow rates with the amplified electrokinetic (AEK) flow were 5 times larger than that with the equilibrium EOF (no $E_N$ applied) as shown in FIG. 1(b). The switching between two flow modes (equilibrium EOF and AEK) took less than 1.5 seconds, which is a speed adequate for many applications of amplified electrokinetic pumps. The enhancement of the flow rate under the $E_N$ field is also depicted in FIG. 1(c) as a function of the voltage difference between the two ends of the sample microchannel. It was shown that for all voltage differences ($V_H$-$V_L$) up to 500 V (V per cm is plotted), the AEK flow rate was higher than the equilibrium EOF rate.

Controlling liquid flow has numerous applications in a wide range of fields, as will be appreciated by one skilled in the art. In one embodiment, the methods of controlling liquid flow, and/or the methods of concentrating a species of interest may be useful in biosensor devices. In one embodiment, control of liquid flow is essential in biosensors, wherein flow and mixing of a sample and various reactants to and from reservoirs in a microfluidic system is required. In another embodiment, concentration of a minute quantity of a species of interest for detection is a critical element of a biosensor device. In one embodiment, such methods are particularly useful in detecting organisms in a latent or spore state, wherein detection of the organism is otherwise difficult.

In other embodiments, various applications of the methods of the present invention are possible without deviating from the present invention. For the method of controlling fluid flow, for example, multiple microchannels may be so deposited such that fluid flow is directed to a central reservoir, to which additional microchannels may be connected. According to this aspect, the fluid once within the reservoir may then be mixed, and in turn, be pumped through the second set of microchannels to another reservoir connected thereto, for further manipulation. It can be appreciated that the pumping method of the present invention works with various types of fluids including water and biological fluids.

By way of example, the concentrating and pumping methods of the present invention allow for high-throughput robotic assaying systems to directly interface with the devices of the present invention, and to concentrate a species of interest, and/or pump liquid.

In some embodiments, the methods of this invention result in fast pumping of a liquid. In one embodiment, this invention provides a microfluidic pump comprising a device of this invention, which in one embodiment has a liquid flow speed of between 10 □m/sec and 10 mm/sec.

In some embodiments, the devices of this invention and methods of utilizing same result in the desalting of desired solutions. In some embodiments, desalting refers to decreasing the salt concentration by an order of magnitude. In some embodiments, desalting refers to reduction of salt in a solution from millimolar to micromolar scale, in some embodiments, or from micromolar to nanomolar scale, in other embodiments. In some embodiments, desalting refers to reduction of salt in a solution from a high millimolar concentration to a low millimolar concentration. In one embodiment, desalting refers to reduction of salt in a solution from 1 mM to less than 1 mM. In some embodiments, desalted solutions may be reapplied to the devices of this invention to further reduce salt concentrations in the solution.

In one embodiment, desalting can proceed in two modes depending on the voltage difference between the two sides of the sample microchannel. The amplified electrokinetic pumping can be operated in two different modes, depending on $E_T$ ($V_H$–$V_L$) as shown in FIG. 1(c): In 'desalting' mode 1-50, depletion zone and the ion concentration plug is maintained, which makes the pumped flow downstream become desalted. In the 'burst' mode (with higher tangential field) 1-60, the ion depletion zone is disrupted and the ions and other solutes contained in the solution are released, maintaining the downstream ionic strength and biomolecule contents of the pumped flow. In the burst mode 1-60, the velocities were saturated, but still higher than equilibrium EOF. The desalting mode 1-50 might be useful for certain actuation and analytical steps, while the burst mode 1-60 is more adequate for pumping biological fluids (such as cell culture media) in general microfluidic systems. The transition point between burst 1-60 and desalting 1-50 modes is expected to be determined by the convection near the nano-junction (i.e. the link port between the conduit and the sample microchannel), which is potentially controlled by careful design of the micro-nano junctions. As shown in FIG. 1(c), the volumetric (volume per time) flow rate and the velocity of the flow (.mu.m/sec) are higher when AEK is induced by the conduits.

Figure 2A:
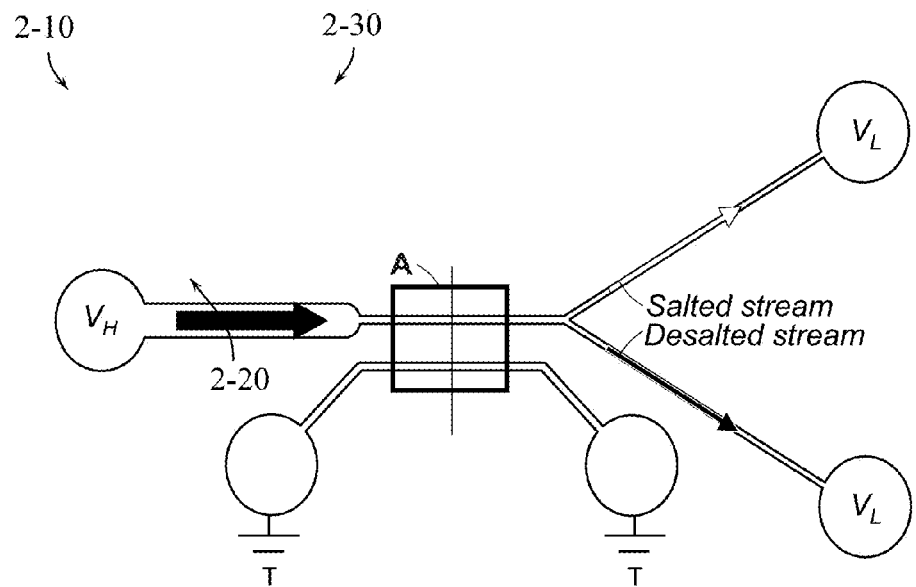
FIG. 2 schematically depicts embodiments of a device for desalting a liquid. A schematic diagram of micro/nanofluidic desalting system on (a) single-side and (b) dual-side conduit devices. (c) the experimental verification of particle motions in singe-side desalting device. Applied voltage is $V_H$=60V and $V_L$=40V.
Figure 2A:
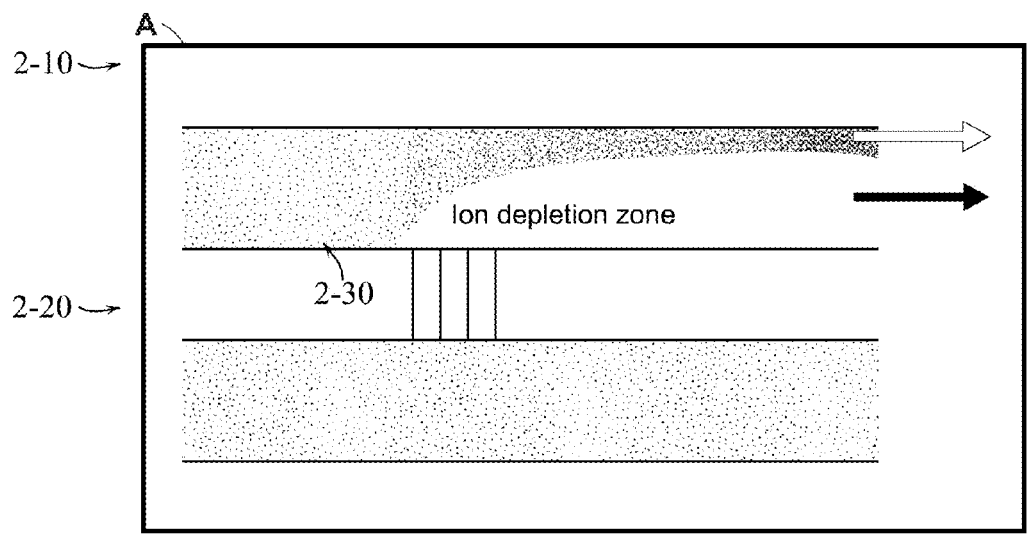
Figure 2B:
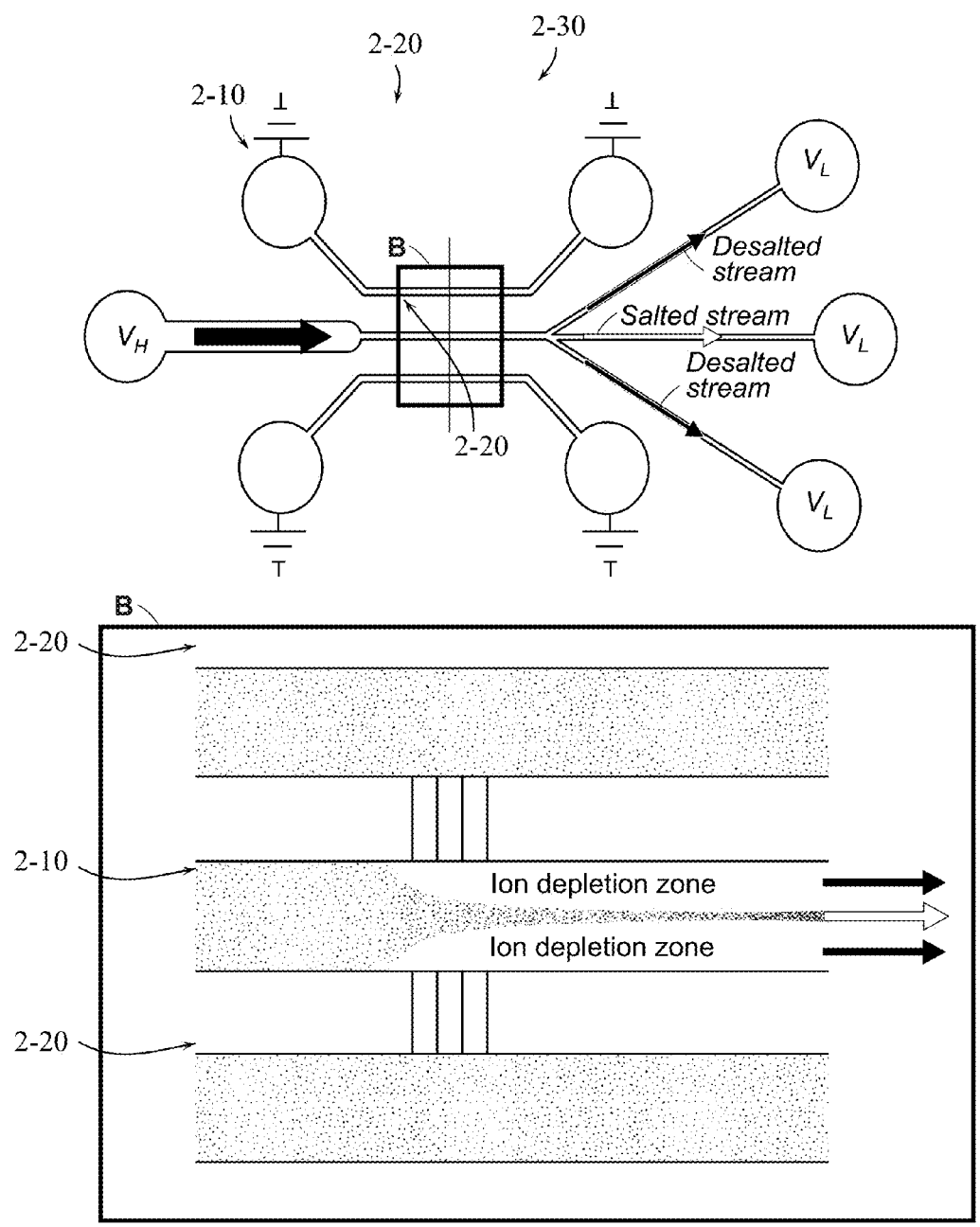

As shown in FIGS. 2(a) and 2(b), the sample desalting using the bursting mode can be realized in both single-side and dual-side conduit devices. FIG. 2(a) represent an embodiment in which a single side conduit(s) is/are employed. Sample channel 2-10 has an inlet for sample fluid on the left. The sample microchannel 2-10 is coupled to the buffer channel or reservoir 2-20, by a series of conduits 2-30. $V_H$ is applied to the first side (left side) of the sample microchannel while $V_L$ is applied to the two branches of the sample microchannel formed at the outlet or at the second or right side of the sample microchannel. These two voltages ($V_H$ and $V_L$) generate an EOF flow in the channel from left to right, or from the first side to the second side of the microchannel. When the buffer microchannel 2-20 is electrically grounded, a potential difference is formed over the conduits 2-30. This will create the ion depletion zone proximal to the conduits as depicted in the inset A which is a magnification of the central part of FIG. 1(a) including the conduit. As can be seen from the inset, the ion depletion zone which is a desalted stream, occupy the lower part of the sample microchannel. The ion-enriched zone which is the salted stream occupies the upper part of the sample microchannel. By connecting two channels to the outlet of the sample microchannel or by branching the microchannel to lower and upper branches through which the liquid can be made to pass, the desalted fluid can be separated from the salt enriched fluid, and later collected or subsequently used. In FIG. 1, the desalted stream is the stream wherein no ions or a low concentration of ion exist and the salted stream is the stream wherein the high concentration of ions or all of the sample ions exist. FIG. 2(b) is an embodiment of a dual side conduit device, wherein the conduit or conduits 2-30 are linked to the sample microchannel 2-10 on both sides. The conduits 2-30 are linked to the two buffer channels 2-20 on the other end of the conduits. Such configuration generates two depletion zones within the sample microchannel as shown in the inset B of FIG. 2(b). According to this aspect and in one embodiment, two desalted streams are collected on the right side, on the second side or the outlet of the sample microchannel. One from the upper part and one from the lower part of the microchannel. A central salted stream is collected by a third outlet or a third microchannel or a third branch that is connected to the central part of the sample microchannel. The connections of the outlet branches can be designed in various ways depending on the cross section of the sample microchannel. For example, if the sample microchannel cross section is rectangular, the cross section of the outlet branches can be rectangular or square.

Figure 2C:
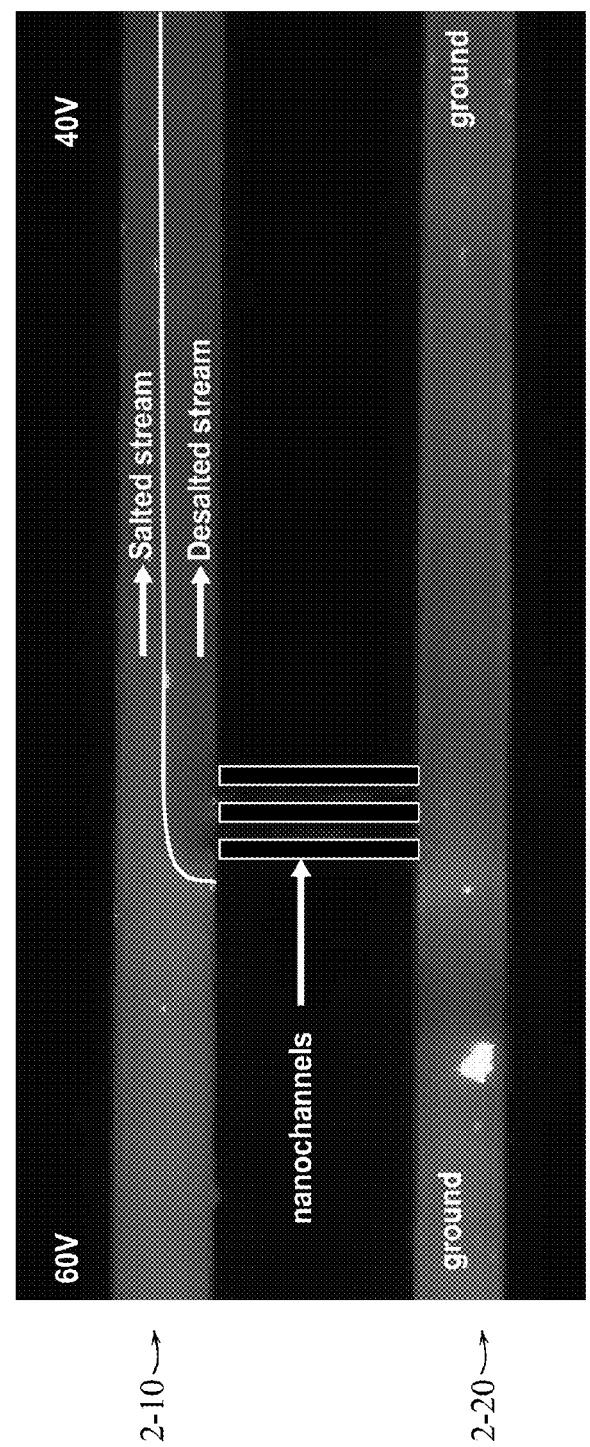

The desalted sample should be collected along the "desalted stream," while the injected sample which contains the ions or salt is collected from the salted stream (FIG. 2(c)). Experimental verification of the desalting concept was shown in FIG. 2(c). FIG. 2(c) is a microscope image showing the desalting device in action. Charged particles, which represent the salt, were injected from a left reservoir into the sample microchannel 2-10 and changed its path toward the upper sample microchannel wall right after crossing the conduit region. Along the desalted stream, no particle can exist due to the strong depletion force from the conduit. In this experiment $V_H$ was 60 V, $V_L$ was 40 V and the two ends of the buffer microchannel (2-20) were electrically grounded.

In one embodiment, the desalting process can be accomplished in a microchip setting, such that the microchannels and conduits, as described herein are within a microchip. In some embodiments, desalting in the microchip setting minimizes sample loss during chip-to-world interfacing, for example, via subsequent assay or analysis of the solution or species of interest in machinery which can accommodate a microchip. In some embodiments, the salt concentration as a result of the methods/using the devices of this invention is sufficiently low that MALDI sample detection may be accomplished.

In some embodiments, the desalting methods/devices to accomplish the same of this invention may be controlled by external electric field configurations, exclusively. In some embodiments, desalting or isolating the species of interest did not necessitate incorporation of a complex mechanical system.

In some embodiments, the desalting methods/devices of this invention, or devices/methods for the isolation of a species of interest have a high flow rate even in the absence of additional mechanical pumping mechanisms, which in some embodiments, is superior to current electro-osmotic pumping devices. In some embodiments, the high flow rate is useful in high throughput sample preparation for micro-total analysis systems.

In some embodiments, the desalting methods/devices of this invention are useful for the preparation of nanofluidic pumps, for high throughput sample preparation. In some embodiments, the desalting methods/devices of this invention are useful for the preparation of desalted buffer solutions for mass spectroscopy applications, for example, for a species of interest concentrated and suspended in such a solution. In some embodiments, the methods of this invention result in the reversal of the direction of liquid flow in a microchannel. In some embodiments, methods of this invention result in the switching or stopping of liquid flow in a channel.

Figure 3A:
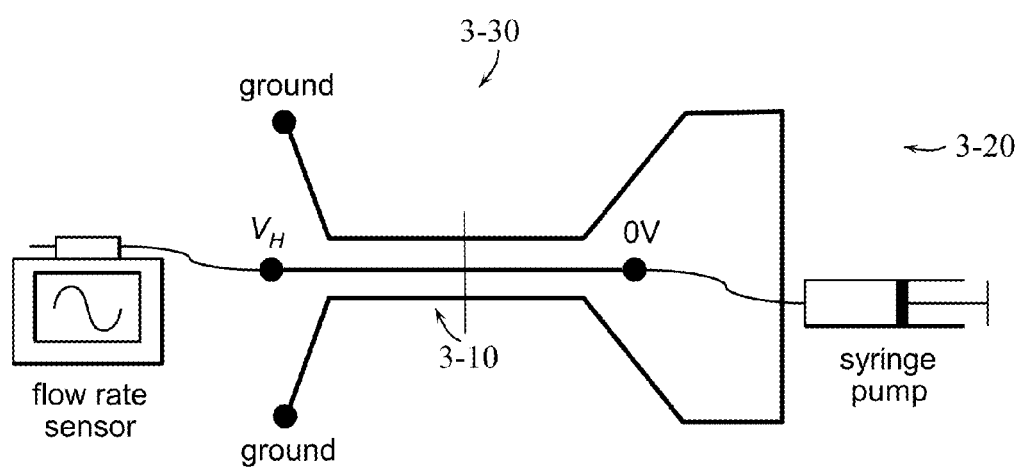
FIG. 3(a) Schematics of flow rate measurement system with an external syringe pump. (b) Fluid pumping hysteresis as a function of ET and buffer ionic concentration under external pressure fields which have the opposite direction against ET ($V_L$ was fixed at 0V, while $V_H$ was varied). Positive values of flow rate were switched to negative values due to amplified electrokinetic flow within 2 seconds. (c) Sequential images of fluid switching using amplified electrokinetic flow under an external pressure field. The direction of net flow was switched by increasing ET against the pressure fields. The number on each image corresponds on that in FIG. 3(b).
Figure 3B:
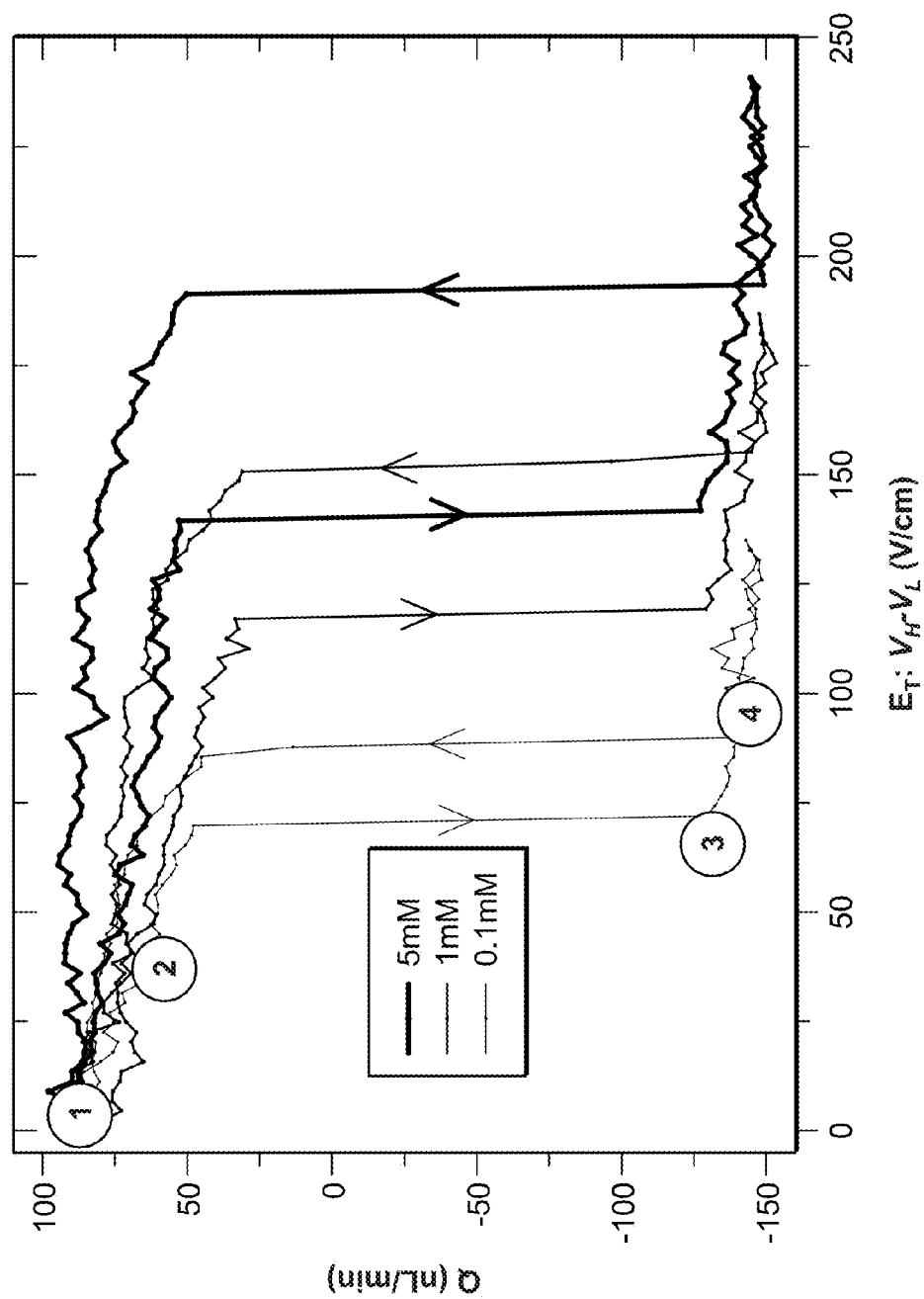
FIG. 3 schematically depicts embodiments of a device for reversing the flow direction of a liquid.
Figure 3C:
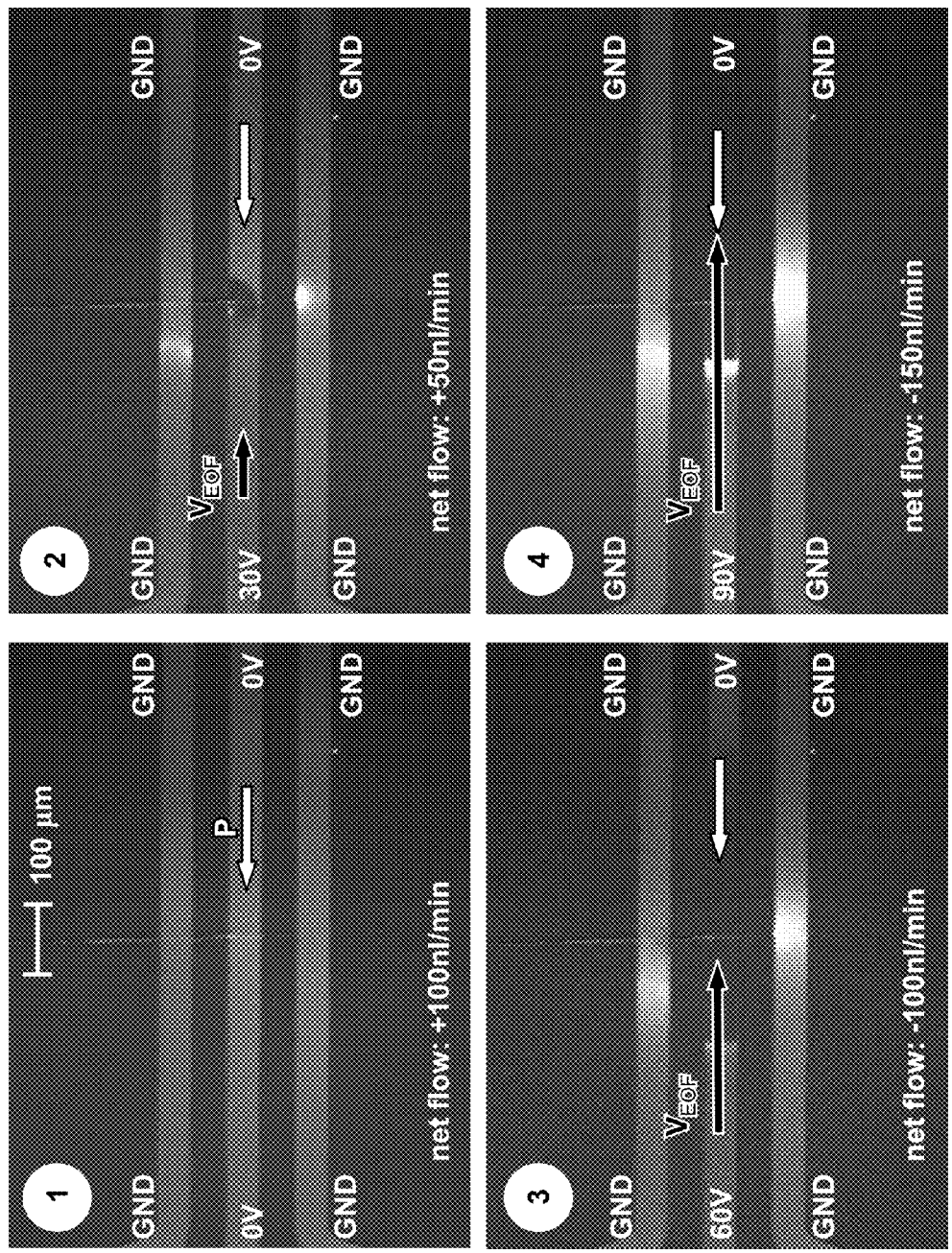

In one embodiment, a reversal of the direction of a pressure driven flow is achieved. FIG. 3 depicts one embodiment, in which a method of this invention is used to switch the direction of a pressure-driven flow. In FIG. 1($a$) a dual side device is shown with a sample microchannel (3-10) coupled to two buffer microchannels (3-20) through conduit or conduits (3-30). A syringe pump is used to controllably push liquid or fluid from the right (second) side of the sample microchannel to the left (first) side of the sample microchannel, wherein a flow rate sensor is connected. FIG. 3($c$) shows four stages in the operation of the device. In stage 1, $V_H=V_L=0$. At this stage only the pressure-driven flow is present, and the flow rate sensor senses a flow from right to left of 100 mL/min. In stage 2, $V_H=30$ V and $V_L=0$. At this stage an electrokinetic flow is formed in a direction opposite to the pressure driven flow direction (i.e. from left to right). The net result of the two factors decrease the original flow rate, and the sensor senses a flow from right to left of only 50 mL/min. In stage 3, $V_H=60$ V and $V_L=0$. At this stage the electrokinetic flow overcomes the pressure driven flow, and the overall flow direction is reversed (i.e. flow direction is now from left to right). At stage 3 the sensor senses a flow from left to right of 100 mL/min. In stage 4, $V_H=90$ V and $V_L=0$. At this stage the electrokinetic flow effect becomes larger and the overall flow rate is 150 mL/min from left to right, which is the direction opposing the pressure. Note that by removing the voltage $V_H$ from the left side of the sample microchannel, flow direction and flow rate can return to the original pressure-driven only flow. The whole process is thus reversible and controlled. Flow direction can be switched cyclically or in a step-wise manner, and a full spectrum of flow rates in each direction can be achieved by simply changing $V_H$.

FIG. 1($b$) is a plot of the flow rate in nL/min vs. The voltage difference applied to the sample microchannel. The voltage difference ($V_H$-$V_L$) is shown in field units as V per cm. Stages 1, 2, 3 and 4 described above, are marked on the graph. In stages 1 and 2, flow direction is dictated by the syringe pump and is directed from right to left. In stages 3 and 4, flow direction is dictated by the electrokinetic induced flow and is directed from left to right (negative flow values represent reversal of flow direction). When $V_H$ is lowered, flow direction is switched back. The reversibility of the process can be observed from the cyclic plot, wherein the downward arrow represent an increase in electrokinetic flow and wherein the upward arrow represents decreasing the value of $V_H$ and switching flow direction back to the direction controlled by the pressure, i.e. from right to left. The two subsequent cyclic plots in FIG. 2($b$) corresponds to processes wherein sample ion concentration was different, thus affecting the flow direction switching voltage. Higher sample ion concentrations required higher voltages $V_H$ to be applied for switching the flow direction.

Methods of this invention may employ various configurations of a device. Devices used in methods of this invention may have different features, different dimensions, different number of microchannels and conduits, different inlets and outlets and various sample, buffer, collection and waste reservoirs or containers.

Figure 4A:
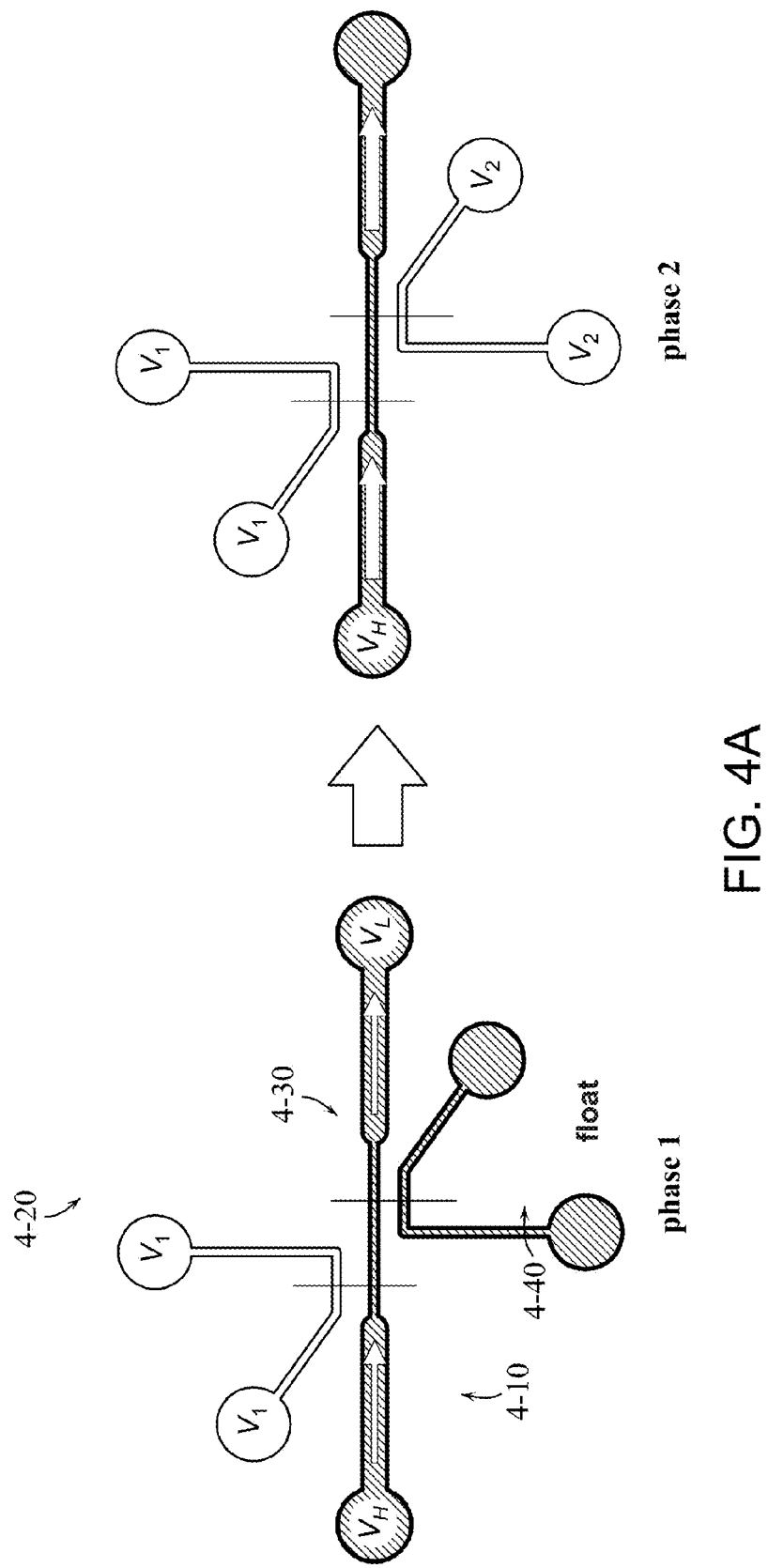
FIG. 4(a) Schematics of multi-nanojunctions devices for higher flow rate. Initially, the fluid was pumped via $V_1$ (phase 1), then the ion depletion zone was created and started to pumping. After a while, $V_2$ was set below $V_1$ (phase 2), while $V_1$ was maintained ($V_H$>$V_L$>$V_1$>$V_2$). Combined function of $V_1$ and $V_2$ can give higher flow rate than phase 1. (b) Massively parallel channel devices for high throughput applications. The fluids coming from each microchannel which connected by nano junction were merged into one microchannel.
Figure 4B:
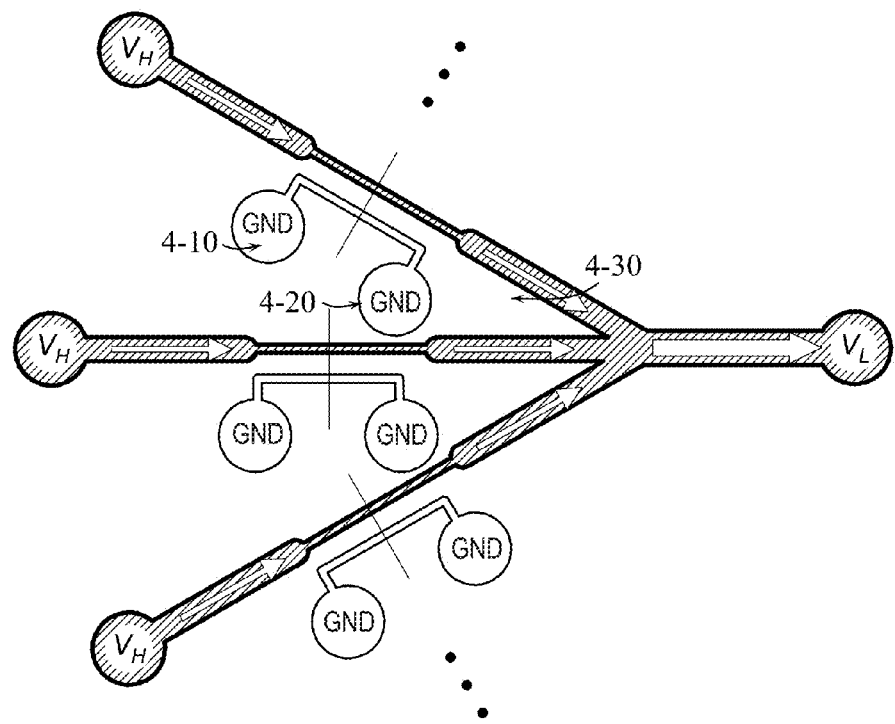
FIG. 4 schematically depicts embodiments of a device for high throughput operation.
Figure 5:
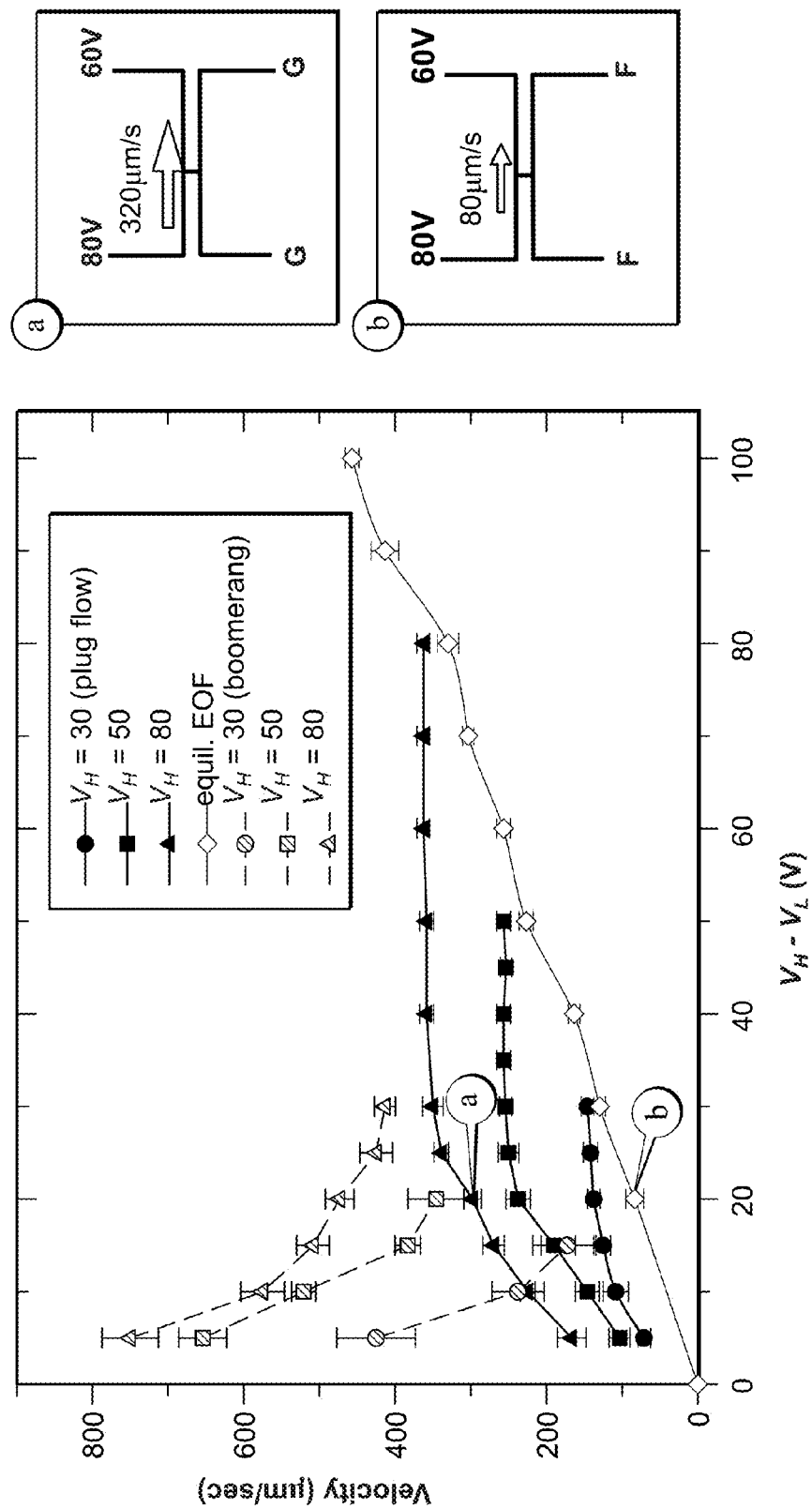
FIG. 5 schematically depicts the velocities of equilibrium and non-equilibrium EOF (inside/outside depletion region) as a function of $E_T$.

In one embodiment, a method of this invention uses a device having two separate conduit areas and two separate buffer microchannels. FIG. 4($a$) is a schematic of multi-nanojunctions devices designed for achieving higher flow rates. Nanojunctions in this context are the linkage or coupling areas of the sample microchannel with the conduits. In phase 1, the fluid was pumped by applying $V_1$ to the first buffer microchannel (4-20). An ion depletion zone was created and pumping was started. In phase 2, $V_2$ applied to the second buffer microchannel (4-40) was set below $V_1$, while $V_1$ was maintained. The values for the voltages were kept as follows: ($V_H$>$V_L$>$V_1$>$V_2$). Combined function of $V_1$ and $V_2$ can give higher flow rate than phase 1 the rate obtained in phase 1. In one embodiment, more than two buffer channels and or more than two nanojunctions are used. In one embodiment, 10 nanojunctions are used. In one embodiment the number of nanojunctions used on the same sample microchannel ranges between 1-10. In one embodiment the number of nanojunctions used on the same sample microchannel ranges between 10-100. In one embodiment the number of nanojunctions used on the same sample microchannel ranges between 5-15. In one embodiment the number of nanojunctions used on the same sample microchannel ranges between 1-5.

FIG. 4($b$) represent an embodiment of a method comprising the use of massively parallel channel devices for high throughput applications. The fluids coming from each of the sample microchannels (4-10) which are all connected by separate conduits (4-30) were merged into one sample microchannel.

In one embodiment, the surface of the microchannel has been functionalized to reduce or enhance adsorption of said species of interest to said surface. In another embodiment, the surface of the conduit and/or microchannel has been functionalized to enhance or reduce the operation efficiency of the device. In another embodiment, external gate potential is applied to the substrate of the device, to enhance or reduce the operation efficiency of the device. In another embodiment, the device is comprised of a transparent material. In one embodiment, the transparent material is borosilicate glass (Pyrex™), silicone dioxide, silicon nitride, quartz or SU-8.

In other embodiments, downstream separation devices, which may interface with the sample microchannels of this invention include, but are not limited to, micro high performance liquid chromatographic columns, for example, reverse-phase, ion-exchange, and affinity columns.

It is to be understood that the exact configuration of any systems, devices, etc. which are coupled downstream of the sample microchannels are to be considered as part of this invention, and that the configuration may be varied, to suit a desired application. In one embodiment, a module for separation of the concentrated peptides which is positioned downstream of the concentrating device comprises a separation medium and a capillary between the ends of which an electric field is applied. The transport of a separation medium in the capillary system and the injection of the sample to be tested (e.g., a sample band comprising peptides and/or partially digested polypeptides) into the separation medium can be carried out with the aid of pumps and valves, or in another embodiment, via electric fields applied to various points of the capillary.

In another embodiment, the method is utilized to detect said species of interest when said species is present in said liquid at a concentration, which is below a limit of detection.

In one embodiment, this invention provides a method of diminishing the salt concentration of or desalting a solution, the method comprising the steps of:
introducing a liquid comprising salt ions from a source into a microfluidic device comprising:
  a substrate
  at least one sample microchannel through which said liquid comprising salt ions can be made to pass from a first side to a second side;
  at least one buffer microchannel or buffer reservoir comprising a buffer;
  at least one conduit linked to said sample microchannel and to said buffer microchannel or reservoir; and
  at least one unit to induce an electric field in said conduit, said sample microchannel, said buffer microchannel or buffer reservoir or a combination thereof; and
inducing gravity-driven liquid flow in said sample microchannel whereby said flow is introducing said liquid into said device through said sample microchannel; and
inducing an electric field in said conduit, whereby salt ion depletion occurs in said sample microchannel in a region proximal to said conduit and whereby said salt ions are confined to a region within said sample microchannel that is distant from said conduit.

In one embodiment, in such gravity-operated devices there is no additional power needed for the sample delivery unlike RO or ED conventional systems.

In one embodiment, this invention provides a method of diminishing the salt concentration of or desalting a solution, the method comprising the steps of:
introducing a liquid comprising salt ions from a source into a microfluidic device comprising:
  a substrate
  at least one sample microchannel through which said liquid comprising salt ions can be made to pass from a first side to a second side;
  at least one buffer microchannel or buffer reservoir comprising a buffer;
  at least one conduit linked to said sample microchannel and to said buffer microchannel or reservoir; and
  at least one unit to induce an electric field in said conduit, said sample microchannel, said buffer microchannel or buffer reservoir or a combination thereof, wherein said unit is operated by a photovoltaic/solar cell; and
inducing liquid flow in said sample microchannel whereby said flow is introducing said liquid into said device through said sample microchannel; and
inducing an electric field in said conduit, whereby salt ion depletion occurs in said sample microchannel in a region proximal to said conduit and whereby said salt ions are confined to a region within said sample microchannel that is distant from said conduit.

According to this aspect and in one embodiment, in such solar-cell-operated devices the ICP desalination process is powered by photovoltaic cell (e.g. a solar cell). One of most significant features of the ICP desalination is low power consumption that means the operation power can be supplied by either rechargeable battery or by photovoltaic cells. Current photovoltaic cell can produce averagely ~25 mW/cm. With this efficiency, the total area of photovoltaic cell should be ~2700 cm$^2$ (2250 µW×3×10$^4$/25 mW/cm$^2$) in order to power 300 mL/min operation. This size (~50 cm×50 cm) of flexible photovoltaic cell needed is adequate for a portable system, which would render this portable desalination system solar-powered.

In one embodiment, this invention provides a method of diminishing the salt concentration of or desalting a solution, the method comprising the steps of:
introducing a liquid comprising salt ions from a source into a fluidic channel comprising:
  a substrate
  at least one sample fluidic channel through which said liquid comprising salt ions can be made to pass from a first side to a second side;
  at least one buffer fluidic channel or buffer reservoir comprising a buffer;
  at least one perm-selective conduit linked to said sample fluidic channel and to said buffer fluidic channel or reservoir; and
  at least one unit to induce an electric field in said conduit, said sample microchannel, said buffer microchannel or buffer reservoir or a combination thereof; and
inducing a electric field through said conduit, whereby salt ion depletion occurs in said sample microchannel in a region proximal to said conduit and whereby said salt ions are confined to a region within said sample microchannel that is distant from said conduit.

In one embodiment, liquid introduction from a source into said fluidic device comprising a pressure inducing unit, an electroosmotic flow inducing unit, a gravity feeding unit or a combination thereof.

In one embodiment, the fluidic device further comprising a second substrate positioned proximally to or adhered to the first substrate or a portion thereof. In one embodiment, the liquid comprising salt is sea water.

In one embodiment, the method is used for desalting sea water for drinking. In one embodiment the sample fluidic channel is a microchannel. In one embodiment, the sample fluidic channel further comprising a first outlet for low salt concentration solution and a second outlet for high salt concentration solution. In one embodiment, the first outlet for low salt concentration solution is linked to the ion depletion zone in the sample channel and the second outlet for high salt concentration solution is linked to the region that is distant from the perm-selective conduit wherein salt ions are confined.

In one embodiment, the electric field in the sample channel and across the perm-selective conduit is generated by applying a higher voltage to the sample channel and a lower voltage to the buffer channel or buffer reservoir. In one embodiment, the higher voltage, the lower voltage or a combination thereof are positive voltages. In one embodiment, the positive voltage is between 50 mV and 500 V. In one embodiment, the higher voltage is positive and the lower voltage is achieved by electrically grounding the buffer channel. In one embodiment, the electric field in the perm-selective conduit is generated by applying a higher voltage to the side of the conduit that is linked to the sample channel and a lower voltage to the side of the conduit that is linked to the buffer channel. In one embodiment, the higher voltage is positive and the lower voltage is applied by electrically grounding the buffer microchannel or reservoir linked to the perm-selective conduit.

In one embodiment, the higher voltage is the result of the three voltages applied to said first side, to said second side and to said inlet of said sample channel. In one embodiment, the higher voltage is a result of the voltages applied to the first side and to the second side of the sample channels. In an embodiment wherein the sample channel is divided to two channels (for desalted and salted streams), the higher voltage at the intersection of the microchannel and the perm-selective conduit is a result of the voltage at the inlet (first side) of the sample channel, and the voltages at the two outlets (two "second sides") of the sample microchannel. In one embodiment all three voltages are equal and the (fourth) voltage at the buffer channel/buffer reservoir is zero (the channel is grounded). In one embodiment, the higher voltage has an intermediate value lying between the values of the two voltages applied to the first side and to the second side of the sample channel.

In one embodiment, the electric field is induced by applying a voltage ranging between 50 mV and 500 V to the first side of the sample microchannel and to the second side of the sample microchannel (or to the first side and to the two "second sides" if the channel is split to a salted and desalted streams) and by electrically grounding the buffer microchannel or reservoir.

Figure 10B:
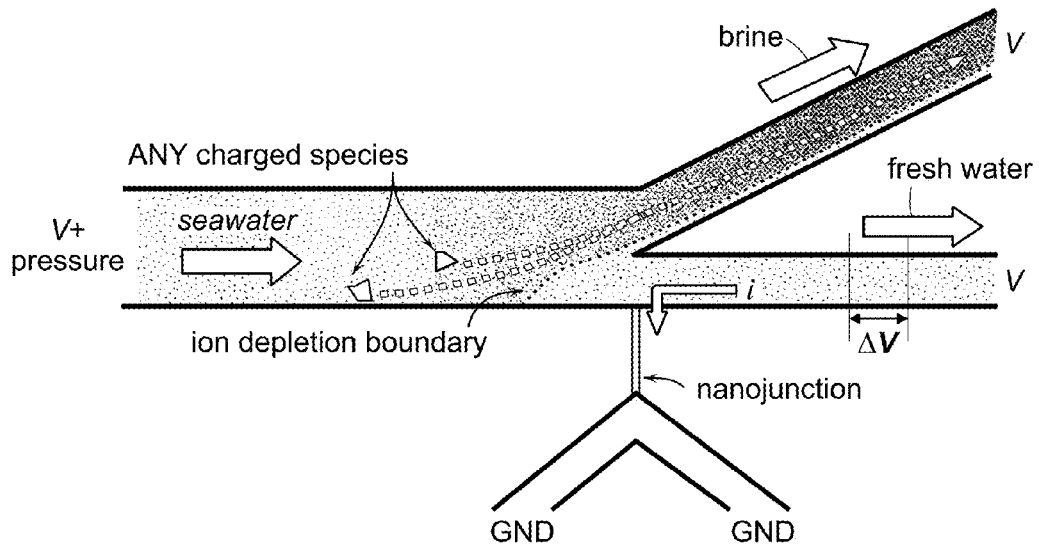
Figure 12A:
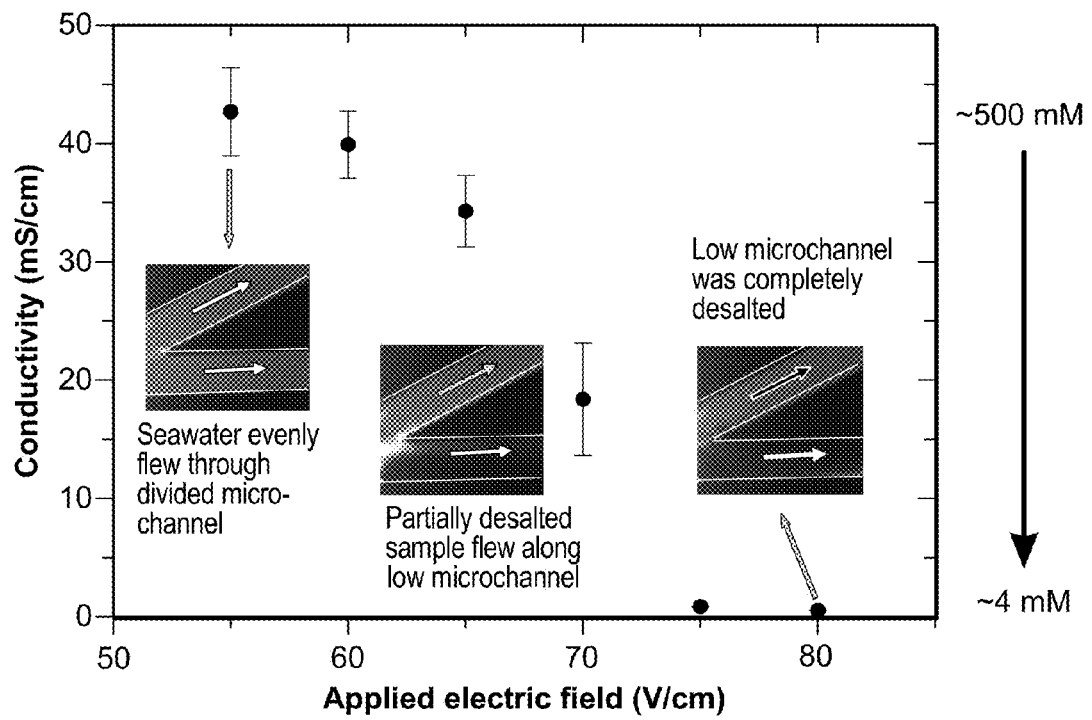
FIG. 12 illustrates an embodiment of the conductivity of a desalted stream in experiments with (a) seawater sample and (b) 100 mM phosphate buffer solution, as a function of applied electric field. In both cases, the conductivity of the desalted stream dropped to a few mM level, once the electric field value reached the threshold. This result coincides with the establishment of ICP zones, observed by the fluorescent trackers.
Figure 12B:
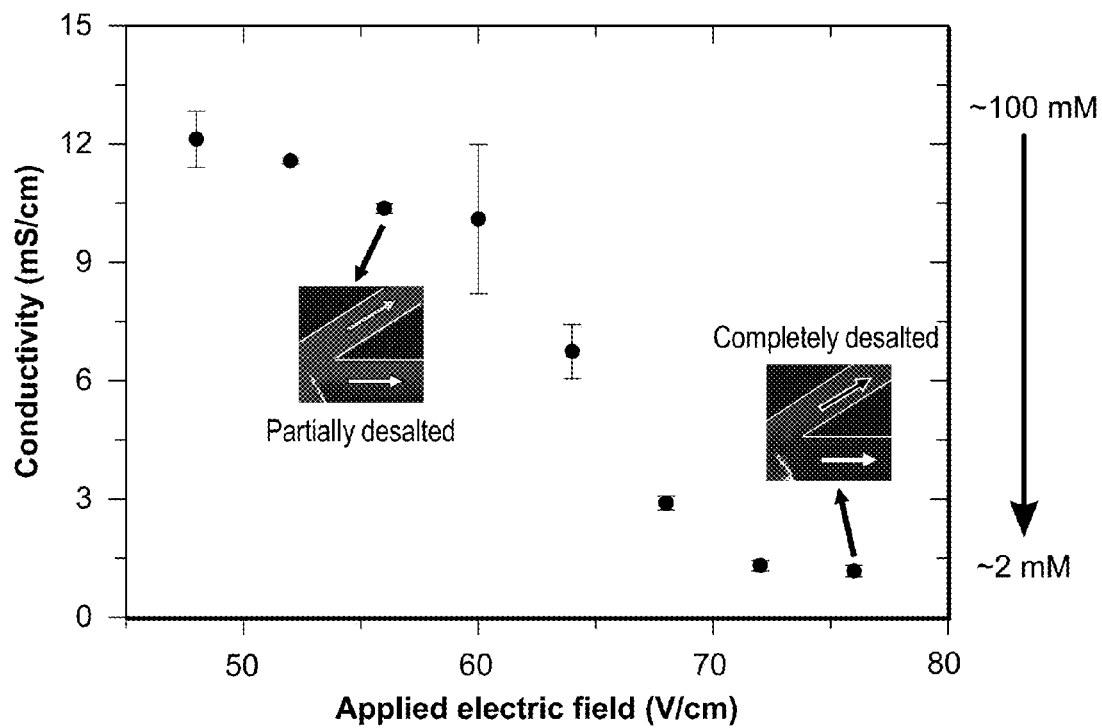

In one embodiment, the device as illustrated in FIG. 10 has sample channels with one inlet and two outlets and a buffer channel. In one embodiment, the inlet corresponds to the "first side" and the two outlets correspond to the "second side" for embodiments where first and second sides are discussed and wherein the second side is divided to the two channels.

In one embodiment, the inlet is the first side. In one embodiment, the "second side" or the outlet or outlets form the salted channel and the desalted channel. According to this aspect, both the salted and desalted channels are referred to as outlets and as "second sides" of the channel.

In one embodiment, the width of the sample channel, the buffer channel or a combination thereof is between 1-1000 μm. In one embodiment, the depth of the sample channel, the buffer channel or a combination thereof is between 0.5-500 μm. In one embodiment, the width of the conduit is between 100-4000 nanometers. In one embodiment, the width of the conduit is between 1-100 micrometers. In one embodiment, depth of the conduit is between 20-100 nanometers. In one embodiment, the depth of the conduit is between 1-100 micrometers.

In one embodiment, the conduit comprises a nanochannel or a nanoporous material in order to possess perm-selectivity. According to this aspect and in one embodiment, the conduit, itself, has the dimensions of 1~1000 μm width and 1~1000 μm depth, and comprises nanometer size pores (or comprises nanochannel(s)) having the dimensions of 1~100 nm (either diameter (cylindrical shape) or length/width of one side (rectangular shape)).

In one embodiment, the conduit comprises one nanochannel. In one embodiment, the conduit comprises numerous nanochannels. In one embodiment, the conduit comprises a large number of nanochannels. In one embodiment, the conduit comprises a bundle of nanochannels.

In one embodiment, the conduit comprising a polymer-based permselective material.

In one embodiment, the polymer-based permselective material comprising a co-polymer of tetrafluorethylene and sulfonic acid, Teflon, hydrogel. In one embodiment, the polymer-based permselective material comprising a cation selective or an anion selective material. In one embodiment, the conduit comprises an electrical junction that is preferentially conductive to positive ions or to negative ions.

In one embodiment, the surface of the sample channel has been functionalized to reduce adsorption of species of interest to said surface. In one embodiment, the surface of said conduit and/or the first, second or buffer channel has been functionalized to enhance the operation efficiency of the device.

In one embodiment, an external gate voltage is applied to the substrate of the device, to enhance the operation efficiency of the device. In one embodiment, the sample channel, said buffer channel, said conduit or combination thereof, are formed by lithography, etching and plastic molding processes.

In one embodiment, the device is comprised of a transparent material. In another embodiment, the device is comprised of a non-transparent material. In one embodiment the use of a transparent material is for imaging of device operation. In one embodiment, the use of transparent material is for analysis. In one embodiment, the transparent material is borosilicate glass (Pyrex™), silicone dioxide, silicon nitride, quartz or SU-8.

In one embodiment, the device is coated with a low-autofluorescent material. In one embodiment, the device is coupled to a syringe pump or gravitationally operated pump. In one embodiment, the device is coupled to a sensor, separation system, detection system, analysis system or combination thereof. In one embodiment, the detection system comprises an illumination source, a camera, a computer, a luminometer, a spectrophotometer, or a combination thereof.

In one embodiment, the liquid flow speed in said sample microchannel is between 10 μm/sec and 10 mm/sec. In one embodiment, the device comprises multiple sample channels, multiple buffer channels, multiple conduits or combinations thereof. In one embodiment, the multiple channels, conduits or combinations thereof are arranged with a particular geometry or in an array. In one embodiment, the array comprises at least 100 sample channels, at least 100 buffer channels and at least 100 conduits. In one embodiment, the geometry or the array comprises perpendicular orientation of the channels with respect to the conduits.

In one embodiment, the device length, width, height or a combination thereof ranges between 10 cm to 30 cm.

In one embodiment, the liquid volume flow rate is at least 100 mL/min. In one embodiment, the liquid volume flow rate ranges between 60-100 L/min. In one embodiment, the electrical power needed for device operation ranges between 10 w to 100 w. In one embodiment, the flow through said sample channel is continuous.

In one embodiment, desalting devices of this invention do not utilize an electroosmotic induced field but rather, the fluid is introduced to the device by pressure, using gravity, by a pressure pump, a syringe or any other pressure-inducing or flow inducing mechanism. In one embodiment, a major element of the device is the presence of a perm-selective nanojunction or "conduit" between two fluidic channels, such that with the application of an electric field across the conduit induce ion depletion in one (or both) channels, which is then used to desalt at least one of the fluid streams.

In another embodiment, a second electric field is applied to the sample fluidic channel in order to induce fluid flow in the channel. In one embodiment, the sample fluidic channel has a width or depth or both in the micrometer range. In one embodiment, the width/depth of the channel is ranging between 1 micron and 1000 microns. In one embodiment, the length of the sample fluidic channel ranging between 1 micron and 1000 microns, or between 1 micron and 10,000 microns.

IV. Embodiments of Methods of the Invention

In one embodiment, the method is adapted for assay of biomolecules. In one embodiment, while in a microfluidic device, the salt concentration of a solution in which biomolecules are present is reduced by methods of this invention. In one embodiment, salt or charged species concentration is reduced in one portion of the microfluidic device prior to mixing with a solution containing the biomolecule or substance of interest which is located in another portion of the device. In one embodiment, when the biomolecule solution is mixed with the desalted solution, a chemical reaction can be initiated. In one embodiment, the mixing assists in preserving the biomolecule. In one embodiment, mixing the molecule solution with the desalted solution increases the stability of the biomolecule. In one embodiment, mixing the biomolecule solution with the desalted solution, the shelf life of the biomolecule solution is increased. In one embodiment, mixing of the biomolecule solution with the desalted solution activates a fluorescent marker bound to the macromolecule. In one embodiment, such mixing changes the pH of the biomolecule solution. In one embodiment the mixing changes the color of the solution. According to this aspect and in one embodiment, the mixing changes the spectroscopic response of the solution. In one embodiment the spectroscopic response changed is in the IR region. In one embodiment the spectroscopic response is in the UVNIS region. In one embodiment, mixing causes a precipitation of one or more substances present in the biomolecule solution. In one embodiment, mixing of the desalted solution with the biomolecule containing solution causes dissolution of a solid substance that is present in contact with the biomolecule solution. In one embodiment mixing with the desalted solution, dilutes the solution. In one embodiment, diluted solution is needed for assay, diagnostics, synthesis, or for injection to a subject or for other medical use. In one embodiment, the mixing prepares the biomolecule for an assay. In one embodiment, mixing prepares the biomolecule for analysis. In one embodiment, the desalted solution is so diluted to the level of pure water. In one embodiment, the dilution of the solution yields de-ionized water, water with very low electrical conductance, water with electrical resistance equal or higher than 18 Mohm. Water with salt concentration lower than 1000 µM. In one embodiment, the purified water with properties mentioned above are used to dilute a solution or a molecule of interest. In one embodiment, the purified water are used for dissolving a solid substance. In one embodiment, the purified water are used for rinsing or cleaning parts of the microfluidic device, and for rinsing and cleaning materials or solutions in the device. In one embodiment, such purified water are used for extraction procedures taking place within the microfluidic device. In one embodiment extraction is a method to separate compounds based on their relative solubilities in two different immiscible liquids, usually water and an organic solvent. In one embodiment, a substance is extracted from one liquid phase into another liquid phase.

In one embodiment, the method is adapted for synthesis in the micron scale. In one embodiment, synthesis in the micron scale comprises synthesis using volumes in the micro-liter range. In one embodiment synthesis in the micron scale comprises reactors, bio-reactors, synthesis containers, and/or sample tubes, channels or conduits having at least one dimension ranging between 1 micrometer and 1000 micrometer. In one embodiment synthesis in the micron scale or microsynthesis is referred to small scale synthesis, synthesis wherein small amounts of reactants are used, and small amounts of products are being produced. In one embodiment, such synthesis is directed toward expensive materials, sensitive materials, rare materials, hazardous materials, high purity products, medicinal products, drugs, unstable materials or derivatives thereof.

In one embodiment, the method is adapted for chemical or biological analysis. In one embodiment, methods of this invention provide accelerated flow, flow pumping, flow switching, fluid desalting and fluid dilution that may aid in chemical and biological analysis.

In one embodiment, pumping and accelerating fluid flow reduces the time needed for analysis. In one embodiment reducing the time also reduces the cost of the analysis. In one embodiment, accelerating sample flow enables to carry out analysis of unstable or sensitive materials, materials that deteriorate or decompose after a certain period of time. In one embodiment, pumping and accelerating fluid flow results in a more efficient analysis. In one embodiment, pumping mechanisms of this invention may be used to withdraw sample fluid from an otherwise inaccessible sites. In one embodiment such pumping can be utilized to withdraw fluids from a subject for medicinal analysis. In one embodiment such pumping can be utilized to withdraw fluids from environmental sites for environmental analysis. In one embodiment such pumping can be utilized to withdraw fluids from a hazardous sample for analysis. In one embodiment, withdrawing of fluid by pumping mechanisms of this invention can be performed remotely by remotely applying voltages to a device of this invention. In one embodiment, remote analysis is beneficial for explosives, chemical hazards, biological agents, toxic materials or for pumping of fluid into a transplanted device. In one embodiment, methods of this invention provide flow acceleration and flow pumping to proceed in devices with low power consumption.

In one embodiment, the ability to switch the direction of the flow and to stop flow by methods of this invention may find uses in analysis. In one embodiment, stopping a flow or switching flow direction can control an analysis procedure. In one embodiment, procedures can be controlled by initiating or terminating an analysis step which involves the transfer of the fluid sample from one area to another or from one analysis module to another. In one embodiment, electrically switching or stopping of fluid flow eliminates the need for mechanical fluid pumps which simplify the analysis technique.

In one embodiment, fluid desalting or dilution of a liquid sample can be achieved using methods of this invention. In one embodiment, desalting or dilution is important for analysis in which low concentration of a species is required. In one embodiment, desalting or dilution is important for analysis of an electrically neutral species that needs to be present in a diluted or desalted solution for accurate analysis. Examples are for analysis techniques in which the concentration of species, or the concentration of accompanying charged species affect the analysis outcome are, among others, spectroscopies, chromatography, electrochemistry and surface analysis techniques for dried materials. In one embodiment, desalting and/or dilution of liquid samples by methods of this invention yield the desired sample purity needed for detection or analysis.

In one embodiment, the method is adapted for sampling or diagnosis. In one embodiment, as described above, pumping and flow acceleration can be used for efficient sampling of fluids. In one embodiment, the first side of the sample microchannel is connected to a sample reservoir or any other fluid sample source, and by applying a voltage to both sides of the sample microchannel and to the buffer microchannel, fluid is withdrawn into the sample microchannel from the sample source, allowing sampling to be carried out. In one embodiment, such sample can be transferred by methods of this invention through the second side of the sample microchannel to an analysis site for diagnosis.

In one embodiment, the method is adapted to implanted devices where injection or fast pumping of a solution into or out of the device is required. In one embodiment, such implanted device can be operated remotely. In one embodiment, such implanted device can be used for sampling of body fluids on a regular basis. In one embodiment, an implanted device working according to methods of this invention may be used to release drugs in accurate doses and at precise times into a patient's blood stream or into a tissue.

In one embodiment, the method is adapted for pumping of miniscule amounts of fluid in environmentally dry areas, under dry experimental conditions, under extreme temperature, pressure and humidity conditions and from very small sample sources. In one embodiment, the method is adapted for preparation of pure water. In one embodiment, pure water is water in which electrolyte concentration is zero. In one embodiment, pure water is water wherein electrolyte concentration is very low. In one embodiment, pure water is water with very high electrical resistivity. In one embodiment, purified water is water that is physically processed to remove impurities. In one embodiment, high purity the concentration of trace contaminants in purified water is measured in parts per billion (ppb) or parts per trillion (ppt). Removal of ions causes water's resistivity to increase, providing a convenient measurement for the exact extent of deionization. Ultrapure deionized water has a theoretical maximum resistivity of 18.31 MΩ·cm and a theoretical minimum conductivity of 0.0545 microsiemens/cm, compared to around 15 kΩ·cm and 70 microsiemens/cm for tap water. In one embodiment, pure water used by methods of this invention has a resistivity value ranging between 15 kΩ·cm and 18.31 MΩ·cm. The American Society for Testing and Materials (ASTM), and The National Committee for Clinical Laboratory Standards (NCCLS), classify purified water into Types I-III depending upon the level of purity. Types I-III purified characteristics are summarized below.

| Maximum Contaminant Levels in Type I-III Purified Water | | | | |
|---|---|---|---|---|
| Contaminant | Parameter | Type I | Type II | Type III |
| Ions | Resistivity at 25° C. (megaohms-cm) | >18.0 | >1.0 | >0.05 |
| | Conductivity at 25° C. (microsiemens/cm) | <0.056 | <1.0 | <20 |
| Organics | TOC (ppb) | <10 | <50 | <200 |
| Pyrogens | Eu/mL | <0.03 | NA | NA |
| Particulates | Size | <0.2 μm | NA | NA |
| Colloids | Silicia (ppb) | <10 | <100 | <1000 |
| Bacteria | CFU/mL | <1.0 | <100 | <1000 |

In one embodiment, purified water produced by methods of this invention is used for drinking. In one embodiment, methods of this invention use devices with arrays of sample microchannels, operating in parallel, into which sea water is introduced. In one embodiment, the outlet or the second side of the sample microchannels are linked to a desalted stream channel or tube and to a salted stream channel or tube. In one embodiment, the desalted stream is directed to the desalted channel. In one embodiment, the desalted streams from all sample microchannels are connected to a collection container. In one embodiment, the collection container is filled with drinking water that exit from the second side of the sample microchannel. In one embodiment, methods of this invention for preparing drinking water can be used in areas where drinking water is scarce. In one embodiment, such methods can be utilized for removing contaminant or hazardous ions or charged species from water to upgrade it for safe drinking. In one embodiment, the preparation of drinking water comprises removal of ions or charged species that deteriorate the water taste or smell. In one embodiment, methods of this invention are directed to low power operation. In one embodiment, devices used in methods of this invention consume power ranges between 10 w to 100 w. In one embodiment, devices used in methods of this invention consume power ranges between 100 w to 1000 w. In one embodiment, devices used in methods of this invention consume power ranges between 1000 w to 10000 w. In one embodiment, devices used in methods of this invention consume power ranges between 10 w to 50 w. In one embodiment, devices used in methods of this invention consume power ranges between 50 w to 100 w. In one embodiment, desalination of water for drinking consumes much less power than other desalination techniques such as distillation and reverse osmosis. In one embodiment, desalination methods of this invention utilize compact systems and does not require heavy filters or heavy ion-exchange cylinders or materials. In one embodiment desalination devices utilized by methods of this invention can be used repeatedly. In one embodiment such devices does not need replacement parts and do not require high maintenance.

In one embodiment, this invention provides small scale micro/nano fluidic unit devices utilizing ICP phenomenon which was demonstrated for membraneless direct desalination of seawater. This proposed system has several unique and attractive features for direct seawater desalination applications. Most importantly, it can eliminate any charged species, size-ranging from small salt ions to large particles/cells, without suffering from membrane fouling and clogging in conventional methods that involve passage of the solution to be desalinated through a membrane. This can significantly reduce the complexity and cost of direct seawater desalination. Unlike ED or RO technologies, the particles and salts are driven away from the critical nanojunction and re-routed into a different stream continuously, inherently preventing clogging and fouling of the nanojunction. This enables robust long-term operation without the need for cleaning/exchanging the membranes. The technology presented enables straightforward seawater desalination in a system that does not require high pressure pumping or recirculation elements. The techniques of the present invention can be realized in a small portable unit with low power consumption with the possibility of battery-powered operation. Therefore, it is adequate for seawater desalination in disaster/poverty-stricken areas, where the necessary infrastructures are lacking for operation of large scale desalination systems. This technology may become a high-efficiency alternative for ED or RO.

In one embodiment, this invention provides, systems and methods for purifying water or other solvents which can find applications in analytical techniques such as chromatography (e.g. HPLC and GC), in mass spectrometry sample preparations, in electrochemical techniques, in electrochemical separations, in microfluidics, as a substitute for filters or membranes in any industry requiring pure water or pure solvents. In one embodiment, this invention provides systems and methods for desalination and for water purification. In one embodiment, water purification by systems or methods of the present invention are used for drinking and/or for other household purposes.

In one embodiment, the term "a" or "one" or "an" refers to at least one. In one embodiment the phrase "two or more" may be of any denomination, which will suit a particular purpose.

In one embodiment, "about" or "approximately" may comprise a deviance from the indicated term of +1%, or in some embodiments, −1%, or in some embodiments, ±2.5%, or in some embodiments, ±5%, or in some embodiments, ±7.5%, or in some embodiments, 10%, or in some embodiments, ±15%, or in some embodiments, +20%, or in some embodiments, ±25%.

Various modes of carrying out the invention are contemplated as being within the scope of the following claims particularly pointing out and distinctly claiming the subject matter, which is regarded as the invention.

EXAMPLES

Materials and Methods

Device Fabrication:

Fabrication techniques were as described (J. Han, H G. Craighead, *J. Vac. Sci. Technol.*, A 17, 2142-2147 (1999); J. Han, H G. Craighead, *Science* 288, 1026-1029 (2000)). Two reactive ion etchings were used. After patterning the 5-20 □m wide conduits with standard lithography tools, the first reactive ion etching (RIE) etching was conducted for about 10 sec to etch 40 nm conduit, while the second etching created two parallel 1.5 □m microfluidic channels across the nanofilter. Nanofilters with a depth between 30 and 70 nm were fabricated to demonstrate the effects of buffer concentration and channel depth. After completing RIE etching, KOH etching was used to etch through the loading holes. Thermal oxidation was conducted following nitride stripping, which provided proper electrical insulation. The bottom of the device was then bonded with a borosilicate glass (Pyrex™) wafer using standard anodic bonding techniques.

In one embodiment, polydimethylsiloxane (PDMS) microfluidic chips with perm-selective nanojunctions were fabricated using the previously published methods. A polymeric nanojunction was created by infiltrating a co-polymer of tetrafluorethylene and sulfonic acid polymer solution (Sigma Aldrich, 5% w.t.) between the gaps created by mechanical cutting on PDMS substrate which had a mold of microchannels. The PDMS can seal itself with the heterogeneous polymeric nanoporous material between PDMS/PDMS gap. Then the PDMS substrate was bonded with glass plate by plasma treatment. The inlet microchannel and buffer microchannel had the dimension of 500 μm width×100 μm depth and bifurcated microchannels has the same depth, but 250 μm width. For the visualization of micron size particles and WBC, the devices with 100 μm width×15 μm depth were also fabricated. Gold microelectrodes on titanium as an adhesion layer (100 μm wide, 110 nm height and 100 μm spacing between electrodes) for electric potential measurements were deposited at the inlet, desalted and salted microchannel using standard evaporation/lift-off process (Ti: 10 nm and Au: 100 nm).

Using a microfluidic bifurcated channels (the size of each channel was 250 μm width×100 μm depth) shown in FIG. 1, one can separate the 'desalted' stream from 'salted' one, achieving continuous and steady-state desalination. One important characteristic here is that salt ions (and other charged debris) are driven away from (not toward) the membrane, fundamentally eliminating the potential for membrane (nanojunction) fouling.

Biomolecule and Reagent Preparation

A 10 mM phosphate buffer (dibasic sodium phosphate) at pH 9.1 was mainly used, supplemented with 10 □M EDTA to prevent bacterial growth. Successful pre-concentration was demonstrated under conditions of pH 4.6, 10 mM phosphate buffer, as well. Conditions of 10 mM pH 3.5 acetate buffer, and 1× TBE buffer (~80 mM) were without significant pre-concentration effect.

Under conditions of 10 mM phosphate buffer, no polarization effect was observed in channels with a depth greater than 50 nm, probably due to the low pH (which suppressed surface ionization) or too high buffer ionic strength (where the nanofilter becomes less permselective due to smaller Debye length).

Molecules and dyes used included rGFP (BD bioscience, Palo Alto, Calif.), FITC-BSA (Sigma-Aldrich, St. Louis, Mo.), FITC-Ovalbumin (Molecular Probes, Eugene, Oreg.), FITC-BSA (Sigma-Aldrich, St. Louis, Mo.), FITC dye (Sigma-Aldrich, St. Louis, Mo.), Mito Orange (Molecular Probes, Eugene, Oreg.), and lambda-DNA (500 μg/ml). DNA molecules were labeled with YOYO-1 intercalating dyes (Molecular Probles, Eugene, Oreg.) by following manufacturer's instruction.

Also, $NH_2$-GCEHH-COOH (SEQ ID NO: 1) (pI 4.08) peptides were synthesized at the Biopolymers Laboratory at the Massachusetts Institute of Technology and labeled with a thiol-conjugating dye by the following procedure: HPLC purified peptide sample was first reconstituted to a 10 mM peptide concentrated solution (0.1 M pH 7.4 phosphate buffer) as a stock solution, then diluted to 1 mM. The diluted stock solution was mixed at a 1 to 1 ratio with 10 mM TCEP (Molecular Probes, Eugene, Oreg.) and 5-TMRIA dye (Molecular Probes, Eugene, Oreg.). The reaction was allowed to proceed at 4° C. for 24 hours, shielded from exposure to light, following which, non-reacted dyes were terminated by adding 100 mM 2-Mercaptoethanol (Sigma-Aldrich, St. Louis, Mo.), and dialyzed out, using a mini-dialysis kit with 1 kDa cut-off (Amersham Bioscience, Piscataway, N.J.).

Optical Detection Setup

All the experiments were conducted on an inverted microscope (IX-71) with fluorescence excitation light source attached. A thermoelectrically cooled CCD camera (Cooke Co., Auburn Hill, Mich.) was used for fluorescence imaging. Sequences of images were analyzed by IPLab 3.6 (Scanalytics, Fairfax, Va.). A home-made voltage divider was used to distribute different potentials to reservoirs. The built in 100 W mercury lamp was used as a light source, and a neutral density filter is used to reduce the light intensity and to increase the dynamic range of detection.

Quantification of Molecular Concentration

Quantification of the molecular concentration in the channel is depicted in Figure X. Since the device can generate sample plugs that saturate the CCD array used for detection, a neutral density filter, which allowed for at least 12% transmission (Olympus (32ND12)) was used with 70% NA aperture (50% transmission) to decrease excitation light intensity. By decreasing light intensity to 0.6%, the dynamic range of the detector was increased, while the rate of photobleaching was reduced. Channels were filled with 3.3 μM and 0.33 μM GFP solutions, and fluorescent signal from the solutions in the channels were measured. The camera shutter was opened only during periodical exposures (~1 sec) to minimize photobleaching of the collected molecules.

In order to prevent non-specific binding of proteins, prior to and following each experiment, chips were exposed to a laser, for a period of time sufficient to completely quench residual fluorescence due to the non-specific binding of the fluorescent protein to the wall, in addition to use of freshly fabricated and filled devices, to eliminate carryover effects.

Pre-Concentration in Coated Channel

In order to prevent the adsorption of samples on untreated silica surfaces, a standard polyacrylamide coating (S.

Hjerten, *J. Chromatogr.* 347, 191-198 (1985)) was applied. The device was coated with 3-(trimethoxysilyl)propyl methacrylate as an adhesion promoter. Then, 5% polyacrylamide solution was mixed with 0.2% VA-086 photoinitiator (WAKO, Richmond, Va.) and exposed under a UV-lamp from 5 minutes, to initiate polymerization. After the coating, there was no noticeable level of adsorption to the device. Even though the polyacryamide coating process was expected to decrease surface potential and surface charge density, similar charge polarization and sample trapping pattern was observed (albeit with a lower efficiency) by applying a higher operating potential. The lower efficiency was overcome by adopting an even lower buffer ionic strength.

Preconcentration with Diverse Buffer Conditions

To demonstrate the adaptability of the device to different buffer conditions, buffer concentrations at different pH (5-9), different buffer solutions and different ionic strengths were evaluated. The operation of the device was also tested using an extract solution that comes directly from a polyacrylamide gel slice, after performing reduction, alkylation, trypsinization, and peptide isolation, simulating using bio samples directly from gel electrophoresis in the device, as in typical proteomics research environments. The extract solution contained no proteins, but small amounts of salts and small molecules may have been present in the gel from the sample or electrophoresis buffer (Tris, glycine, Sodium dodecyl sulfate, glycerol, Dithiothreitol, possible keratin contaminants), from staining (Coomassie blue), and/or from the reduction and alkylation steps (Tris(2-carboxy-ethyl)-phosphine hydrochloride, iodoacetamide, ammonium bicarbonate). The extraction by sonication was performed on the trypsinization solution (60 µL; 10 ng/µL trypsin and/or trypsin peptides in ammonium bicarbonate buffer) following enzyme inactivation with 20 µL of 20% formic acid. This extraction solution was collected and concentrated in the speedvac. Extraction with sonication was performed sequentially using 200 µL of 100 mM ammonium bicarbonate, 0.1% trifluoroacetic acid (TFA) in water, twice 0.1% TFA in 50:50 water to acetonitrile. Each time the extracted solution was collected and pooled with the extracted solution from the preceding step and concentrated down to approximately 10 µL in the speedvac. Then, this complex solution was used as a 'sample buffer' by adding labeled GFP molecules. For the preconcentration step, this simulated sample solution was diluted with 10 mM phosphate buffer (1:9 ratio) and loaded into the channel.

Example 1

Demonstration of Desalination

The desalination operation of micro/nanofluidic device at the unit device scale was experimentally tested. FIG. 11(*a*) shows the desalination experiment done with natural seawater (obtained from Crane beach, Ipswich, Mass., p11=8.4~8.5). NaOH was added at 1 mM final concentration to the natural seawater in order to precipitate $Ca^{2+}$ ions, which is known to cause significant precipitation in brine solution. This addition, however, did not decrease the salinity of the seawater significantly. Subsequently, seawater sample was physically pre-filtered in order to remove precipitations and large debris such as dirt, sand and seaweed (larger than the channel dimension). The seawater sample was then intentionally mixed with FITC (fluorescent dye as a molecular marker, 1 µg/mL, Invitrogen), polystyrene nanoparticles, r-phycoerythrin (r-PE, 1 ng/mL, Invitrogen) and human whole blood which had fluorescently stained white blood cells (WBCs) by Hoechst. Then the mixture (with the pH=9.1~9.2) was loaded into the reservoir of the device using external pressure pump at a defined flow rate (0.1~10 µL/min, depending on the dimensions of the channel used).

The external flow rate was generated by a syringe pump (Harvard apparatus, PHD 2200). All the flow patterns and particle motions were imaged with an inverted fluorescence microscope (Olympus, IX-51) and a CCD camera (Sensi-Cam, Cooke corp.). Sequences of images were analyzed by Image Pro Plus 5.0 (Media Cybernetics inc.). A de power supply (Stanford Research System, Inc.) was used to apply electric potential to each reservoir through a custom-made voltage divider. As shown in FIG. 1(*a*), Pt wires (Sigma Aldrich) were placed into each reservoir for proper external electrical connections.

Once ICP is initiated, the depletion zone was formed within 1 sec to divert charged ions (represented by dye molecules) into the "salted" stream as shown in FIG. 11(*a*). It was also shown that the ICP layer acts as a virtual barrier for any charged particles (both negative and positive), including most solid particles, micro-organisms and biomolecules (proteins, bacteria, viruses, RBCs, WBCs, etc.) found in seawater as shown in FIG. 11(*b*). The device shown in FIG. 11(*b*) has the inlet microchannel dimension of 100 µm width×15 µm depth in order to clearly visualize the movements of WBCs. This is because most waterborne microorganisms and microparticles have non-zero (usually slightly-negative) zeta potential. Therefore, both small salt ions and large microorganisms can be removed from the output desalted stream, making this process highly attractive for direct seawater desalination from natural sources. Since most of the ions were removed from the desalted stream, the pH value of output desalted stream was measured to be 7.0~7.5, which is in the range of WHO recommended acidity of drinking water. It was confirmed that the desalination operation can be maintained over 1 hour without any membrane clogging. After 1 hour operation, the reservoir at the end of the brine (salted) channel became concentrated with particles and dyes, as shown in FIG. 11(*c*), while the reservoir at the desalted channel was free from debris as shown in FIG. 11(*d*).

Example 2

Conductivity Measurement of Desalted Stream

The ionic concentration of seawater in the desalted stream is significantly lower than the original concentration, due to the repulsion of salts from the ion depletion zone. In order to quantify the concentration in a desalted stream, in situ conductivity measurement of desalted stream was done using embedded microelectrodes (shown in FIG. 10(*a*)). The potential drop (ΔV) between the microelectrodes was measured by Keithley 6514 electrometers and the current (i) through a "desalted" stream was obtained by Keithley 6487 picoammeters. The conductivity, □ can be simply calculated by the relation, □=i/|E|A, where i is the current passed through microelectrodes and A is the cross-sectional area of microchannel. E can be estimated by the potential drop divided by the gap between microelectrodes. For calibration, the conductivity of seawater of different dilution was measured using a benchtop conductivity meter (VWR sympHony conductivity meter), and the values were 45 mS/cm, 9.91 mS/cm, 1292 □ S/cm, 127.8 □S/cm, 12.4 □S/cm and 1.8 DS/cm for 1×, 5×, 50×, 500×, 5000× and 50000×dilution, respectively. This number was used to convert the measured conductivity to the salinity of the desalted stream.

Figure 13:
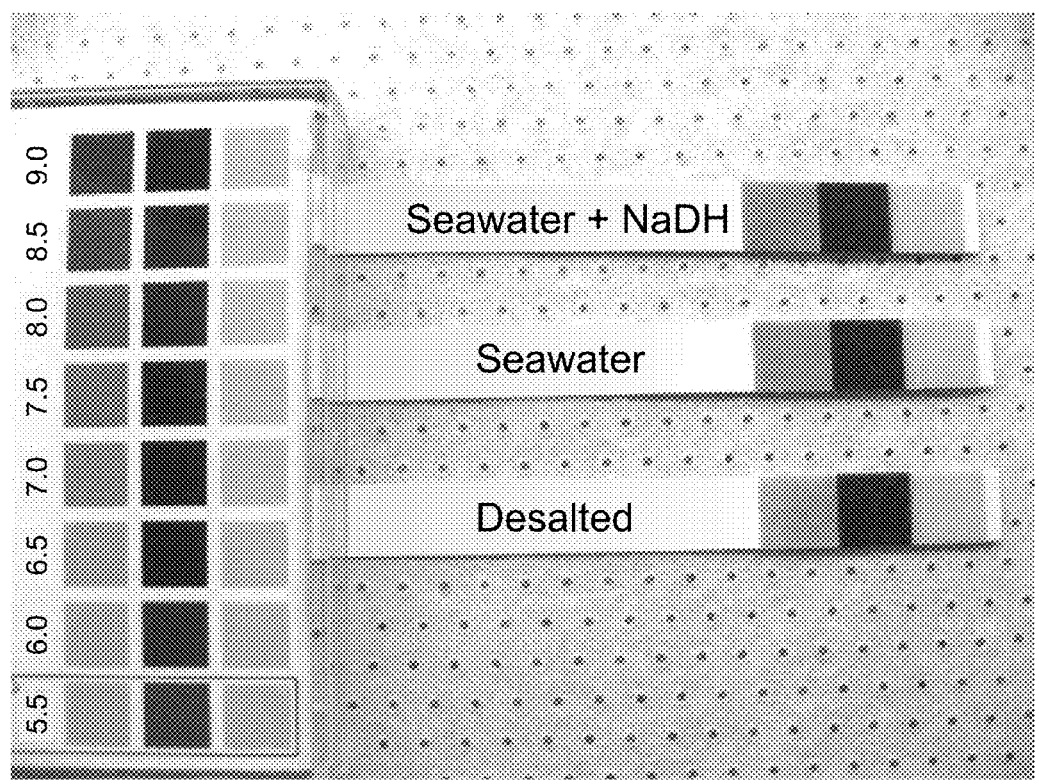
FIG. 13 demonstrates pH value estimation using litmus paper for seawater, for seawater+NaOH mixture and for a desalted sample.
Figure 14:
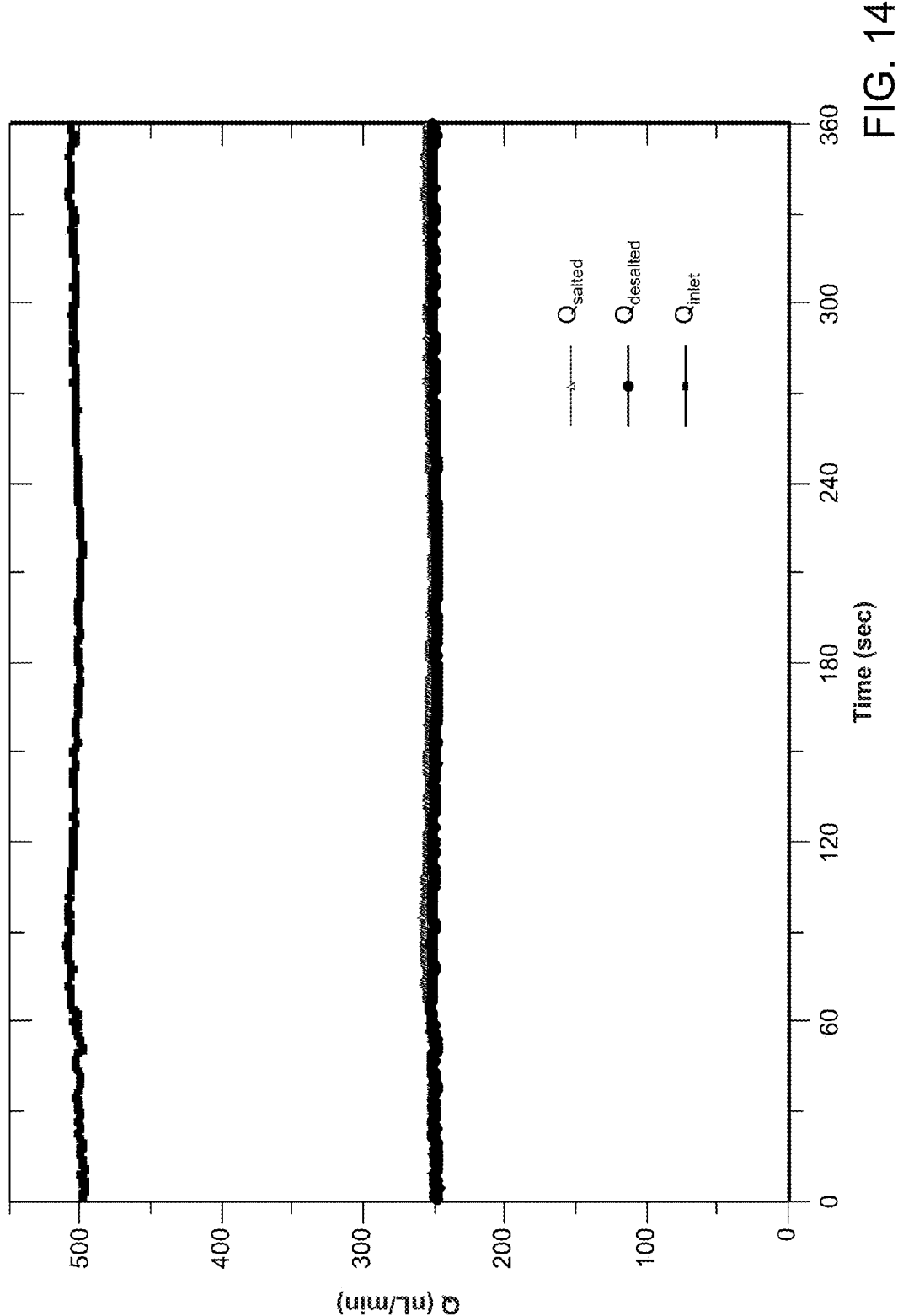
FIG. 14 illustrates the actual flow rate at the end of each microchannel. Due to the flow sensor specifications, the measurement was done at 500 nL/min inlet flow rate with 100 µm width×15 µm depth device. The inlet flow was almost equally divided into each microchannel (250 nL/min).

When the above-threshold voltage is applied and ion depletion zone is established, the conductivity of the output desalted stream dropped to ~0.5 mS/cm (~3 mM salinity) from ~45 mS/cm (~500 mM), the conductivity of original seawater. In another experiment with 100 mM phosphate buffer solution (~15 mS/cm, a model for brackish water), output desalted stream conductivity was also decreased to ~0.3 mS/cm (~2 mM). In comparison, the salinity of potable water should be lower than 10 mM level. The flow rate at the desalted stream realized in this initial proof-of-concept device was ~10 μL/min (inlet flow rate was 20 μL/min and it equally splits into two 10 μL/min streams), with |E| of ~75 V/cm.

pH values of a desalted sample were measured by a bench-top pH meter (VWR sympHony conductivity meter). They were 8.4~8.5 and 9.1~9.2 for natural seawater and seawater+NaOH mixture (after $Ca^{2+}$ removal and addition of cells), respectively. At the same time, pH values of pure seawater, seawater+NaOH mixture and desalted sample were measured using a Litmus paper (colorpHast, EMD chemicals inc.) as shown in FIG. 13. From the observation, the pH of the desalted sample had clearly lower value than that of both seawater samples, estimated to be between 7.0 and 7.5. Each microchannel was connected with Nanoflow sensor (Upchurch, N-565) in order to in situ measure the actual flow rates coming out from each microchannel. As shown in FIG. 14, the inlet flow rate was almost equally divided into the branched microchannels.

Example 3

Power Consumption

The steady-state current required in our unit was found to be 1 μA (seawater desalination output at 0.25 μL/min in a device with a microchannel cross section of 100 μm×15 μm) or ~30 μA (10 μL/min in a device with 500 μm×100 μm cross section). Thus, the power consumption was approximately 75 μW~2250 μW per unit device. Therefore, the energy efficiency of this desalting mechanism is 5 Wh/L (75 μW/0.25 μL/min)~3.75 Wh/L (2250 μW/10 μL/min). In addition to this, the energy for fluid delivery through a microchannel is also required and it is 0.041 mWh/L~1.55 mWh/L. In case of flow rate of Q=0.25 μL/min in 100 μm×15 μm device, the power required for pumping through the microchannel can be calculated by the product of pressure times flow rate (p×Q). The pressure drop across the entire microchannel is given by $12 \eta QL/(wd^3)$ where η is the viscosity of seawater, and L, w, and d are the length, width and depth of microchannel, respectively. By adapting η=1.88 cp, L=2 cm, w=100 μm, and d=15 μm, the power consumption was 23.2 nW. Thus, power efficiency (W/Q) was 1.55 mWh/L. Similarly, the efficiency was 0.041 mWh/L when Q=10 μL/min in 500 μm×100 μm cross-section device. Therefore, the power needed for general fluid delivery is negligible, mainly because of smaller fluidic resistance of an open microchannel, compared with RO membranes.

In contrast, the actual energy consumption of the RO process alone is ~2.5 W/L, but it is significantly increased up to 5 Wh/L because of the additional intake, pretreatment, recirculation and distribution processes needed. In addition, such power efficiency of the RO process is only achieved in large plant scale RO facilities. Small scale RO systems such as shipboard desalination system tend to have much worse power efficiency. Commercially available, small scale (but not portable) desalination systems, which has desalination throughput ranging between 378 L/day (262 mL/min) and 17000 L/day (11.8 L/min) capabilities and system volumes ranging between [40 cm×60 cm×40 cm] and [140 cm×110 cm×90 cm], required 2~3 hp (1491.4 W~2231.7 W) pumping motor for RO operation. These numbers lead 35 Wh/L~95 Wh/L of power efficiency. Therefore, total energy consumption of ICP desalination system would be at least comparable to the state-of-the art RO facility, and much lower than currently existing small scale RO systems. Similar to RO system, the power consumption can be further lowered with source water at lower salinity than seawater (e.g. brackish water). The theoretical lower bound of the energy required for desalination is approximately 0.81, 0.97 and 1.29 Wh/L for fresh water recoveries of 25, 50, 75%, respectively. Furthermore, the unit microfluidic device can be further optimized by implementing a number of improvements: 1) Firstly, the microelectrodes can be integrated for the applying voltages near the nanojunction in order to drastically decrease both the voltage and the power efficiency for the compatibility with existing battery technology or small-scale solar power; 2) Secondly, the length of a co-polymer of tetrafluorethylene and sulfonic acid nanojunction can be controlled, significantly reducing power loss due to the initiation and maintenance of ion depletion zone; 3) Finally, one can optimize the design of the main/brine channel in order to minimize the overall unit chip size, so that one can achieve maximum parallelization within a given system size.

With regards to the percentages given above for fresh water recoveries of 25, 50, 75%, the percentage means the relative amount of freshwater compared with the input seawater: 75% recovery means 75% of input seawater comes out as freshwater, while the remaining 25% comes out as a highly salted brine. In another embodiment, percentage of recovery describes the reduction of in salinity as a result of the process, for example, 75% recovery means that the concentration of solution is going to be ¼ (25%) after treatment; from 100 mM to 25 mM as a result of the desalination process.

Example 4

Parallelization of Unit Device

Figure 15:
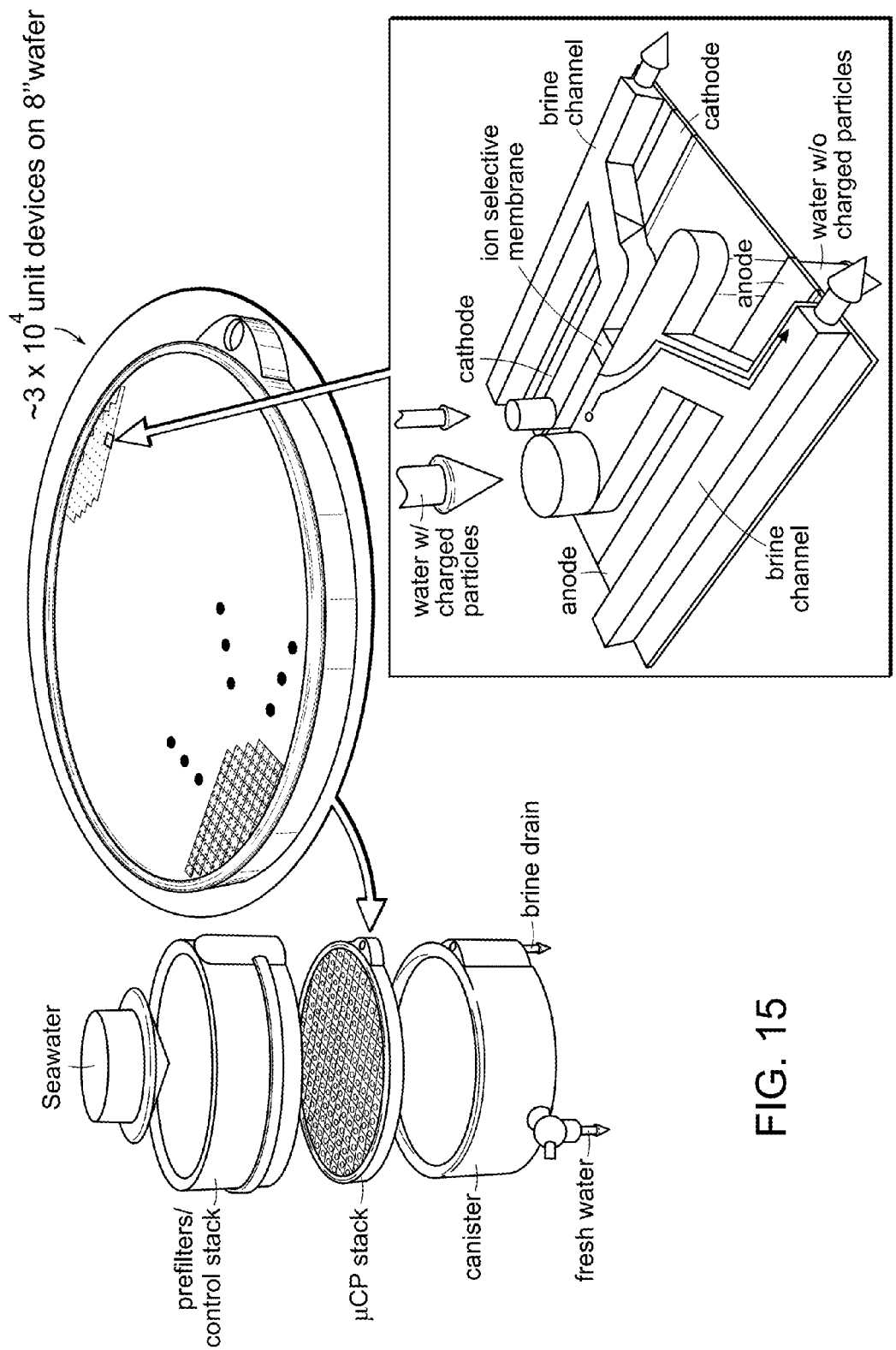
FIG. 15 is an illustration of one embodiment of: (Left) Gravity-fed ICP desalination system; µCP stack has many parallel microfluidic ICP-devices for salt/pathogen removal. Prefilter can eliminate larger particles. (Right) Perspective of a unit device.

The critical salt removal step occurs within a relatively short distance in the microchannel, so the lateral space (area) required for a unit microfluidic device was estimated to be around 1 mm×1 mm. Massive parallelization of the unit device over 6~8 inch wafer scale (17600~31400 $mm^2$, which allows multiplication up to $1.5 \times 10^4$~$3 \times 10^4$) would enable the throughput of 150 mL/min~300 mL/min in a small-scale system, which is ideally suited for portable seawater desalination application. In such a system, fluids are driven through pre-filter stack for removing large particles/debris and the massively parallel ICP desalter array stack via gravity (similar to household filtration systems) in order to eliminate both pathogens and salts as shown in FIG. 15.

In comparison, gravity-fed commercial household water purification system (not desalination system) has ~200 mL/min throughout and one of the current commercially available, desktop-size (but not portable) seawater desalination systems utilizing RO technology has the flow rate of 260 mL/min~1 L/min. Massive parallelization of unit device does require significant engineering efforts and such levels of parallelization of small unit device over a large area is not unprecedented, and is already being done in photovoltaic power generation.

Example 5

Figure 6A:
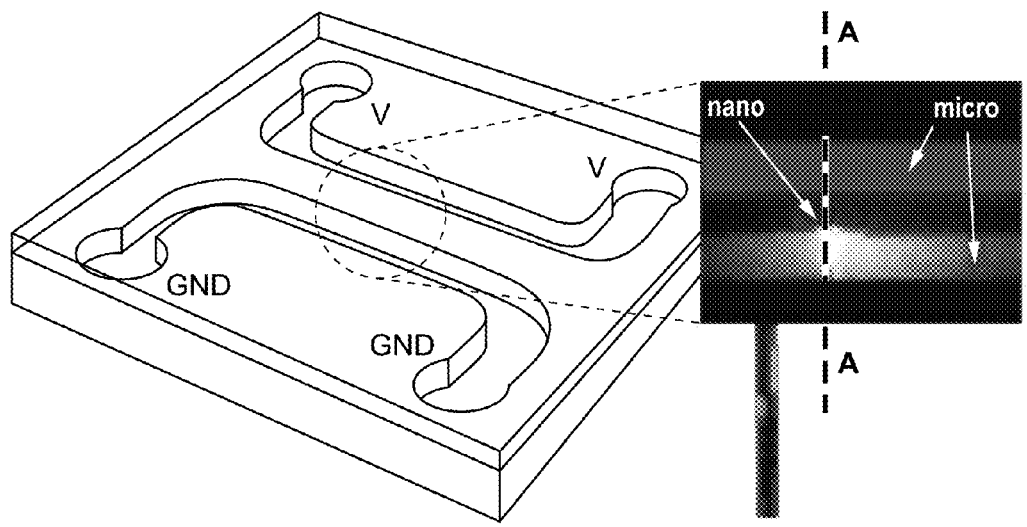
FIG. 6 schematically depicts a (A) single gate (SG) device and (B) a dual gate (DG) device.
Figure 6B:
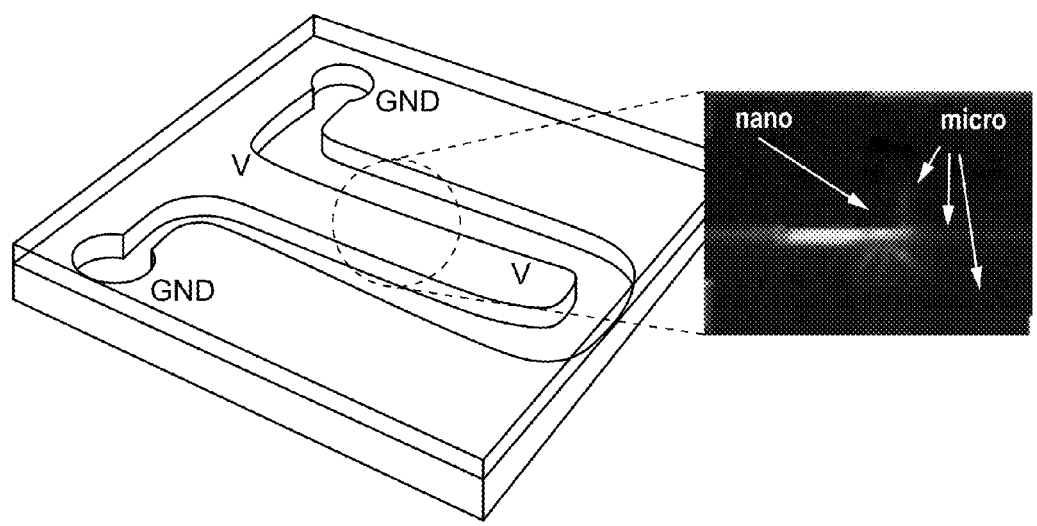

Specific Orientation of the Channels can Increase Stability of the Space Charge Region FIG. 6 presents embodiments of the devices of this invention which were fabricated. Based on the channel opening, the devices were categorized as a single gate device (SG, FIG. 6A) or dual gate device (DG, FIG. 6B). The sample microchannel connects to the conduit(s) on one side wall in the SG device and on both side walls in the DG device. The dimensions are 50 μm width×2 μm depth for the microchannel and 40 nm depth×2 μm width×10 μm height.

To explore the nonlinear flow in detail, the electrokinetic flow pattern inside and outside the ion depletion region were visualized by tracking fluorescence of tagged-particles and dye molecules, which were added in the main buffer solution (1 mM phosphate ((dibasic sodium phosphate)) at pH=8.7. 40 nm (Duke Scientific Corp) or 500 nm (Invitrogen) carboxy-terminated polystyrene beads were used, depending on the geometric properties of the chip.

Figure 7:
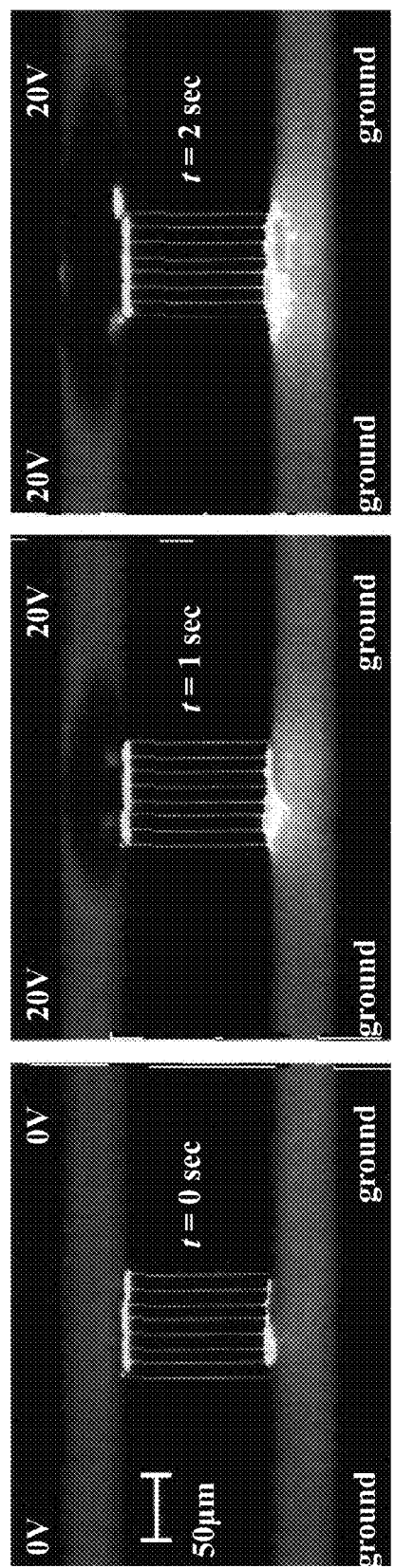
FIG. 7 demonstrates basic ion-enrichment and ion-depletion behavior in an embodiment of an SG device. The same voltage was applied to the first and second sides of the sample microchannel and the two sides of the buffer channel were electrically grounded. An ion-enriched zone (light) was formed in the buffer microchannel in an area proximal to the conduits. An ion depletion zone (dark) was formed in the sample microchannel in an area proximal to the conduits. Both depletion and enrichment regions were rapidly expanded.

Ion depletion and ion enrichment behavior were tested in the SG device (FIG. 7). The same voltage was applied to both sides of the sample microchannel and the buffer microchannel was grounded on both sides (depletion conditions). This resulted in ion concentration enhancement in the buffer microchannel proximal to the conduit (light) and ion depletion in the sample microchannel proximal to the conduits (dark) with the depletion zone quickly expanding in size.

Tangential electric fields ($E_T$) generated by applying different electric voltages at the two sides of the sample microchannel caused charged particles and ions to migrate. Charged particles and ions may be collected proximal to the first (left) side of the sample microchannel (FIG. 8).

Figure 9A:
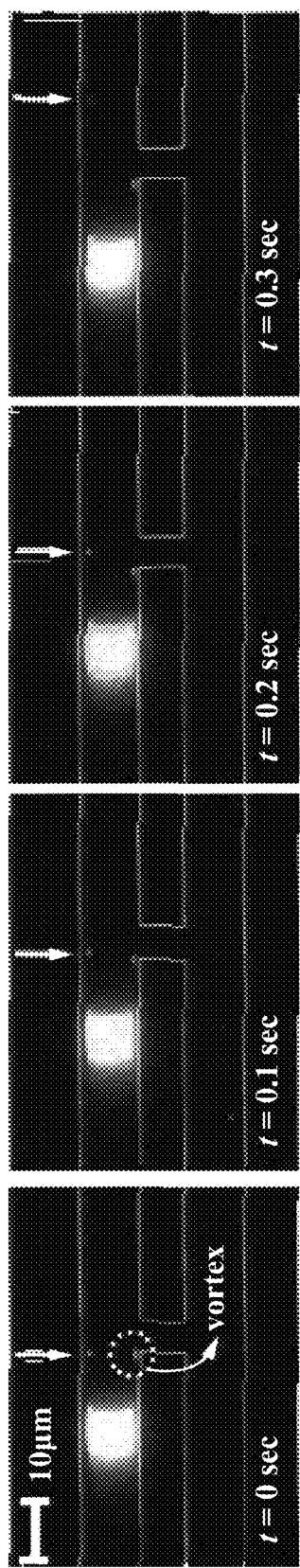
FIG. 9 demonstrates electrokinetic migration using an embodiment of an (a) SG and (b) DG device. The estimated velocity of pointed particles was approximately (a) 140 □ m/sec at $V_H$=10V and $V_L$=5V and (b) 500 □m/sec at $V_H$=10 V and $V_L$=5 V.
Figure 9B:
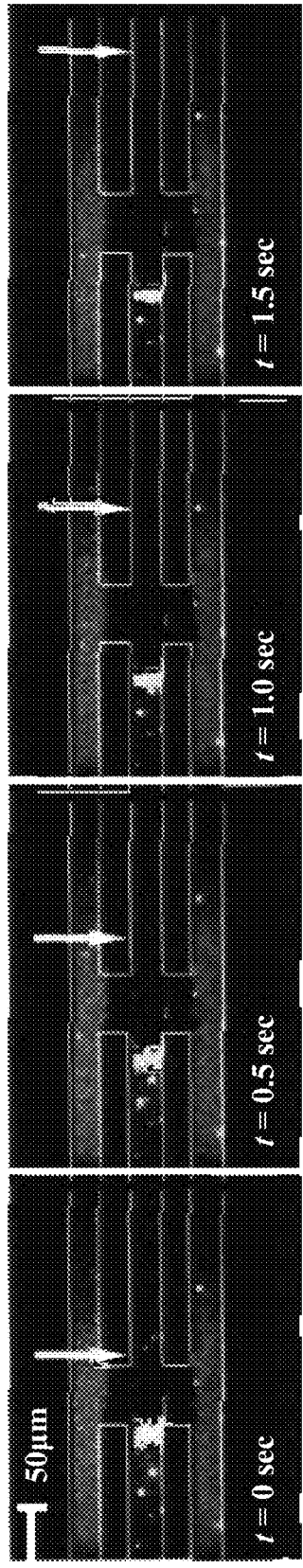

In order to track the flow pattern within regions of the sample microchannel, the particles were permitted to move across the depletion zone to return to the pre-concentration voltage configuration (FIG. 9). Once the particles passed the depletion zone and entered the downstream low concentration zone, they traveled at a speed that was roughly 25 times faster than in the concentration zone. Voltages applied were as follows: In FIG. 9(a) $V_H$=10V, $V_L$=5V and the buffer channel was grounded. In FIG. 9(b) three steps were performed. At first, $V_H$=20V, $V_L$=15V and the buffer channel was grounded for forming a depletion zone; next, $V_H$=20V, $V_L$=15V and the buffer channel remained unconnected (floated) for letting the particles across the depletion zone; in the last step, voltage conditions were turned back to $V_H$=20V, $V_L$=15V and a grounded buffer channel in order to recreate a depletion zone.

In the SG device of FIG. 9a, the particle speed in the high concentration zone was 6 μm/sec, while in the low concentration zone it was 140 μm/sec. The speed of the particle in the high concentration zone of the DG device (FIG. 9b) was 20 μm/sec, and in the low concentration zone it was 500 μm/sec. On the left hand side of the sample microchannel (concentration zone) the force (electrostatic in nature, always acting away form the conduit) responsible for ion depletion in counteracting the electrokinetic driving force, allows the particles to be trapped. However, in the right hand side, these two forces are acting in the same direction, thereby quickly removing particles (charged) from the region.

The liquid level change in sample reservoirs was measured. Only ion and charged particles were trapped in the concentration region, while water passed through the concentration zone and moved to the right side of the sample microchannel with high speed. The measured flow rate was approximately 0.5 μL/hr, which was 25 times greater than the flow rate at a normal electroosmotic flow (0.02 μL/hr) with the same electrical potential difference.

The right side of the sample microchannel, on the right of the conduit linkage area is referred to as the downstream zone. The downstream zones of the preconcentration (depletion) SG and DG devices were found to be largely salt-free. The buffer concentration in the downstream region can be estimated by turning off the voltage across the conduit, and then electrokinetically mobilizing the particles and dye molecules in both regions. The ion concentration in the downstream region was estimated to be at least 40 μM, as assessed by comparing two different particle speeds in two zones, since the particle speed is correlated with the electrical resistivity and ionic concentration of the buffer solution. The ion concentration was estimated based on the difference between particle speeds in two configurations, since the speed is directly proportional to the electric field which is in turn inversely proportional to the concentration. An ion concentration in the DM range is the concentration expected using this embodiment of the method. The conductance of the perm-selective conduit (and the total perm-selective current through it) is large enough, in some embodiments of this invention, to "desalt" the ions from the liquid volume coming into the conduit junction in the SG and DG devices. This downstream desalting enhances the electrokinetic flow in the region.

The conductance of the perm-selective conduit (and the total perm-selective current through it) is large enough, in some embodiments of this invention, to cause switching of the direction of ion and liquid flow from the liquid volume coming into the conduit junction in the SG and DG devices. This switching can be used in the operation of microfluidic devices. In the directed accumulation of species and in controlled synthesis, analysis and purification techniques.

Example 6

Low Power Desalination of Sea Water for Drinking

A microfluidic device is constructed from an array of microchannels/conduit assemblies as described in Example 1. The array is three dimensional. The device is hand-held. The microfluidic device is connected to a sea water reservoir. Sea water is first filtered to eliminate micron size and larger particles. The sea water enters the plurality of the microchannels. Sea water is then being desalinated by applying an electric field to the conduits. On the outlet of each channel, the desalinated stream is collected by one container and the salted stream by another container. The contents of all the containers in which desalinated water were collected are directed to one outlet container for drinking. The device is low-power operated and can work on batteries or on other temporary power supply devices. The device can desalinate large amounts of water because a huge number of microchannels can be constructed and work in parallel within one device. Enhancing fluid flow enhances the efficiency of the device. Water that was desalinated once to some extent, can be further desalinated by recycling the desalinated stream, or by directing the desalinated stream to a second set of desalinating microchannels. The device can be connected to a conductance meter or to any other charged species concentration meter to evaluate salt concentration of the desalinated solution.

Example 7

A Microfluidic Device for Synthesis

A microfluidic device is constructed from a multitude of microchannels/conduit assemblies as described in Example 1. The outlet of some of the microchannels is connected to chambers or reservoirs. A mixture of reagents of a first type is loaded in the device and transferred to a chamber through one microchannel. A mixture of reagents of a second type is loaded into the device through the same or an additional microchannel and is transferred to the same chamber or reservoir. The presence of the two types of reagent mixtures in a chamber results in a reaction. Since at least portions of the device are transparent, imaging techniques can be used, such that markers can indicate the presence and the location of the reagents and of the reaction products. In some embodiments, the products are released from the chamber into a microchannel leading to a collection container. The device may contain an array of reaction containers all working in concert to enhance the efficiency of the reaction. The ability to enhance fluid flow, to switch the direction of the fluid and to purify parts of the solution by eliminating charged species from it, renders the synthesis efficient, fast and highly controlled in terms of product purity and product yield.

Example 8

Implanted Microfluidic Device for Controlled Drug Release and Diagnosis

Devices of this invention may be implanted in a subject or attached to a subject skin as part of a controlled drug-release system. Controlled application of voltage on conduits of this invention, induces fluid flow through microchannels of the device. It also induces enhanced fluid flow. Such action may drive a fluid containing drugs into a subject at measured amounts and in specific time intervals. Fluid samples from a subject are withdrawn from the subject for analysis. Small fluid samples are pumped into the microchannels of the device for diagnosis. Pumping is achieved by the application of a voltage on the conduits and on the microchannels. The sample is analyzed and can be transferred back to the subject. Alternately the sample is disposable.

What is claimed is:

1. A method for accelerating liquid flow in a microfluidic device, the method comprising the steps of:
   introducing a liquid comprising charged species from a source into the microfluidic device comprising:
   i. a first substrate;
   ii. at least one sample microchannel through which said liquid comprising charged species can be made to pass from a first side to a second side;
   iii. at least one buffer microchannel or reservoir comprising a buffer;
   iv. at least one conduit linked to said sample microchannel and to said buffer microchannel or reservoir; and
   v. at least one unit to induce an electric field in said conduit, said sample microchannel, said buffer microchannel or reservoir or a combination thereof;
   inducing a first electric field in said sample microchannel whereby electroosmotic flow is induced in said sample microchannel, said flow further introducing said liquid into said device through said sample microchannel and said flow is controlled by the strength of said first electric field;
   inducing a second electric field in said conduit, whereby ion depletion occurs in said sample microchannel in a region proximal to said conduit when said at least one buffer microchannel or reservoir is electrically grounded and a potential difference over said conduit is produced and whereby said ion depletion accelerates flow in said sample microchannel; and
   employing a burst mode operation of electrokinetic pumping of said flow such that a voltage difference between said first side and said second side maintains ionic strength and charged species contents of said flow.

2. The method of claim 1, wherein said liquid introduction from a source into said microfluidic device comprising the use of a pressure inducing unit, an electroosmotic flow inducing unit or a combination thereof.

3. The method of claim 1, wherein said microfluidic device further comprises a second substrate positioned proximally to or adhered to said first substrate or a portion thereof.

4. The method of claim 1, wherein said first electric field in said sample microchannel is generated by applying a higher voltage to said first side of said sample microchannel and a lower voltage to said second side of said sample microchannel.

5. The method of claim 4, wherein said higher voltage, said lower voltage or a combination thereof is positive voltage.

6. The method of claim 5, wherein said positive voltage is between 50 mV and 500 V.

7. The method of claim 4, wherein said higher voltage is positive and said lower voltage is achieved by electrically grounding said second side of said sample microchannel.

8. The method of claim 1, wherein said second electric field in said conduit is generated by applying a higher voltage to the side of said conduit that is linked to said sample microchannel and a lower voltage to the side of said conduit that is linked to said buffer microchannel.

9. The method of claim 8, wherein said higher voltage is positive and said lower voltage is applied by electrically grounding said buffer microchannel or reservoir linked to said conduit.

10. The method of claim 8, wherein said higher voltage is the result of the two voltages applied to said first side and to said second side of said sample microchannel.

11. The method of claim 8, wherein said higher voltage has an intermediate value lying between the values of a first voltage applied to said first side of said sample microchannel and a second voltage applied to said second side of said sample microchannel.

12. The method of claim 1, wherein said first and second electric fields are 75 V/cm to said first side of said sample microchannel and 40 V/cm to said second side of said sample microchannel and wherein said buffer microchannel or reservoir is electrically grounded.

13. The method of claim 1, whereby upon introduction of a solution comprising charged species to said sample microchannel and independent induction of said electric field in said conduit and said electric field in said sample microchannel, said charged species are confined to a region within said sample microchannel that is distant from said conduit.

14. The method of claim 1, wherein said sample microchannel further comprising a first outlet for low salt concentration solution and a second outlet for high salt concentration solution.

15. The method of claim 1, wherein the width of said sample microchannel, said buffer microchannel or a combination thereof is between 1-100 µm.

16. The method of claim 1, wherein the depth of said sample microchannel, said buffer microchannel or a combination thereof is between 0.5-50 µm.

17. The method of claim 1, wherein the width of said conduit is between 100-4000 nanometers.

18. The device of claim 1, wherein the width of said conduit is between 1-100 micrometers.

19. The method of claim 1, wherein the depth of said conduit is between 20-100 nanometers.

20. The device of claim 1, wherein the depth of said conduit is between 1-100 micrometers.

21. The method of claim 1, wherein said conduit is a nanochannel.

22. The method of claim 1, wherein said conduit comprising a polymer-based permselective material.

23. The method of claim 22, wherein said polymer-based permselective material comprising a co-polymer of tetrafluoroethylene and sulfonic acid.

24. The method of claim 22, wherein said polymer-based permselective material comprising a cation selective or an anion selective material.

25. The method of claim 1, wherein said conduit comprising an electrical junction that is preferentially conductive to positive ions or to negative ions.

26. The method of claim 1, wherein the surface of said sample microchannel has been functionalized to reduce adsorption of species of interest to said surface.

27. The method of claim 1, wherein the surface of said conduit and/or said first or buffer microchannel has been functionalized to enhance the operation efficiency of the device.

28. The method of claim 1, wherein an external gate voltage is applied to the substrate of the device, to enhance the operation efficiency of the device.

29. The method of claim 1, wherein said sample microchannel, said buffer microchannel, said conduit or combination thereof, are formed by lithography and etching processes.

30. The method of claim 1, wherein said device is comprised of a transparent material.

31. The method of claim 30, wherein said transparent material is borosilicate glass (Pyrex™), silicon dioxide, silicon nitride, quartz or SU-8.

32. The method of claim 1, wherein said device is coated with a low-autofluorescent material.

33. The method of claim 1, wherein said device is coupled to a pump.

34. The method of claim 1, wherein said device is coupled to a sensor, separation system, detection system, analysis system or combination thereof.

35. The method of claim 34, wherein said detection system comprises an illumination source, a camera, a computer, a luminometer, a spectrophotometer, or a combination thereof.

36. The method of claim 1, wherein liquid flow speed in said sample microchannel is between 100 μm/sec and 10 mm/sec.

37. The method of claim 1, wherein said device comprises multiple sample microchannels, multiple buffer microchannels, multiple conduits or combinations thereof.

38. The method of claim 37, wherein said multiple microchannels, conduits or combinations thereof are arranged with a particular geometry or in an array.

39. The method of claim 38, wherein said array comprises at least 1000 sample microchannels, at least 1000 buffer microchannels and at least 1000 conduits.

40. The method of claim 37, wherein said device length, width, height or a combination thereof ranges between 10 cm to 30 cm.

41. The method of claim 38, wherein said geometry or said array comprises perpendicular orientation of said microchannels with respect to said conduits.

42. The method of claim 37, wherein liquid volume flow rate is at least 1 mL/min.

43. The method of claim 37, wherein liquid volume flow rate ranges between 60-100 L/hour.

44. The method of claim 1, wherein said liquid comprising charged species is sea water.

45. The method of claim 1, wherein electrical power needed for device operation ranges between 10 w to 100 w.

46. The method of claim 1, wherein flow through said sample microchannel is continuous.

47. The method of claim 1, wherein said device is part of an apparatus.

48. The method of claim 47, wherein said apparatus is handheld/portable.

49. The method of claim 47, wherein said apparatus is a table top apparatus.

50. A method of collecting a desalted solution in a continuous manner, the method comprising the steps of:
  introducing a liquid comprising salt ions from a source into a microfluidic device comprising:
    i. a substrate;
    ii. at least one sample microchannel through which said liquid comprising salt ions can be made to pass from a first side to a second side;
    iii. at least one buffer microchannel or buffer reservoir comprising a buffer;
    iv. at least one conduit linked to said sample microchannel and to said buffer microchannel or reservoir; and
    v. at least one unit to induce an electric field in said conduit, said sample microchannel, said buffer microchannel or buffer reservoir or a combination thereof; and
  inducing a first electric field in said sample microchannel whereby electroosmotic flow is induced in said sample microchannel, said flow further introducing said liquid into said device through said sample microchannel by either electrokinetic driven or pressure driven or combination thereof and said flow is controlled by the strength of said first electric field;
  inducing a second electric field in said conduit, whereby salt ion depletion occurs in said sample microchannel in a region proximal to said conduit when said at least one buffer microchannel or reservoir is electrically grounded and a potential difference over said conduit is produced and whereby said salt ions and any charged species including biological contaminants such as bacteria and virus are confined to a region within said sample microchannel that is distant from said conduit; and
  employing a burst mode operation of electrokinetic pumping of said flow such that a voltage difference between said first side and said second side maintains ionic strength and contents of said flow.

51. The method of claim 50, wherein said liquid introduction from a source into said microfluidic device comprising a pressure inducing unit, an electroosmotic flow inducing unit or a combination thereof 52. The method of claim 50, wherein said microfluidic device further comprising a second substrate positioned proximally to or adhered to said first substrate or a portion thereof.

53. The method of claim 50, wherein said liquid comprising salt is sea water.

54. The method of claim 50, wherein said method is used for desalting sea water for drinking.

55. The method of claim 50, wherein said sample microchannel further comprising a first outlet for low salt concentration solution and a second outlet for high salt concentration solution.

56. The method of claim 55, wherein said first outlet for low salt concentration solution is linked to said ion depletion zone in said sample microchannel and wherein said second outlet for high salt concentration solution is linked to said region that is distant from said conduit wherein salt ions are confined.

57. The method of claim 50, wherein said first electric field in said sample microchannel is generated by applying a higher voltage to said first side of said sample microchannel and a lower voltage to said second side of said sample microchannel.

58. The method of claim 57, wherein said higher voltage, said lower voltage or a combination thereof are positive voltages.

59. The method of claim 58, wherein said positive voltage is between 50 mV and 500 V.

60. The method of claim 57, wherein said higher voltage is positive and said lower voltage is achieved by electrically grounding said second side of said sample microchannel.

61. The method of claim 50, wherein said second electric field in said conduit is generated by applying a higher voltage to the side of said conduit that is linked to said sample microchannel and a lower voltage to the side of said conduit that is linked to said buffer microchannel.

62. The method of claim 61, wherein said higher voltage is positive and said lower voltage is applied by electrically grounding said buffer microchannel or reservoir linked to said conduit.

63. The method of claim 61, wherein said higher voltage is the result of the two voltages applied to said first side and to said second side of said sample microchannel.

64. The method of claim 61, wherein said higher voltage has an intermediate value lying between the values of a first voltage applied to said first side of said sample microchannel and a second voltage applies to said second side of said sample microchannel.

65. The method of claim 50, wherein said first and second electric fields are 75 V/cm to said first side of said sample microchannel and 40 V/cm to said second side of said sample microchannel and wherein said buffer microchannel or reservoir is electrically grounded.

66. The method of claim 50, wherein the width of said sample microchannel, said buffer microchannel or a combination thereof is between 1-100 μm.

67. The method of claim 50, wherein the depth of said sample microchannel, said buffer microchannel or a combination thereof is between 0.5-50 μm.

68. The method of claim 50, wherein the width of said conduit is between 100-4000 nanometers.

69. The method of claim 50, wherein the width of said conduit is between 1-100 micrometers.

70. The method of claim 50, wherein the depth of said conduit is between 20-100 nanometers.

71. The method of claim 50, wherein the depth of said conduit is between 1-100 micrometers.

72. The method of claim 50, wherein said conduit is a nanochannel.

73. The method of claim 50, wherein said conduit comprising a polymer-based permselective material.

74. The method of claim 73, wherein said polymer-based permselective material comprising a co-polymer of tetrafluoroethylene and sulfonic acid.

75. The method of claim 73, wherein said polymer-based permselective material comprising a cation selective or an anion selective material.

76. The method of claim 50, wherein said conduit comprising an electrical junction that is preferentially conductive to positive ions or to negative ions.

77. The method of claim 50, wherein the surface of said sample microchannel has been functionalized to reduce adsorption of species of interest to said surface.

78. The method of claim 50, wherein the surface of said conduit and/or said first or buffer microchannel has been functionalized to enhance the operation efficiency of the device.

79. The method of claim 50, wherein an external gate voltage is applied to the substrate of the device, to enhance the operation efficiency of the device.

80. The method of claim 50, wherein said sample microchannel, said buffer microchannel, said conduit or combination thereof, are formed by lithography and etching processes.

81. The method of claim 50, wherein said device is comprised of a transparent material.

82. The method of claim 50, wherein said transparent material is borosilicate glass (Pyrex™), silicon dioxide, silicon nitride, quartz or SU-8.

83. The method of claim 50, wherein said device is coated with a low-autofluorescent material.

84. The method of claim 50, wherein said device is coupled to a pump.

85. The method of claim 50, wherein said device is coupled to a sensor, separation system, detection system, analysis system or combination thereof.

86. The method of claim 85, wherein said detection system comprises an illumination source, a camera, a computer, a luminometer, a spectrophotometer, or a combination thereof.

87. The method of claim 50, wherein liquid flow speed in said sample microchannel is between 100 μm/sec and 10 mm/sec.

88. The method of claim 50, wherein said device comprises multiple sample microchannels, multiple buffer microchannels, multiple conduits or combinations thereof.

89. The method of claim 88, wherein said multiple microchannels, conduits or combinations thereof are arranged with a particular geometry or in an array.

90. The method of claim 89, wherein said array comprises at least 1000 sample microchannels, at least 1000 buffer microchannels and at least 1000 conduits.

91. The method of claim 88, wherein said device length, width, height or a combination thereof ranges between 10 cm to 30 cm.

92. The method of claim 89, wherein said geometry or said array comprises perpendicular orientation of said microchannels with respect to said conduits.

93. The method of claim 50, wherein liquid volume flow rate is at least 1 mL/min.

94. The method of claim 50, wherein liquid volume flow rate ranges between 60-100 L/hour.

95. The method of claim 50, wherein electrical power needed for device operation ranges between 10 w to 100 w.

96. The method of claim 50, wherein flow through said sample microchannel is continuous.

97. The method of claim 50, wherein said method is used for filtering solutions for synthesis, detection analysis, purification, disinfection, or a combination thereof.

98. The method of claim 50, wherein said method is used for removing contaminants from water.

* * * * *